United States Patent [19]
Yuan et al.

[11] Patent Number: 5,869,248
[45] Date of Patent: Feb. 9, 1999

[54] TARGETED CLEAVAGE OF RNA USING RIBONUCLEASE P TARGETING AND CLEAVAGE SEQUENCES

[75] Inventors: Yan Yuan; Cecilia Guerrier-Takada, both of New Haven; Sidney Altman, Hamden; Fenyong Liu, New Haven, all of Conn.

[73] Assignee: Yale University, New Haven, Conn.

[21] Appl. No.: 702,652

[22] PCT Filed: Mar. 7, 1994

[86] PCT No.: PCT/US95/02816

§ 371 Date: Nov. 6, 1996

§ 102(e) Date: Nov. 6, 1996

[87] PCT Pub. No.: WO95/24489

PCT Pub. Date: Sep. 14, 1995

Related U.S. Application Data

[63] Continuation-in-part of Ser. No. 207,547, Mar. 7, 1994, and Ser. No. 215,082, Mar. 18, 1994.

[51] Int. Cl.⁶ .............................. C12Q 1/68; C07H 21/02
[52] U.S. Cl. .................................. 435/6; 536/23.2
[58] Field of Search .................... 435/5, 6, 91.2

[56] References Cited

U.S. PATENT DOCUMENTS

| | | | |
|---|---|---|---|
| 4,868,116 | 9/1989 | Morgan et al. | 435/240.2 |
| 4,980,286 | 12/1990 | Morgan et al. | 435/172.3 |
| 4,987,071 | 1/1991 | Cech et al. | 435/91.2 |
| 5,168,053 | 12/1992 | Altman et al. | 435/91 |
| 5,225,347 | 7/1993 | Goldberg et al. | 435/320.1 |
| 5,334,711 | 8/1994 | Sproat et al. | 536/24.5 |
| 5,525,719 | 6/1996 | Srivastava et al. | 536/26.7 |
| 5,624,824 | 4/1997 | Yuan et al. | 435/91.2 |

FOREIGN PATENT DOCUMENTS

| | | |
|---|---|---|
| 0 321 021 | 6/1989 | European Pat. Off. . |
| 0 339 842 | 11/1989 | European Pat. Off. . |
| WO 88/04300 | 6/1988 | WIPO . |
| WO 89/05852 | 6/1989 | WIPO . |
| WO 89/07136 | 8/1989 | WIPO . |
| WO 90/02176 | 3/1990 | WIPO . |
| WO 90/02806 | 3/1990 | WIPO . |
| WO 91/04319 | 4/1991 | WIPO . |
| WO 91/04324 | 4/1991 | WIPO . |
| WO 91/16420 | 10/1991 | WIPO . |
| WO 91/17093 | 11/1991 | WIPO . |
| WO 92/03566 | 3/1992 | WIPO . |
| WO 93/01286 | 1/1993 | WIPO . |
| WO 93/22434 | 11/1993 | WIPO . |
| WO 94/13791 | 6/1994 | WIPO . |
| WO 94/13833 | 6/1994 | WIPO . |
| WO 94/15619 | 7/1994 | WIPO . |
| WO 95/23225 | 8/1995 | WIPO . |
| WO 95/24489 | 9/1995 | WIPO . |
| WO 95/27480 | 10/1995 | WIPO . |
| WO 96/18733 | 6/1996 | WIPO . |

OTHER PUBLICATIONS

Agrawal, et al., "Oligodeoxynucleoside phosphoramidates and phosphorothioates as inhibitors of human immunodeficiency virus," *Proc. Natl. Acad. Sci. USA* 85(19):7079–7083 (1988).
*# Altman, "Ribonulcease P: An Enzyme with a Catalytic RNA Subunit," *Adv. Enzymol. Relat. Areas Mol. Biol.* 62:1–36 (1989).
Altman, *Ann. Rev. Enzymology* 62:1–39 (1989).
*# Altman, et al, "Catalysis by the RNA Subunit of RNase P—A Minireview," *Gene* 82:63–64 (1989).
*# Altman, "Ribonuclease P,"*J. Biol. Chem.*, 265(33):20053–20056 (1990).
Altman, et al., "Nucleotide Sequences of the RNA Subunit of RNase P from Several Mammals,"*Genomics* 18(2):418–422 (1993).
Altman, "RNA enzyme–directed gene therapy," *Proc. Natl. Acad. Sci. USA* 90(23):10898–10900 (1993).
*# Baer, et al., "Structure and Transcription of a Human Gene for H1 RNA the RNA Component of Human RNase," *Nucleic Acids Res.*, 18:97–103 (1989).
*# Bartkiewicz, et al., "Identification and characterization of an RNA molecule that copurifies with RNase P activity from HeLa cells," *Genes Dev.* 3(4):488–499 (1989).
*# Beaudry, et al., "Directed Evolution of an RNA Enzyme," *Science,*257:635–641 91992).
Beigelman, et al., "Chemical Modification of Hammerhead Ribozymes," *J. Biol. Chem.* 270(43):25702–25708 (1995).
Bergot, et al., "Separation of synthetic phosphorothioate oligodeoxynucleotides from their oxygenated (phosphodiester) defect species by strong–anion–exchange high–performance liquid chromatography,"*J. Chromatogr.* 599(1 and 2):35–42 (1992).

(List continued on next page.)

*Primary Examiner*—Eggerton A. Campbell
*Attorney, Agent, or Firm*—Arnall Golden & Gregory LLP

[57] ABSTRACT

It has been discovered that any RNA can be targeted for cleavage by RNase P from prokaryotic or eukaryotic cells using a suitably designed oligonucleotide ("external guide sequence", or EGS) to form a hybrid with the target RNA, thereby creating a substrate for cleavage by RNase P in vitro. The EGS hydrogen bonds to the targeted RNA to form a partial tRNA like structure including the aminoacyl acceptor stem, the T stem and loop, and part of the D stem. An EGS can be modified both by changes in sequence and by chemical modifications to the nucleotides. The EGS can be a separate molecule or can be combined with an RNase P catalytic RNA sequence to form a single oligonucleotide molecule ("RNase P internal guide sequence" or RIGS). Methods are also disclosed to randomly select and to express a suitable EGS or RIGS in vivo to make a selected RNA a target for cleavage by a host cell RNase P or introduced RIGS, thus preventing expression of the function of the target RNA. The methods and compositions should be useful to prevent the expression of disease- or disorder-causing genes in vivo.

30 Claims, 12 Drawing Sheets

OTHER PUBLICATIONS

*# Berzal–Heranz, et al., "In vitro selection of active hairpin ribozymes by sequential RNA–catalyzed cleavage and ligation reactions," *Genes and Dev.*, 6(1):129–134 (1992).

Bordonaro, et al., "An Improved T1/A Ribonuclease Protection Assay," *Biotechniques* 16(3):428–430 (1994).

*# Branch, et al., A Replication Cycle for Viroids and Other Small Infectious RNA's, *Science*, 223:(4364):450–455 (1984).

*# Branch, et al., "An Ultraviolet–Sensitive RNA Strucural Element in Viroid–Like Domain of the Hepatitis Delta Virus," *Science*, 243:649–652 (1989).

Carrara, et al., "Two helices plus a linker: A small model substrate for eukaryotic RNase P," *Proc. Natl. Acad. Sci. USA* 92(7):2627–2631 (1995).

Castaigne, et al., "All–Trans Retinoic Acid as a Differentiation Therapy for Acute Promyelocytic Leukemia. I. Clinical Results," *Blood* 76(9):1704–1709 (1990).

* Cech, et al., *Cell* 31:147–157 (1982).

Cech, "Self–Splicing Of Group I Introns," *Annu. Rev. Biochem.* 59:543–568 (1990).

Cech, in "Structure and Mechanism of the Large Catalytic RNAs: Group I and Group II Introns and Ribonuclease P," *The RNA World* Chapter 11, pp. 239–269 (Gesteland and Atkins, eds., Cold Spring Harbor Laboratory Press, New York, 1993).

Chang, et al., "Characterization of a Fusion cDNA (RARA/myl) Transcribed from the t(15;17) Translocation Breakpoint in Acute Promyelocytic Leukemia," *Mol. Cell. Biol.* 12(2):800–810 (1992).

Cheson, "The Maturation of Differentiation Therapy,"*New England J. Med.* 327:422–424 (1992).

Chomczynski, et al., "Single–Step Method of RNA Isolation by Acid Guandinium Thiocyanate–Phenol–Chloroform Extraction, " *Anal. Biochem.* 162(1):156–159 (1987).

*# Chowrira, et al., "Novel guanosine requirement for catalysis by the hairpin ribozyme," *Nature*, 354(6351):320–322 (1991).

Christoffersen, et al., "Ribozymes as Human Therapeutic Agents," *Medicinal Chem.* 38(12):2023–23037 (1995).

Clarenc, et al., "Delivery of antisense oligonucleotides by poly(L–lysine) conjugation and liposome encapsulation," *Anti–Cancer Drug Design* 8:81–94 (1993).

Conrad, et al., "Enzymatic synthesis of 2'–modified nucleic acids: identification of important phosphate and ribose moieties in RNase P substrates," *Nucleic Acids Res.* 23(11):1845–1853 (1995).

Crooke, et al., "Progress in antisense oligonucleotide therapeutics," *Annu. Rev. Pharmacol. Toxicol.* 36:107–129 (1996).

* Crystal, et al., "Transfer of Genes to Humans Early Lessons and Obstacles to Success," *Science* 270:404–410 (1995).

Cummins, et al., "Characterization of fully 2'–modified oligoribonucleotide hetero– and homoduplex hybridization and nuclease sensitivity," *Nucleic Acids Res.* 23(11):2019–2024 (1995).

*# Das, et al., "Upstream regulatory elements are necessary and sufficient for transcription of a U6 RNA gene by RNA polymerase III," *EMBO* 7(2):503–512 (1988).

De The, et al., "The PML–RARα Fusion mRNA Generated by the t(15;17) Translocation in Acute Promyelocytic Leukemia Encodes a Functionally Altered RAR," *Cell* 66:675–684 (1991).

*# Doersen, et al., "Characterization of an RNase P Activity from HeLa Cell Mitochondria. Comparison with the Cytosol RNase P Activity," *J. Biol. Chem.* 260(10):5942–5949 (1985).

Ecker, et al., "Rational screening of oligonucleotide combinatorial libraries for drug discovery," *Nucleic Acids Res.* 21(8):1853–1856 (1993).

Felgner, et al., "Lipofection: A highly efficient, lipid–mediated DNA–transfection procedure," *Proc. Natl. Acad. Sci. USA* 84:7413–7417 (1987).

Felgner, "Particulate systems and polymers for in vitro and in vivo delivery of polynucleotides," *Advanced Drug Delivery Reviews*, 5:163–187 (1990).

Felgner, et al.,"Cationic liposome–mediated transfection," *Nature* 337:387–388 (1989).

*# Forster, et al., "External Guide Sequences for an RNA Enzyme," *Science* 249:783–786 (1990).

*# Forster, et al., "Self–Cleavage of Virusoid RNA Is Performed by the Proposed 55–Nucleotide Active Site," *Cell*, 50:9–16 (1987).

Fowlkes, et al., "Transcriptional Control Regions of the Adenovirus VAI RNA Gene," *Cell* 22(2):405–413 (1980).

Froehler, et al., "Oligodeoxynucleotides Containing C–5 Propyne Analogs of 2'–Deoxyuridine and 2'–Deoxycytidine," *Tetrahedron Letters* 33(37):5307–5310 (1992).

Gaur, et al., "Modification interference approach to detect ribose moieties important for the optimal activity of a ribozyme," *Nucleic Acids Res.* 21(1):21–26 (1993).

*# Green, et al., "In Vitro genetic analysis of the Tetrahymena self–splicing intron," *Nature*, 347(6291)406–408 (1990).

Grignani, et al., "The Acute Promyelocytic Leukemia–Specific PML–RARα Fusion Protein Inhibits Differentiation and Promotes Survival of Myeloid Precursor Cells," *Cell* 74:423–431 (1993).

Grigoriev, et al., "A Triple Helix–forming Oligonucleotide–Intercalator Conjugate Acts as a Transcriptional Repressor via Inhibition of NF kB Binding to Interleukin–2 Receptor α–Regulatory Sequence,"*J. Biol. Chem.* 267:3389–3395 (1992).

*# Guerrier–Takada, et al., "The RNA Moiety of Ribonuclease P Is the Catalytic Subunit of the Enzyme," *Cell* 35:849–857 (1983).

*# Guerrier–Takada, et al., "Catalytic Activity of an RNA Molecule Prepared by Transcription In Vitro," *Science* 223:285–286 (1984).

*# Guerrier–Takada, et al., "Specific Interactions in RNA Enzyme–Substrate Complexes," *Science*, 246:1578–1584 (1989).

Guidotti, et al., "High–Level Hepatitis B Virus Replication in Transgenic Mice," *J. Virol.* 69(10):6158–6169 (1995).

Gupta, et al., "Compilation of small RNA sequences," *Nucleic Acids Res.* 19(suppl.):2073–2075 (1990).

Hall, et al., "Transcription Initiation of Eucaryotic Transfer RNA Genes," *Cell* 29:3–5 (1982).

*# Hansen, et al., "Physical mapping and nucleotide sequence of the mpA gene that encodes the protein component of ribonuclease P in *Escerichia coli,*" *Gene* 38(1 and 3):535 (1985).

Hartmann, et al., "Towards a new concept of gene inactivation: specific RNA cleavage by endogenous ribonuclease P," *Biotech. Annu. Rev.* 1:215–265 (1995).

Heidenreich, et al., "High Activity and Stability of Hammerhead Ribozymes Containing 2'-Modified Pyrimidine Nucleosides and Phosphorothioates," *J. Biol. Chem.* 269:2131–2138 (1994).

Heidenreich, et al., "Hammerhead Ribozyme–mediated Cleavage of the Long Terminal Repeat RNA of Human Immunodeficiency Virus Type 1," *J. Biol. Chem.,* 267(3):1904–1909 (1992).

Hoke, et al., "Effects of Phosphorothioate capping on antisense oligonucleotide stability, hybridization and antiviral efficacy versus herpes simplex virus infection," *Nucleic Acids Res.* 19(20):5743–5748 (1991).

Huang, et al., "Use of All–Trans Retinoic Acid in the Treatment of Acute Promyelocytic Leukemia," *Blood* 72(2):567–572 (1988).

Itakura, et al., "Synthesis and use of Synthetic Oligonucleotides," *Ann. Rev. Biochem.* 53:323–356 (1984).

Iyer, et al., "The Automated Synthesis of Sulfur–Containing Oligodeoxyribonucleotides Using 3H–1,2–Bethzodithiol–3–one 1, 1–Dioxide as a Sulfur–Transfer Reagent," *J. Org. Chem.* 55(15):4693–4699 (1990).

Johnson, et al., eds., *Drug Delivery Systems,* (Chichester, England: Ellis Horwood, Ltd. 1987) (Table of Contents only).

\* Johnston, et al., "Present Status and Future Prospects for HIV Therapies," *Science* 260:1286–1292 (1993).

\* Joyce, et al., "Amplification, Mutation, and Selection of Catalytic RNA," *Gene* 82:83–87 (1989).

Kakizuka, et al., "Chromosomal Translocation t(15;17) in Human Acute Promyelocytic Leukemia Fuses RARα with a Novel Putative Transcription Factor, PML," *Cell* 66:663–674 (1991).

Kazakov, et al., "Site–specific cleavage by metal ion cofactors and inhibitors of M1 RNA, the catalytic subunit of RNase P from *Escherichia coli,*" *Proc. Natl. Acad. Sci. USA* 88(20):9193–9197 (1991).

Kickhoefer, et al., "Vault Ribonucleoprotein Particles from Rat and Bullfrog Contain a Related Small RNA That is Transcribed by RNA Polymerase III," *J. Biol. Chem.* 268(11):7868–7873 (1993).

Kim, et al., "Preparation of Multivesicular liposomes," *Biochim. Biophys. Acta* 728:339–348 (1983).

Korba, et al., "Use of a standardized cell culture assay to assess activities of nucleoside analogs against hepatitis B virus replication," *Antiviral Res.* 19(1):55–70 (1992).

*# Kruger, et al., "Self–Splicing RNA: Autoexcision and Auto–cyclization of the Ribosomal RNA Intervening Sequence of Tetrahymera," *Cell* 31(1):147–157 (1982).

Kunkel, et al., "Transcription of a human U6 small nuclear RNA gene in vivo withstands deletion of intragenic sequences but not of an upstream TATATA box," *Nucleic Acids Res.* 17(18):7371–7379 (1989).

Kunkel, et al., "U6 small nuclear RNA is transcribed by RNA polymerase III," *Proc. Natl. Acad. Sci. USA* 83(22):8575–8579 (1987).

Lanotte, et al., NB4, a Maturation Inducible Cell Line with t(15;17) Marker Isolated From a Human Acute Promyelocytic Leukemia (M3), *Blood* 77(5):1080–1086 (1991).

*# Lawrence, et al., "Site–Directed Mutagenesis of M1 RNA Subunit of *Escherichia coli* Ribonuclease P," *J. Mol Biol,* 191:163–175 (1986).

*# Lee, et al., "Partial Characterization of an RNA Component That Copurifies with *Saccharomyces cerevisiae* RNase P," *Molecular and Cellular Biology* 9(6):2536–2543 (1989).

Lee, et al., "Recognition of liposomes by cells: in vitro binding and endocytosis mediated by specific lipid headgroups and surface charge density," *Biochim. Biophys. Acta.* 1103:185–197 (1992).

Leeds, et al., "Quantitation of Phosphorothioate Oligonucleotides in Human Plasma," *Anal Biochem.* 235(1):36–43 (1996).

Lesnik, et al., "Oligodeoxynucleotides Containing 2'–O–Modified Adenosine: Synthesis and Effects on Stability of DNA:RNA Duplexes," *Biochemistry* 32(30):7832–7838 (1993).

*# Li, et al., "Targeted cleavage of mRNA in vitro by RNase P from *Escherichia coli,*" *Proc. Natl. Acad.* 89:3185–3189 (1992).

Liu, et al., "Role of liposome size and RES blockade in controlling biodistribution and tumor uptake of $GM_1$–containing liposomes," *Biochim. Biophys. Acta,* 1104:95–101 (1992).

Ma, et al., "Evaluation of modified oligoribonucleotide analogues as external guide sequences for inducing cleavage of HBV RNA by RNase P," abstract Keystone Symposium *On Ribozytmes: Basic Science and Therapeutic Applications,* Breckenridge Colorado, USA, Jan. 15–21, 1995 Journal of Cellular Biochemistry Supplement 0 (19A) p. 211.

Maher, et al., "Inhibition of DNA Binding Proteins by Oligonucleotide–Directed Triple Helix Formation," *Science* 245:725–730 (1989).

Matteucci, et al., "In pursuit of antisense," *Nature* 384(supp)(6604):20–22 (1996).

*# McClain, et al., "Model Substrate for an RNA Enzyme," *Science* 238:527–530 (1987).

Miller, et al., "Reverse transcription polymerase chain reaction for the rearranged retinoic acid receptor α clarifies diagnosis and detects minimal residual disease in acute promyelocytic leukemia," *Proc. Natl. Acad. Sci. USA* 89:2694–2698 (1992).

Milligan, et al., "Oligoribonucleotide synthesis using T7 RNA polymerase and synthetic DNA templates," *Nucl. Acids Res.* 15:8783–8798 (1987).

Milligan, et al., "Current Concepts in Antisense Drug Design," *J. Med. Chem.* 36(14):1923–1936 (1993).

*# Mills, et al., "Q βReplicase: Mapping the Functional Domains of an RNA–Dependent RNA Polymerase," *J. Molecular Biology* 205:751–764. (1988).

Monia, et al., "Evaluation of 2'–Modified Oligonucleotides Containing 2'–Deoxy Gaps as Antisense Inhibitors of Gene Expression," *J. Biol. Chem.* 268(19):14514–14522 (1993).

Mosmann, et al., "Rapid Colorimetric Assay for Cellular Growth and Survival: Application to Proliferation and Cytotoxicity Assays," *Journal of Immunological Methods* 65(1 and 2):55–63 (1983).

Mulligan, "The Basic Science of Gene Therapy," *Science,* 260:926–932 (1993).

Narang, et al., "Chemical Synthesis of Deoxyoligonucleotides by the Modified Triester Method," *Methods Enzymol.* 65:610–620 (1980).

Nielsen, et al., "Transcription of human 5S rRNA genets is influenced by an upstream DNA sequence," *Nucleic Acid Res.* 21(16):3631–3636 (1993).

Noonberg, et al., "In vivo generation of highly abundant sequence–specific oligonucleotides for antisense and triplex gene regulation," *Nucleic Acids Res.* 22(14):2830–2836 (1995).

Offensperger, et al., "In vivo inhibition of duck hepatitis B virus replication and gene expression by phosphorothioate modified antisense oligodeoxynucleotides" *EMBO J.* 12(3):1257–1262(1993).

Ogilvie, et al., "Total chemical synthesis of a 77–nucleotide––long RNA sequence having methionine–acceptance activity," *Proc. Natl. Acad. Sci. USA* 85(16):5764–5768 (1988).

Orson, et al., "Oligonucleotide inhibition of IL2Rα mRNA transcription by promoter region collinear triplex formation in lymphocytes," *Nucl. Acids Res.* 19(12):3435–3441 (1991).

Ortigao, et al., "Solid–phase introduction and intracellular photoinduced reaction of a water–soluble meso–tetracarboxyporphine conjugated to an antisense oligodeoxyribonucleotide," *Biochimie* 75:29–34 (1993).

*# Pace, et al., "Phylogenetic Comparative Analysis and the Secondary Structure of Ribonuclease P RNA—A Review," *Gene* 82:65–75 (1989).

*# Roizman, et al., "The Structure and Isomerization of Herpes Simplex Virus Genomes," *Cell*, 16(3):481–494 (1979).

Romero, et al., "A Conserved Secondary Structure for Telomerase RNA," *Cell* 67(2):343–353 (1991).

*# Rossi, et al., *J. Cell Biol.*, (Supp. 14A, D428) (1990).

Rossi, et al., "Exploring the Use of Antisense, Enzymatic RNA Molecules (Ribozymes) as Therapeutic Agents," *Antisense Res. Dev.* 1:285–288 (1991).

Sambrook, et al., *Molecular Cloning: A Laboratory Manual*, Second Edition, pp. 7.71–7.78 (Cold Spring Harbor Laboratory Press, 1989).

* Sampson, et al., *Quant. Biol.*, (Cold Spring Harbor Symp.) 52:267–275 (1987).

Sarin, et al., "Inhibition of acquired immunodeficiency syndrome virus by oligodeoxynucleoside methylphosphonates," *Proc. Natl. Acad. Sci. USA* 85(20):7448–7794 (1989).

*# Sarver, et al., "Ribozymes as Potential Anti–HIV–1 Therapeutic Agents," *Science* 247:1222–1225 (1990).

Scaringe, et al., "Chemical synthesis of biologically active oligoribonucleotides using β–cyanoethyl protected ribonuleoside phosphoramidites," *Nucleic Acids Research*, 18(18):5433–5441 (1990).

Seela, et al., "Oligodeoxyribonucleotides containing 1,3–propanediol as nucleoside substitute," *Nucleic Acids Res.* 15(7):3113–3129 (1987).

Sells, et al., "Production of hepatitis B virus particles in Hep G2 cells transfected with cloned hepatitis B virus DNA," *Proc. Natl. Acad. Sci. USA* 84(4):1005–1009 (1987).

*# Sharmeen, et al., "Antigenomic RNA of Human Hepatitis Delta Virus Can Undergo Self–Cleavage," *J. Virol.* 62(8):2674–2679 (1988).

Shaw, et al., "Modified deoxyoligonucleotides stable to exounclease degradation in serum," *Nucleic Acids Res.* 19(4):747–750 (1991).

Sinha, et al, "Labile exocyclic amine protection of nucleosides in DNA, RNA and oligonucleotide analog synthesis facilitating N–deacylation, minimizing depurination and chain degradation," *Biochimie* 75(1/2) 13–23 (1993).

Sproat, "An Efficient Method for the Isolation and Purification of Oligoribonucleotides," *Nucleosides & Nucleotides* 14:255–273 (1995).

*# Surratt, et al., "Processing of a Synthetic tRNA Precursor Model by *E. Coli* RNase P and M1 RNA," *Molecular Biology of RNA*, 79–88 (Alan R. Liss, Inc, 1989).

Symons, "Ribozymes" Current Opinion in Structural Biology, 4(3):322–330 (1994).

Symons, "Small Catalytic RNAs," *Annu. Rev. Biochem.* 61:641–671 (1992).

Thierry, et al., "Intracellular availability of unmodified, phosphorothioated and liposomally encapsulated oligodeoxynucleotides for antisense activity," *Nucl. Acids Res.* 20(21):5691–5698 (1992).

Thompson, et al., "Improved accumulation and activity of ribozymes expressed from a tRNA–based RNA polymerase III promoter," *Nucleic Acids Res.* 23(12):2259–2268 (1995).

Thurlow, et al., "Nucleotides in precursor tRNAs that are required intact for catalysis by RNase P RNAs," *Nucleic Acids Res.* 19(4):885–891 (1991).

*# Tuerk, et al., "Systematic Evolution of Ligands by Exponential Enrichment: RNA Ligands to Bacteriophage T4 DNA Polymerase," *Science* 249:505–510 (1990).

*# Uhlenbeck, *Nature*, 324:429–433 (1987).

Usman, et al., "Chemical modification of hammerhead ribozymes: activity and nuclease resistance" *Nucleic Acids Research Symposium Series* 31:163–164 (1994).

*# Wagner, et al., "Nucleotide sequence of the thymidine kinase gene of herpes simplex virus type 1," *Pruc. Natl. Acad. Sci.* 78(3):1441–1445 (1981).

Wang, et al., "Highly Efficient DNA Delivery Mediated by pH–Sensitive Immunoliposomes," *Biochem.* 28:9508–9514 (1989).

Warrell, et al., "Acute Promyelocytic Leukemia," *New England J. Med.* 329(3):177–189 (1993).

Warrell, et al., "Ferentiation Therapy of Acute Promyelocytic Leukemia with Tretinoin (All–Trans–Retinoic Acid)," *New Engl. J. Med.* 324:1385–1393 (1991).

* Whitton, "Antisens Treatment of Viral Infection," *Adv. Vir. Res.*, 44:267–303 (1994).

*# Wigler, et al., "DNA–mediated transfer of the adenine phosphoribosyltransferase locus into mammalian cells," *Proc. Natl. Acad. Sci., USA* 76(3):1373–1376 (1979).

Wincott, et al., "Synthesis, deprotection, analysis and purification of RNA and ribozymes," *Nucleic Acids Res.* 23(14):2677–2684 (1995).

*# Wu, et al., "Reversible Cleavage and Ligation of Hepatitis Delta Virus RNA," *Science* 243:652–655 (1989).

Yates, et al., "Stable replication of plasmids derived from Epstein–Barr virus in various mammalian cells," *Nature* 313(6005):812–815 (1985).

*# Yuan, et al, "Targeted cleavage of mRNA by human RNase P," *Proc. Natl. Acad. Sci., USA* 89:8006–8010 (1992).

Yuan, et al., "Selection of Guide Sequences That Direct Efficient Cleavage of mRNA by Human Ribonuclease P," *Science*, 263:1269–1273 (1994).

Yuan, et al., "Substrate Recognition by Human RNase P: Identification of Small, Model Substrates for the Enzyme," *EMBO*, 14(1):159–168 (1995).

Zhu, et al., "Systemic Gene Expression After Intravenous DNA Delivery Into Adult Mice," *Science* 261:209–211 (1993).

Ares, et al., "Lethal arid temperature–sensitive mutations and their suppressors identify an essential structural element in U2 small nuclear RNA," *Genes and Development* 4(12a):2132–2145 (1990).

Bertrand, et al., "Facilitation of hammerhead ribozyme catalysis by the nucleocapsid protein of HIV–1 and the heterogeneous nuclear ribonucleoprotein A1," *EMBO J.* 13(12):2904–2912 (1994).

Climie, et al., "In Vivo and in Vitro Structural Analysis of the rplJ mRNA Leader of *Escherichia coli,*" *J. Biol. Chem.* 263(29):15166–15175 (1988).

Coetzee, et al., "*Escherichia coli* proteins, including ribosomal protein S12, facilitate in vitro splicing of phage T4 introns by acting as RNA chaperons," *Genes and Development* 8(13):1575–1588 (1994).

Danos, et al., "Safe and efficient generation of recombinant retroviruses with amphotropic and ecotropic host ranges," *Proc. Natl. Acad. Sci. USA* 85(17):6460–6464 (1988).

Ejercito, et al, "Characterization of Herpes Simplex Virus Strains Differing in their Effects on Social Behaviour of Infected Cells," *J. Gen. Virol.* 2(3):357–364 (1968).

Fields, et al., "Herpes Simplex Viruses and Their Replication," *Virology,* 2nd Edition, Chapter 65, pp. 1795–1841 (Raven Press, New York, 1990).

Frank, et al., "Rational Design of Self–Cleaving pre–tRNA–Ribonuclease P RNA Conjugates," *Biochemistry* 33(35):10800–10801 (1994).

Gold, et al., "Reconstitution of RNAase P Activity Using Inactive Subunits from *E. coli* and HeLa Cells," *Cell* 44(2):243–249 (1986).

Guerrier–Takada, et. al., "Reconstitution of enzymatic activity from fragments of M1 RNA," *Proc. Natl. Acad. Sci. USA* 89:1266–1270 (1992).

Hershlag, et al., "An RNA chaperon activity of non–specific RNA binding proteins in hammerhead ribozyme catalysis," *EMBO J.* 13(12):2913–2924 (1994).

Howett, "Characterization of mRNAs That Map in the Bg/II N Fragment of the Herpes Simplex Virus Type 2 Genome," *J. Virol.* 52(1):99–107 (1984).

Inoue, et al., "Secondary structure of the circular form of the Tetrahymena rRNA intervening sequence: A technique for RNA structure analysis using chemical probes and reverse transcriptase," *Proc. Natl. Acad. Sci. USA* 82(3):648–652 (1985).

James, et al., "The Secondary Structure of Ribonuclease P RNA, the Catalytic Element of a Ribonucleoprotein Enzyme," *Cell* 52(1):19–26 (1988).

Kikuchi, et al.,"Artificial self–cleaving molecules consisting of a tRNA precursor and the catalytic RNA and RNase P," *Nucleic Acids Res.* 21(20):4685–4689 (1993).

Liu, et al., "Site–Directed Mutagensis of a Nucleotide–Binding Domain in HSV–1 Thymidine Kinase: Effects on Catalytic Activity," *Virology* 163(2):638–642 (1988).

Liu, et al., "The Promoter, Transcriptional Unit, and Coding Sequences of Herpes Simplex Virus 1 Family 35 Proteins Are Contained within and in Frame with the $U_L26$ Open Reading Frame," *J. Virol.* 65(1):206–212 (1991).

Liu, et al., "The Yeast KEM1 Gene Encodes a Nuclease Specific for G4 Tetraplex DNA: Implication of In Vitro Functions for this Novel DNA Structure," *Cell* 77(7):1083–1100 (1994).

McMeoch, et al., "The Complete DNA Sequence of the Long Unique Region in the Genome of Herpes Simplex Virus Type 1," *J. Gen. Virol.* 69(7):1531–1574 (1988).

Miller, et al., "Improved Retroviral Vectors for Gene Transfer and Expression," *BioTechniques* 7(9):980–990 (1989).

Peattie, et al., "Chemical probes for higher–order structure in RNA," *Proc. Natl. Acad. Sci. USA* 77(8):4679–4682 (1980).

Reich, et al., "Role of the Protein Moiety of Ribonuclease P, a Ribonucleoprotein Enzyme," *Science* 239:178–181 (1988).

Smith, et al., "Multiple Magnesium Ions in the Ribonuclease P Reaction Mechanism," *Biochemistry* 32(20)5273–5281 (1993).

Stein, et al., "Antisense Oligonucleotides as Therapeutic Agents—Is the Bullet Really Magical?," *Science* 261:1004–1012 (1993).

Tsuchihashi, et al, "Protein Enhancement of Hammerhead Ribozymes Catalysis," *Science* 262:99–102 (1993).

Vioque, et al., "Protein–RNA Interactions in the RNase P Holoezyme from *Escherichia coli,*" *J. Mol. Biol.* 202(4):835–848 (1988).

EGS 104 + TK mRNA

EGS 109 + TK mRNA

EGS 112 + TK mRNA

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:1:

GAACAUUUUG AGGCAUUUCA GUCAGUUGGC CAAACUGAGC AGACUCUAAA        50

UCUGCNNNNN GAAGGUUCNN NNCCUUCAUG CCUCACCA        88

( 2 ) INFORMATION FOR SEQ ID NO:2:

( i ) SEQUENCE CHARACTERISTICS:
                ( A ) LENGTH: 61 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TAATACGACT CACTATAGAA CATTTGAGG CATTTCAGTC AGTTGGCCAA        50

ACTGAGCAGA C        61

( 2 ) INFORMATION FOR SEQ ID NO:3:

( i ) SEQUENCE CHARACTERISTICS:
                ( A ) LENGTH: 61 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TGGTGAGGCA TGAAGGNNNN GAACCTTCNN NNNGCAGATT TAGAGTCTGC        50

TCAGTTTGGC C        61

( 2 ) INFORMATION FOR SEQ ID NO:4:

( i ) SEQUENCE CHARACTERISTICS:
                ( A ) LENGTH: 99 base pairs
                ( B ) TYPE: nucleic acid
                ( C ) STRANDEDNESS: single
                ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:4:

GAAUACACGG AAUUGGUGGG GUUCCCGAGC GGCCAAAGGG AGCAGACUCU        50

AAAUCUGCCG UCAUCGACUU CGAAGGUUCG AAUCCUUCCC CCACUGCCA        99

( 2 ) INFORMATION FOR SEQ ID NO:5:

( i ) SEQUENCE CHARACTERISTICS:
                ( A ) LENGTH: 71 base pairs
                ( B ) TYPE: nucleic acid
                ( C ) STRANDEDNESS: single (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:5:

GCCAAAGGGA GCAGACUCUA AAUCUGCCGU CAUCGACUUC GAAGGUUCGA          50

AUCCUUCCCC CACCACCAUC A          71

(2) INFORMATION FOR SEQ ID NO:6:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:6:

GAAUACACGG AAUUGGUGGG GUUCCCGA          28

(2) INFORMATION FOR SEQ ID NO:7:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:7:

AUGGAACAUU UUGAGGCAUU UCAGUCAGUU UAA          33

(2) INFORMATION FOR SEQ ID NO:8:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:8:

GGCCAAACUG AGCAGACUCU AAAUCUGCCG UCAUCGACUU CGAAGGUUCG          50

AAUCCUUCAU GCCUCACCAU          70

(2) INFORMATION FOR SEQ ID NO:9:

(i) SEQUENCE CHARACTERISTICS:
    (A) LENGTH: 61 base pairs
    (B) TYPE: nucleic acid
    (C) STRANDEDNESS: single (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:9:

| GGCCAAACUG | AGCAGACUCU | AAAUCGCAAA | CGGAAGGUUC | GUGCCCUUCA | 50 |
|---|---|---|---|---|---|
| UGCCUCACCA | U | | | | 61 |

(2) INFORMATION FOR SEQ ID NO:10:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:10:

| GGCCAAACUG | ACGUCAUCGA | CUUCGAAGGU | UCGAAUCCUU | CAUGCCUCAC | 50 |
|---|---|---|---|---|---|
| CAU | | | | | 53 |

(2) INFORMATION FOR SEQ ID NO:11:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (vi) ORIGINAL SOURCE:
        (A) ORGANISM: Homo sapiens (x) PUBLICATION INFORMATION:
        (A) AUTHORS: Altman et al.
        (C) JOURNAL: Genomics
        (D) VOLUME: 18
        (F) PAGES: 418-422
        (G) DATE: 1993
        (K) RELEVANT RESIDUES IN SEQ ID NO:1: FROM 1 TO 341

(xi) SEQUENCE DESCRIPTION: SEQ ID NO:11:

| AUAGGGCGGA | GGGAAGCUCA | UCAGUGGGGC | CACGAGCUGA | GUGCGUCCUG | 50 |
|---|---|---|---|---|---|
| UCACUCCACU | CCCAUGUCCC | UUGGGAAGGU | CUGAGACUAG | GGCCAGAGGC | 100 |
| GGCCUAACA | GGGCUCUCCC | UGAGCUUCGG | GGAGGUGAGU | UCCCAGAGAA | 150 |
| CGGGGCUCCG | CGCGAGGUCA | GACUGGGCAG | GAGAUGCCGU | GGACCCCGCC | 200 |
| CUUCGGGGAG | GGGCCCGGCG | GAUGCCUCCU | UUGCCGGAGC | UUGGAACAGA | 250 |
| CUCACGGCCA | GCGAAGUGAG | UUCAAUGGCU | GAGGUGAGGU | ACCCCGCAGG | 300 |
| GGACCUCAUA | ACCCAAUUCA | GACUACUCUC | CUCCGCCCAU | U | 341 |

(2) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

GCCAAACTGA GCAGACTC
    18

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

GCGCGGTACC AAAAATGGTG AGGCATGAAG G
    31

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

GGCCGTAATA TCCAGCTGAA CGG
    23

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

TGGTGAGGCA TGAAGG
    16

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TAATACGACT CACTATAGGC CAACTGAGCA GAC 33

(2) INFORMATION FOR SEQ ID NO:17:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:17:

GGCCAAACUG AGCAGACUCU AAAUCGGCCC UUCGAAGGUU CGCCCCCUUC 50

AUGCCUCACC A 61

(2) INFORMATION FOR SEQ ID NO:18:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:18:

GGCCAAACUG AGCAGACUCU AAAUCUGCAC GAGAGAAGGU UCGUGCCCUU 50

CAUGCCUCAC CA 62

(2) INFORMATION FOR SEQ ID NO:19:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:19:

GGCCAAACUG AGCAGACUCU AAACUGGCCU AACGAAGGUU CGCCCCCUUC 50

AUGCCUCACC A 61

(2) INFORMATION FOR SEQ ID NO:20:

(i) SEQUENCE CHARACTERISTICS:
(A) LENGTH: 60 base pairs (B) TYPE: nucleic acid
(C) STRANDEDNESS: single
(D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:20:

GGCCAAACUG AGCAGACUCU AAAUUGCCCA ACGAAGGUUC ACCCCCUUCA    50

UGCCUCACCA    60

(2) INFORMATION FOR SEQ ID NO:21:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:21:

GGCCAAACUG AGCAGACUCC AAAUCCACCA AGAAGGUUCG UGCCCUUCAU    50

GCCUCACCA    59

(2) INFORMATION FOR SEQ ID NO:22:

(i) SEQUENCE CHARACTERISTICS:
    (A) LENGTH: 60 base pairs
    (B) TYPE: nucleic acid
    (C) STRANDEDNESS: single
    (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:22:

GGCCAAACUG AGCAGACUCU AAACUCCUCC CAGAAGGUUC GUGCCCUUCA    50

UGCCUCACCA    60

(2) INFORMATION FOR SEQ ID NO:23:

(i) SEQUENCE CHARACTERISTICS:
    (A) LENGTH: 61 base pairs
    (B) TYPE: nucleic acid
    (C) STRANDEDNESS: single
    (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:23:

GGCCAAACUG AGCAGACUCU AAAUCGGCCU ACGGAAGGUU CGCCCCCUUC    50

AUGCCUCACC A    61

( 2 ) INFORMATION FOR SEQ ID NO:24:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:24:

```
GGCCAAACUG AGCAGACGCU AAAUCACCC CGUGAAGGUU CGUCCCUUC          50
AUGCCUCACC A                                                  61
```

( 2 ) INFORMATION FOR SEQ ID NO:25:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:25:

```
GGCCAAACUG AGCAGACUCU AAAUUUGCCA CCAGAAGGUU CGCCCCUUC         50
AUGCCUCACC A                                                  61
```

( 2 ) INFORMATION FOR SEQ ID NO:26:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:26:

```
GGCCAAACUG AGCAGACUCA AAUCUGGCCA UUCGAAGGUU CGCCCCUUC         50
AUGCCUCACC A                                                  61
```

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:27:

```
GGCCAAACUG AGCAGACUCU AAAUCGCAGU GUGAAGGUUC GUGCCCUUCA        50
```

UGCCUCACCA 60

( 2 ) INFORMATION FOR SEQ ID NO:28:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:28:

GGCCAAACUG AGCAGACUCU AAAUCAGCGC GUGGAAGGUU CGUGCCUUC 50

AUGCCUCACC A 61

( 2 ) INFORMATION FOR SEQ ID NO:29:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:29:

GGCCAAACUG AGCAGACUCU AAAUCGGCCG CACGAAGGUU CGCCCCUUC 50

AUGCCUCACC A 61

( 2 ) INFORMATION FOR SEQ ID NO:30:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:30:

GGCCAAACUG AGCAGACACU AAAUUUGCAC GAGGAAGGUU CGCCCCUUC 50

AUGCCUCACC A 61

( 2 ) INFORMATION FOR SEQ ID NO:31:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:31:

GGCCAAACUG AGCAGACCCU AAAUCUGCCC CCGGAAGGUU CGUGCCCUUC                     50

AUGCCUCACC A                                                               61

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

GCCAAACTGA CGTCATCGAC TTCG                                                 24

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

AACAGCTATG ACCATG                                                          16

( 2 ) INFORMATION FOR SEQ ID NO:34:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

GTAATACGAC TCACTATAGG CCAAACTGAG CAGACTCTAA ATCTGCAAAC                     50

GGAAGGTTC                                                                  59

( 2 ) INFORMATION FOR SEQ ID NO:35:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:35:

ATGGCTTCGT ACCCCTGCCA TCAACACGCG TCTGCGTTCG ACCAGGC  47

( 2 ) INFORMATION FOR SEQ ID NO:36:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:36:

GGTTAACGTC GGACAGACTC TAAATCTGTT GCGGTCTCCG CGCGCAGGTT  50

CAAATCCTGC CGCAGACGTT T  71

( 2 ) INFORMATION FOR SEQ ID NO:37:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:37:

GGTTAACGTC GGACAGACTC TAAATCTGTT GCGGTCTCCG CGCGCAGGTT  50

GAAATCCTGC CGCAGACGTT T  71

( 2 ) INFORMATION FOR SEQ ID NO:38:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:38:

GGTTAACGTC GGTGCGGTCT CCGCGCGCAG GTTCAAATCC TGCCGCAGAC  50

GTTT  54

( 2 ) INFORMATION FOR SEQ ID NO:39:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:39:

| GGCCAAACUG | AGCAGACUCU | AAAUCUGCAA | ACGGAAGGUU | CGUGCCCUUC | 50 |
| AUGCCUCACC | AU | | | | 62 |

( 2 ) INFORMATION FOR SEQ ID NO:40:

( i ) SEQUENCE CHARACTERISTICS:
        ( A ) LENGTH: 377 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:40:

| GAAGCUGACC | AGACAGUCGC | CGCUUCGUCG | UCGUCCUCUU | CGGGGGAGAC | 50 |
| GGGCGGAGGG | GAGGAAAGUC | CGGGCUCCAU | AGGGCAGGGU | GCCAGGUAAC | 100 |
| GCCUGGGGGG | GAAACCCACG | ACCAGUGCAA | CAGAGAGCAA | ACCGCCGAUG | 150 |
| GCCCGCGCAA | GCGGGAUCAG | GUAAGGGUGA | AAGGGUGCGG | UAAGAGCGCA | 200 |
| CCGCGCGGCU | GGUAACAGUC | CGUGGCACGG | UAAACUCCAC | CCGGAGCAAG | 250 |
| GCCAAAUAGG | GGUUCAUAAG | GUACGGCCCG | UACUGAACCC | GGGUAGGCUG | 300 |
| CUUGAGCCAG | UGAGCGAUUG | CUGGCCUAGA | UGAAUGACUG | UCCACGACAG | 350 |
| AACCCGGCUU | AUCGGUCAGU | UUCACCU | | | 377 |

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:41:

| TAATACGACT | CACTATAG | | | | 18 |

( 2 ) INFORMATION FOR SEQ ID NO:42:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:42:

| CGCAGACGGT | CCTATAGTGA | GTCGTATTA | | | 29 |

( 2 ) INFORMATION FOR SEQ ID NO:43:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:43:

```
ACCGCGCAGC CTGGTCGAAC GCAGACGCGT GTTGATGGCA GGGGTCTATA            50

GTGAGTCGTA TTA                                                   63
```

( 2 ) INFORMATION FOR SEQ ID NO:44:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:44:

```
ATGCCTCGGT CCTATAGTGA GTCGTATTA                                  29
```

( 2 ) INFORMATION FOR SEQ ID NO:45:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:45:

```
GTGGTGTCTG CGTTCGACCA GCTATGACCA TG                              32
```

( 2 ) INFORMATION FOR SEQ ID NO:46:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:46:

```
GTGGTGTCTG CGTTCGACCA GTATGACCAT G                               31
```

( 2 ) INFORMATION FOR SEQ ID NO:47:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:47:

GTGGTGTCTG CGTTCGACTA TGACCATG                       28

(2) INFORMATION FOR SEQ ID NO:48:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:48:

GTGGTGTCTG CGTTCTATGA CCATG                          25

(2) INFORMATION FOR SEQ ID NO:49:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:49:

GTGGTGTCTG TATGACCATG                                20

(2) INFORMATION FOR SEQ ID NO:50:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:50:

GTGGTGAGGC ATTTCAGTTA TGACCATG                       28

(2) INFORMATION FOR SEQ ID NO:51:

(i) SEQUENCE CHARACTERISTICS:
    (A) LENGTH: 12 base pairs
    (B) TYPE: nucleic acid ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:51:

AUGCCUCACC AC 12

( 2 ) INFORMATION FOR SEQ ID NO:52:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:52:

CGCAGACACC AC 12

( 2 ) INFORMATION FOR SEQ ID NO:53:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:53:

GGACCGAGGC AU 12

( 2 ) INFORMATION FOR SEQ ID NO:54:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:54:

GGACCGUCUG CG 12

( 2 ) INFORMATION FOR SEQ ID NO:55:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:55:

GUCUGCGUUC GA                                                                                                           1 2

( 2 ) INFORMATION FOR SEQ ID NO:56:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:56:

GAGGCAUUUC AGU                                                                                                          1 3

( 2 ) INFORMATION FOR SEQ ID NO:57:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:57:

GACCCCTGCC ATCAACACGC GTCTGCGTTC GACCAGGCTG CGCGGT                                                                      4 6

( 2 ) INFORMATION FOR SEQ ID NO:58:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:58:

AGCCUGGUCG AACGCAGACA CCAAAA                                                                                            2 6

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:59:

AGCCUGGUCG AACGCAGACA CCAC 24

( 2 ) INFORMATION FOR SEQ ID NO:60:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:60:

CUGGUCGAAC GCAGACACCA C 21

( 2 ) INFORMATION FOR SEQ ID NO:61:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:61:

GUCGAACGCA GACACCAC 18

( 2 ) INFORMATION FOR SEQ ID NO:62:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:62:

GAACGCAGAC ACCAC 15

( 2 ) INFORMATION FOR SEQ ID NO:63:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:63:

CAGACACCAC 10

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:64:

GUCGAACGCA GACACCAC     18

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:65:

CUGGUCGAAC GCAGACACCA C     21

TARGETED CLEAVAGE OF RNA USING RIBONUCLEASE P TARGETING AND CLEAVAGE SEQUENCES

This application is a continuation-in-part of U.S. Ser. No. 08/207,547, entitled "Targeted Cleavage of RNA Using Eukaryotic Ribonuclease P and External Guide Sequence" filed Mar. 7, 1994, and a continuation-in-part of U.S. Ser. No. 08/215,082, entitled "Targeted Cleavage of RNA Using Eukaryotic Ribonuclease P and External Guide Sequence" filed Mar. 18, 1994. This is a national stage application under 35 U.S.C. § 371 of PCT/US95/02816.

BACKGROUND OF THE INVENTION

This invention is in the general area of genetic engineering of nucleic acid sequences, especially chemically modified external guide sequences and catalytic RNA sequences linked to guide sequences.

There are several classes of ribozymes now known which are involved in the cleavage and/or ligation of RNA chains. A ribozyme is defined as an enzyme which is made of RNA, most of which work on RNA substrates. Ribozymes have been known since 1982, when Cech and colleagues (Cell 31: 147–157) showed that a ribosomal RNA precursor in Tetrahymena, a unicellular eukaryote, undergoes cleavage catalyzed by elements in the RNA sequence to be removed during the conversion of the rRNA precursor into mature rRNA. Another class of ribozyme, discovered in 1983, was the first to be shown to work in trans, that is, to work under conditions where the ribozyme is built into one RNA chain while the substrate to be cleaved is a second, separate RNA chain. This ribozyme, called M1 RNA, was characterized in 1983 by Altman and colleagues as responsible for the cleavage which forms mature 5' ends of all transfer RNAs (tRNAs) in *E. coli*. Analogous RNA-containing enzymes concerned with tRNA synthesis have since been found in all cells in which they have been sought, including a number of human cell lines, though the relevant eukaryotic RNAs have not yet been shown to be catalytic by themselves in vitro.

The discovery and characterization of this catalytic RNA is reviewed by Sidney Altman, in "Ribonuclease P: An Enzyme with a Catalytic RNA Subunit" in *Adv. Enzymol.* 62: 1–36 (1989). The activity was first isolated from *E. coli* extracts, and subsequently determined to be a ribonucleoprotein having two components, an RNA component called M1 and a protein component called C5. The RNA cleaved substrates in a true enzymatic reaction, as measured using Michaelis-Menten kinetics. M1 was determined to be solely responsible for substrate recognition and C5 was determined to alter $k_{cat}$ but not $K_M$, as reported by Guerrier-Takada et al., Cell 35: 849 (1983) and McClain et al., Science 238: 527 (1987). Sequencing showed that M1 RNA is 377 nucleotides long, $M_r$ approximately 125,000, and that the protein consists of 119 amino acids, $M_r$ approximately 13,800, as reported by Hansen et al., Gene 38: 535 (1987).

Cleavage of precursor tRNA molecules by the RNA component of eubacterial RNase P is described by Guerrier-Takada et al., Cell 35, 849 (1983) and reviewed by Altman, *Adv. Enzymol.* 62:1 (1989).

U.S. Pat. No. 5,168,053 entitled "Cleavage Of Targeted RNA By RNase P" to Altman et al., discloses that it is possible to target any RNA molecule for cleavage by bacterial RNase P by forming a nucleotide sequence part of which is complementary to a targeted site and which includes a terminal 3'-NCCA, wherein the sequence is designed to hybridize to the targeted RNA so that the bacterial RNase P cleaves the substrate at the hybrid base-paired region. Specificity is determined by the complementary sequence. The sequence is preferably ten to fifteen nucleotides in length and may contain non-complementary nucleotides to the extent this does not interfere with formation of several base pairs by the complementary sequence which is followed by NCCA at the 3' end.

As described in WO 92/03566 to Yale University, ribonuclease P (RNase P) from *E. coli* can cleave oligoribonucleotides that are found in hydrogen-bonded complexes that resemble the aminoacyl stem and include the 5' leader sequence of tRNA precursors, —NCAA. Human RNase P cannot cleave in vitro the 5' proximal oligoribonucleotide in the simple complexes cleaved by RNase P from *E. coli*, but can do so when the 3' proximal oligoribonucleotide is bound to an external guide sequence (EGS) to form a structure resembling portions of a tRNA molecule. The EGS can include a complementary sequence to a target substrate of at least eleven nucleotides, seven bases which hydrogen bond to the targeted sequence to form a structure akin to the aminoacyl acceptor stem of a precursor tRNA, and four nucleotides which base pair with the targeted sequence to form a structure akin to the dihydroxyuracil stem. WO 92/03566 does not disclose EGS for prokaryotic RNase P with fewer than seven complementary nucleotides.

WO 93/22434 to Yale University discloses an EGS for human RNase P. As described in WO 93/22434, an EGS for human RNase P consists of a sequence which, when in a complex with the target substrate molecule, forms a secondary structure resembling that of a tRNA cloverleaf, or a substantial part of it, and that results in cleavage of the target RNA by RNase P. The sequence of the EGS of WO 93/22434 is derived from any tRNA except that the D stem and aminoacyl stem are altered to be complementary to the target substrate sequence. WO 93/22434 also discloses EGS with either the anticodon loop and stem or the extra loop deleted, and EGS where the sequence of the T loop and stem are changed. WO 93/22434 does not disclose eukaryotic EGS comprising only a region complementary to the target RNA and a region forming a structure similar to only the T stem and loop of tRNA. Neither WO 92/03566 nor WO 93/22434 discloses EGS having chemically modified nucleotides.

It is therefore an object of the present invention to provide methods and compositions for specifically cleaving targeted RNA sequences using linked catalytic RNA and minimal guide sequences.

It is another object of the present invention to provide chemically modified external guide sequences for RNase P with enhanced resistance to nuclease degradation.

It is another object of the present invention to provide a method for selecting external guide sequences, and linked catalytic RNA and guide sequences, that cleave a target RNA with increased efficiency.

It is a further object of the present invention to provide methods and compositions for specifically cleaving RNA, both in vitro and in vivo within eukaryotic cells, for the treatment of disease conditions which involve RNA transcription or translation, such as diseases caused by RNA and DNA viruses and expression of excessive or pathogenic proteins from mRNA, or of excessive or pathogenic RNA, itself.

SUMMARY OF THE INVENTION

Any RNA can be targeted for cleavage by RNase P, using a suitably designed oligonucleotide ("external guide sequence") to form a hybrid with the target RNA, thereby creating a substrate targeted for cleavage by RNase P. The EGSs contain sequences which are complementary to the target RNA and which forms secondary and tertiary structure akin to portions of a tRNA molecule. A eukaryotic EGS must contain at least seven nucleotides which base pair with the target sequence 3' to the intended cleavage site to form a structure like the amino acyl acceptor stem, nucleotides which base pair to form a stem and loop structure similar to the T stem and loop, followed by at least three nucleotides that base pair with the target sequence to form a structure like the dihydroxyuracil stem. The EGS can be made more resistant to nuclease degradation by including chemically modified nucleotides or nucleotide linkages.

The external guide sequence and the RNase P catalytic RNA can be used together as separate molecules. Alternatively, the two sequences can be combined into a single oligonucleotide molecule possessing both targeting and catalytic functions. Such a combined oligonucleotide, termed an RNase P internal guide sequence (RIGS), increases the kinetic efficiency of cleavage by reducing the number of reactants and by keeping the targeting and catalytic elements in close proximity. Chemically modifying the nucleotides and phosphate linkages of EGS molecules and RIGS molecules make the oligonucleotides more resistant to nuclease degradation.

Methods are also disclosed to select RIGS molecules and EGS molecules having increased substrate affinity and utility in vivo to cleave or target cleavage of a selected RNA, thus preventing expression of the function of the target RNA. The methods and compositions should be useful to prevent the expression of disease- or disorder-causing genes in vivo.

As described in the examples, an RIGS was constructed by linking a guide sequence to M1 RNA (M1GS RNA). M1GS RNA can act as a sequence-specific endonuclease and can cleave target RNAs that base pair with the guide sequence just as group I introns do. A custom-designed M1GS RNA cleaves the mRNA that encodes thymidine kinase (TK) of human herpes simplex virus 1 (HSV-1) in vitro. When this M1GS RNA is expressed in mammalian cells in tissue culture, it reduces the level of expression of TK by decreasing the amount of the target TK mRNA.

BRIEF DESCRIPTION OF THE DRAWINGS

In FIGS. 4A, 4B and 4C solid arrowheads denote the sites of cleavage by RNase T1, and arrows denote sites of cleavage by RNase T2. In FIGS. 4D, 4E and 4F, sites of cleavage by cobra venom nuclease are indicated by solid arrows.

FIG. 6A is an EGS (Sequence ID No. 36) forming an aminoacyl acceptor stem, T loop and stem, variable loop and stem, anticodon loop and stem, and D stem. FIG. 6B is an EGS (Sequence ID No. 37) wherein a G in the T loop is substituted for a C in the EGS of FIG. 6A. FIG. 6C is an EGS (Sequence ID No. 38) where the anticodon loop and stem of the EGS of FIG. 6A is deleted.

Figure 1:
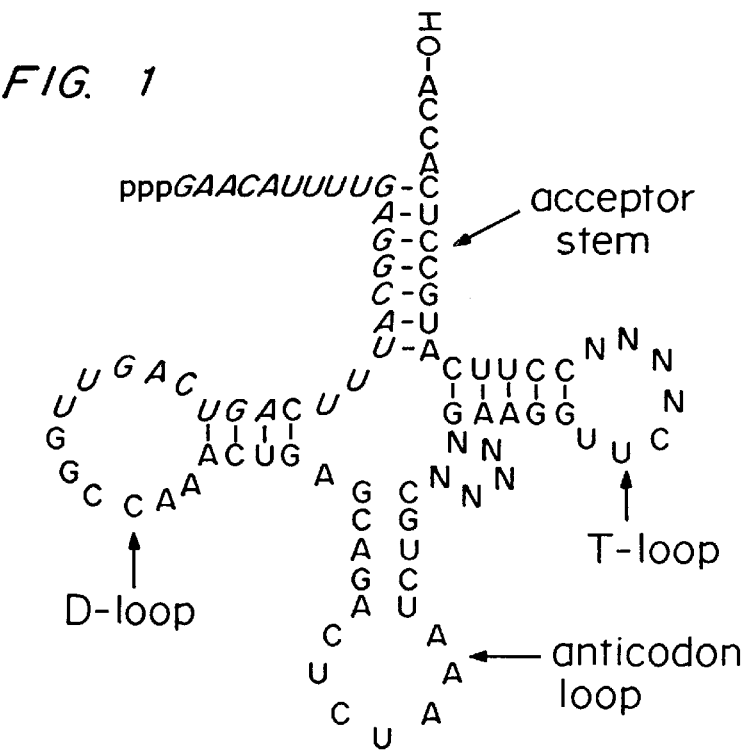
FIG. 1 is the proposed secondary structure of the chimeric substrate used in the selection procedure (Sequence ID No. 1). The italicized sequence is from CAT mRNA and the remaining sequence, aside from changes made to assure hydrogen bonding specifically to CAT mRNA, is based on the sequence of $E.\ coli$ tRNA$^{Tyr}$. The nine nucleotides that were randomized are each indicated by N. Some of the EGS analogs for various parts of a tRNA are also depicted: acceptor stem, T loop, anticodon loop, and D-loop.

Solid bars: TK mRNA; open bars; TK protein.

DETAILED DESCRIPTION OF THE INVENTION

Guide Sequence

As used herein, a guide sequence (GS) is an oligonucleotide that targets a substrate RNA molecule for cleavage by a catalytic RNA having the activity of RNase P catalytic RNA. A guide sequence may be a separate molecule, termed an external guide sequence, or combined in a single molecule with catalytic RNA. Such a combined molecule is referred to herein as an RNase P internal guide sequence (RIGS).

A. Eukaryotic RNase P Targeting Sequence

A guide sequence for human RNase P consists of a sequence which, when in a complex with the target substrate molecule, forms a secondary structure resembling that of a tRNA cloverleaf or a part of it.

As used herein, the term "resembling a precursor tRNA" means a complex formed by the GS with target RNA substrate to resemble a sufficient portion of the tRNA secondary and tertiary structure to result in cleavage of the target RNA by RNase P. The sequence of the GS can be derived from any tRNA except that the D stem and aminoacyl stem have to be altered to be complementary to the target substrate sequence. These altered stems are referred to as recognition arms. The recognition arm corresponding to the aminoacyl stem is referred to as the A recognition arm and the recognition arm corresponding to the D stem is referred to as the D recognition arm. The remaining portion of the guide sequence, which is required to cause RNase P catalytic RNA to interact with the GS/target sequence complex, is herein referred to as RNase P binding sequence. The presence of a 3'-CCA on an EGS enhances the efficiency of in vitro reaction with the human RNase P by about 35%. The anticodon loop and stem and extra loop can separately be deleted and the sequence of the T loop and stem can be changed without decreasing the usefulness of the guide sequence and, in the case of the anticodon stem and loop deletion, increases the efficiency of the reaction by about ten fold. Changes in other parts of an EGS can increase its efficiency about one hundred fold.

The desired secondary structure is determined using conventional Watson-Crick base pairing schemes to form a structure resembling a tRNA, that is, having structure as described below. The specific sequence of the hydrogen bonded regions is not as critical, as long as the desired structure is formed. All tRNAs, including tRNAs from a wide variety of bacteria and eukaryotes, conform to the same general secondary structure. This is typically written in the form of a cloverleaf, maintained by hydrogen-bonded base pairing between short complementary regions. The four major arms are named for their 10 structure or function: The acceptor arm consists of a 3' terminal $CCA_{OH}$ plus a variable fourth nucleotide extending beyond the stem formed by base-pairing the 5' and 3' segments of the molecule. The other arms consist of base-paired stems and unpaired loops. The "T" arm is named for the presence of the ribothymidine nucleotide and contains seven unpaired bases in the loop. The anticodon arm always contains the anticodon triplet in the center of the loop and consists of seven unpaired bases.

The D arm is named for the presence of the base dihydrouridine in the loop, another of the chemically modified bases in tRNA, and includes between eight and twelve unpaired bases. Positions are numbered from 5' to 3' according to the most common tRNA structure, which has 76 residues. The overall range of tRNA lengths is from 74 to 95 bases. The variation in length is caused by differences in the structure of two of the arms, the D arm and the extra or variable arm, which lies between the T and anticodon arms, which can contain between three and five bases, or between 13 and 21 bases with a stem of about five bases. The base pairing that maintains the secondary structure is virtually invariant: there are always seven base pairs in the acceptor stem, five in the T arm, five in the anticodon arm, and three or four in the D arm.

As used herein, a hybrid structure, consisting of an EGS hydrogen bonded to an RNA substrate, having secondary structure resembling a precursor tRNA under conditions promoting cleavage by RNase P of the substrate at the nucleotide at the 5' end of the base-paired region, preferably includes a D stem, an aminoacyl stem, and a T loop and stem, where the sequence of the latter may be changed compared to the sequence and detailed structure found in the parent molecule.

A few nucleotides are always found in the same positions in 90 to 95% of tRNAs, with some additional nucleotides being semiconserved or semivariant. This is not an absolute requirement in the GS, as long as the sequence is complementary to the target and forms the secondary structure characteristic of the tRNA. In fact, the sequence forming the aminoacyl stem and D loop and stem are changed in the GS to be complementary to the target RNA.

The base paired double-helical stems of the secondary structure are maintained in the tertiary structure, creating two double helices at right angles to each other. The acceptor stem and the T stem form one continuous double helix with a single gap; the D stem and the anticodon stem form another continuous double helix, also with a gap. Many of the invariant and semi-invariant bases are involved in the tertiary structure.

The complementary sequences will generally consist of eleven nucleotides, or, under certain conditions may consist of as few as seven nucleotides, in two blocks which base pair with the target sequence and which are separated by two unpaired nucleotides in the target sequence, preferably UU, wherein the two blocks are complementary to a sequence 3' to the site targeted for cleavage.

B. Prokaryotic RNase P Targeting Sequence

The requirements for a GS functional with prokaryotic RNase P are less stringent than those for a eukaryotic GS. The critical elements of a prokaryotic GS are (1) nucleotide sequence which specifically binds to the targeted RNA substrate to produce a short sequence of base pairs 3' to the cleavage site on the substrate RNA and (2) a terminal 3'-NCCA, where N is any nucleotide, preferably a purine. The sequence generally has no fewer than four, and more usually six to fifteen, nucleotides complementary to the targeted RNA. It is not critical that all nucleotides be complementary, although the efficiency of the reaction will vary with the degree of complementarity. The rate of cleavage is dependent on the RNase P, the secondary structure of the hybrid substrate, which includes the targeted RNA and the presence of the 3'-NCCA in the hybrid substrate.

Ribonuclease P

Ribonuclease P is an enzyme consisting of protein and RNA subunits that cleaves tRNA precursors to generate the 5' termini of tRNAs. This essential enzymatic activity has been found in all cell types examined, both prokaryotic and eukaryotic. During the studies on recognition of substrate by RNase P, it was found that *E. coli* RNase P can cleave synthetic tRNA-related substrates that lack certain domains, specifically, the D, T and anticodon stems and loops, of the normal tRNA structure. A half-turn of an RNA helix and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as a "guide sequence" because it identifies the site of cleavage in the 5' proximal region through a base-paired region.

RNase P from *E. coli* and human cells have similar but not identical biochemical properties. Their RNA components have similar secondary structures. However, the substrate range of human RNase P is much narrower than that of the *E. coli* enzyme. For example, although *E. coli* RNase P can cleave a synthetic tRNA-related substrate that lacks three specific domains of the normal tRNA structure, the human enzyme and the structurally similar enzyme from the yeast, *S. cerevisiae,* cannot cleave the same substrate. However, the *E. coli* RNase P can cleave a synthetic tRNA-related substrate that is also cleaved by the human RNase P. Altman et al., *Genomics* 18: 419422 (1993), describes several mammalian RNase P catalytic RNAs and identifies common features and differences.

As used herein, unless otherwise specified, RNase P refers to the RNase P in the cell in which the RNA to be cleaved is located, whether endogenous, added to the cell, or as used in vitro. Many of the techniques described herein are known to those skilled in the art, as are methods for making, and sources of, reagents. The teachings of any references cited herein with respect to methods and reagents are specifically incorporated herein, as well as for the purpose of demonstrating the scope and level of skill in the art.

It is not necessary to provide RNase P activity if the cleavage is to occur in bacterial cells or intracellularly in the nucleus since all eukaryotic cells contain RNase P in their nuclei. RNase P must be supplied if cleavage is to occur in the cytoplasm of eukaryotic cells. As used herein for ease of convenience, RNase P refers to the ribonucleoprotein consisting of prokaryotic or eukaryotic analogues of the *E. coli* C5 protein and M1 RNA, regardless of source, whether isolated, or produced by chemical synthesis. The RNA subunit of RNase P also can be transcribed from a gene. The eukaryotic RNase P RNA subunit is referred to as H1 RNA. The RNA subunit need not necessarily manifest catalytic activity in the absence of protein subunits in vitro.

A. Endogenous RNase P

Figure 8:
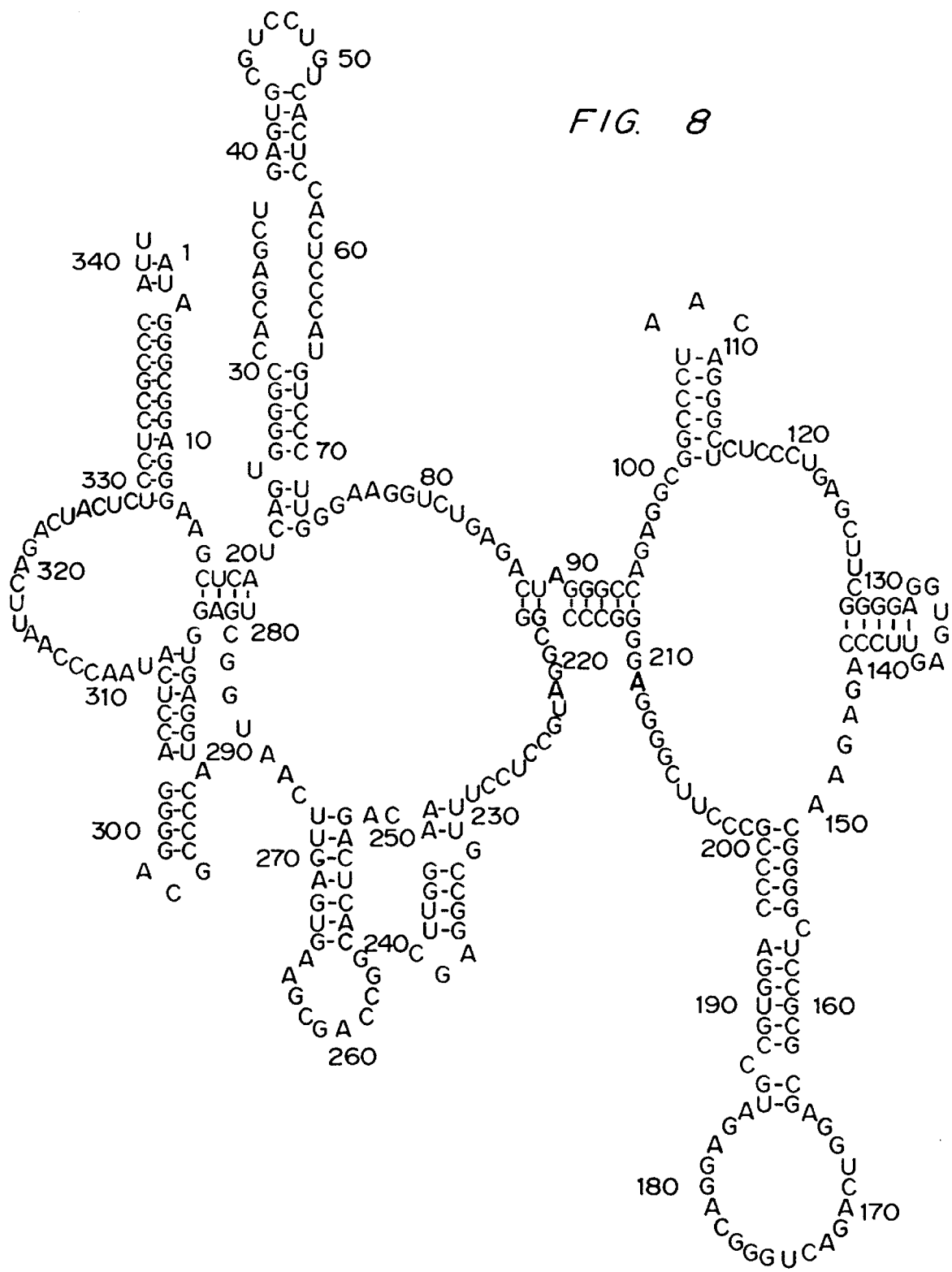
FIG. 8 is the sequence and structure of H1 RNA (Sequence ID No. 11) from Altman et al., $Genomics$ 18: 418–422 (1993).

The sequence and proposed secondary structure of H1 RNA, the RNA component of human RNase P, was reported by Altman et al. 25 (1993), the teachings of which are generally known in the art. The sequence and proposed structure of H1 RNA is shown in FIG. 8 (Sequence ID No. 11). The sequence and proposed secondary structure of M1 RNA, the RNA component of *E. coli* RNase P, was reported by James et al., Cell 52: 19 (1988), the teachings of which are generally 30 known in the art. The sequence of M1 RNA is included as Sequence ID No. 40.

Because of the similarity in secondary structure and substrate specificity among the RNase P's of diverse origin, it is possible to use an EGS designed to maximize efficiency of cleavage for the RNase P in question using techniques described herein to target any RNA in any cell, even though the catalytically active RNA subunits may have distinctly different sequences. See Altman, *Ann. Rev. Enzymology* 62: 1–39 (1989); Altman, *J. Biol. Chem.* 265: 20053–20056 (1990). Secondary structure is defined by intramolecular associations of complementary sequences. Base pairs can be canonical, A/U and G/C, or non-canonical, G/U, A/G, etc.

B. Exogenous RNA Having Catalytic Activity

An EGS can also be used in combination with an RNA sequence that demonstrates enzymatic activity in the presence or absence of a protein. That RNA sequence can be represented by a molecule like the entire H1 or M1 RNA molecule, any functionally equivalent molecule of prokaryotic or eukaryotic origin or derivation, or any portion thereof shown to have catalytic activity, either alone or in combination with a protein. Such a catalytic RNA is referred to herein as RNase P catalytic RNA and its sequence is referred to as an RNase P catalytic sequence. An RNA as described above is considered an RNase P catalytic RNA regardless of source, whether isolated, produced by chemical synthesis, or transcribed from a gene. As noted above, an EGS effective to convert a targeted sequence into a substrate for human RNase P, will also be effective in making the substrate a target for procaryotic RNase P.

RNase P catalytic RNA can be derived from naturally occurring RNase P catalytic RNAs, for example, by deleting portions and by making nucleotide substitutions. Such derived catalytic RNAs need only retain enough of the catalytic activity of naturally occurring RNase P catalytic RNA to cleave target RNA. A preferred method of generating RNase P catalytic sequences is by in vitro evolution as described below.

There are two principle situations in which RNase P catalytic RNA or RNase P is utilized in combination with EGS: in vitro in the absence of cells or cellular RNase P and in circumstances wherein the RNA to be cleaved is located in a portion of a cell not containing endogenous RNase P. In the latter case, the genes encoding the analogs of M1 RNA and C5 protein, as defined above, or the human or other eukaryotic equivalents thereof, are introduced into the cell at the desired location for cleavage using a suitable vector or other method known to those skilled in the art for introduction and expression of a gene in a cell.

RNase P Internal Guide Sequences

A guide sequence and the catalytic RNA subunit of an RNase P can be linked to form a single oligonucleotide molecule possessing both the targeting function of an EGS and cleavage function of RNase P catalytic RNA. Such a combination, in a single oligonucleotide molecule, is referred to as an RNase P internal guide sequence (RIGS). An RIGS can be used to cleave a target RNA molecule in the same manner as EGS.

RIGSs can be formed by linking a guide sequence to an RNase P catalytic sequence by any suitable means. For example, an EGS and RNase P catalytic RNA can be prepared as separate molecules which are then covalently linked in vitro. Alternatively, a complete RIGS can be synthesized as a single molecule, either by chemical synthesis, or by in vitro or in vivo transcription of a DNA molecule encoding linked GS and RNase P catalytic sequence. The linkage between the GS and RNase P domains of an RIGS can have any form that allows the domains to cleave a target RNA. For example, the two domains could be joined by an oligonucleotide linker. Preferably, the linker will be composed of an ordinary nucleotides joined by phosphodiester bonds. The GS and RNase P catalytic sequence components can be joined in either order, with the RNase P catalytic sequence linked to either the 3' end or 5' end of the GS component.

RIGSs can be used for cleavage of target RNA both in vitro and in vivo. In vitro, the RIGS can function without RNase P protein components in vitro, although activity of the RIGS can be increased by the addition of RNase P protein components. In vivo, endogenous RNase proteins will stimulate activity of the RIGS. The activity of both prokaryotic- and eukaryotic-based RIGSs are expected to be enhanced by the presence of either prokaryotic or eukaryotic RNase P protein components.

Method For Producing EGSs And RIGSs Having Enhanced Efficacy

EGSs and RIGSs having enhanced binding affinity as measured by decreased energy of binding can be designed by in vitro evolution. Such a method can be used to identify RNA molecules with desired properties from pools of molecules that contain randomized sequences. As demonstrated more clearly in the examples, appropriately modified, these methods can be used for the isolation of efficient EGSs and RIGSs. These new EGSs, when complexed with an exemplary target RNA, CAT mRNA substrate (Sequence ID No. 7), allow cleavage of the target by human RNase P at rates similar to those achieved with natural substrate.

Figure 2:
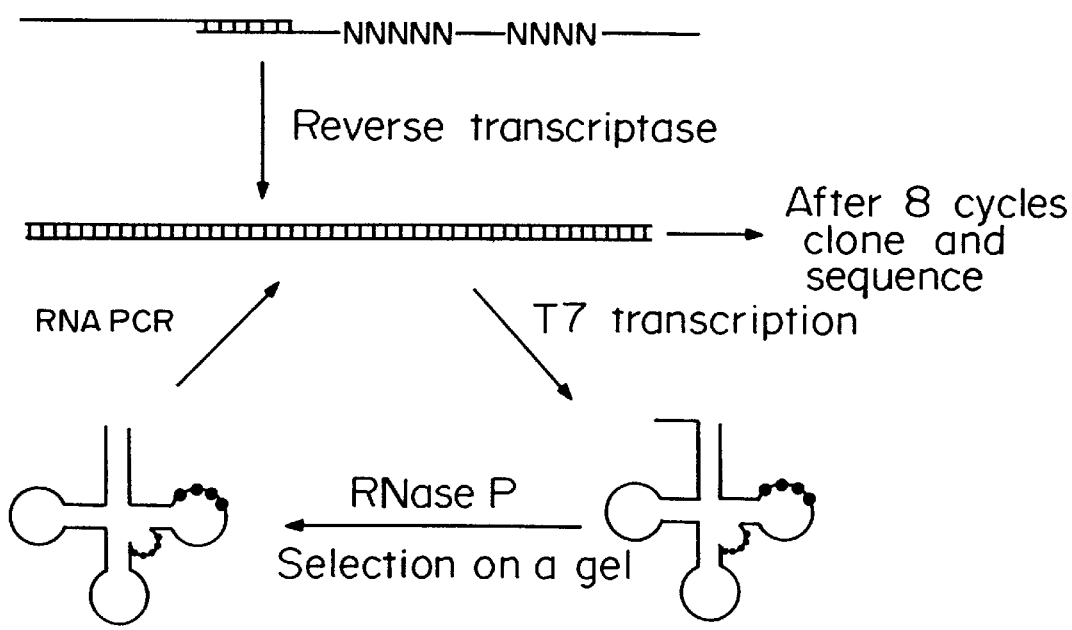
FIG. 2 depicts the general scheme for in vitro selection and amplification of chimeric substrates with enhanced efficiency for directing human RNase P cleavage. "Reverse transcriptase" denotes that the DNA polymerase capability of reverse transcriptase was used to create double-stranded template DNA from the overlapping DNA oligonucleotides SEC-1A (Sequence ID No. 2) and SEC-1B (Sequence ID No. 3). "RNA-PCR" refers to reverse transcription coupled to PCR.

The general selection scheme is depicted in FIG. 2. In each round of selection, the pool of RNAs is digested with human RNase P, or with the RIGS, and the cleaved products are isolated by electrophoresis and then amplified to produce progeny RNAs. One of the template-creating oligonucleotides is used as the 5' primer for the polymerase chain reaction (PCR) in order to allow restoration of the promoter sequence and the leader sequence of the chimeric RNA for the next cycle of selection. The stringency of selection is increased at each cycle by reducing the amount of enzyme and the time allowed for the cleavage reaction, such that only those substrates that are cleaved rapidly by the enzyme are selected.

In the first three rounds of selection, RNA substrates are digested with an appropriate amount of human RNase P, for example, 3.6 units, or the equivalent activity of the RIGS. One unit of human RNase P is defined as that amount of enzyme that cleaves 1 pmol of precursor to tRNA$_{Tyr}$ from *E. coli* in 30 min at 37° C. For assays in subsequent rounds of selection, the amount of enzyme is reduced, and the incubation time is shortened so that less than 20 percent of the substrate is cleaved. Cleavage products are separated from uncleaved substrates by electrophoresis and RNA extracted.

The purified cleavage product RNAs are reverse transcribed and amplified by PCR. The double-stranded DNA generated by PCR regains the promoter sequence and the leader sequence from the sequence in the primer, and is then used as a template for transcription of RNA for the next round of selection. After eight cycles of selection, the resulting pool of double-stranded DNAs is cloned into an appropriate vector and sequenced.

In order to test the abilities of EGSs or RIGSs derived from the individual variants, sequences corresponding to the GS segment of each chimeric tRNA are amplified by PCR, and RNAs transcribed with an appropriate RNA polymerase. RNA cleavage by the selected EGS or RIGS is then assayed. Sequences in common in the most active EGS and RIGSs are then determined and new EGS and RIGSs designed.

As described in the examples, simulation of evolution in vitro was used to select EGSs that bind strongly to a target substrate mRNA and that increase the efficiency of cleavage of the target by human ribonuclease P to a level equal to that achieved with natural substrates. The most efficient EGSs from tRNA precursor-like structures with the target RNA, in which the analog of the anticodon stem has been disrupted, an indication that selection for the optimal substrate for ribonuclease P yields an RNA structure different from that of present-day tRNA precursors.

Chemically Modified EGS And RIGS

Although chemically unmodified oligoribonucleotides can function as effective EGS or RIGS in a nuclease-free environment, the shorter half-life in serum and inside cells reduces their effectiveness as therapeutics. Chemical modifications can be made which greatly enhance the nuclease resistance of EGS and RIGS without compromising their biological function of inducing or catalyzing cleavage of RNA target. For example, one or more of the bases of an EGS or RIGS construct can be replaced by 2' methoxy ribonucleotides or phosphorothioate deoxyribonucleotides using available nucleic acid synthesis methods. Synthesis methods are described by, for example, Offensperger et. al., *EMBO J.* 12: 1257–1262 (1993); PCT WO 93/01286 by Rosenberg et al. (synthesis of sulfurthioate oligonucleotides); Agrawal et al., *Proc. Natl. Acad. Sci. USA* 85: 7079–7083 (1988); Sarin et al., *Proc. Natl. Acad. Sci. USA* 85: 7448–7794 (1989); Shaw et al., *Nucleic Acids Res* 19: 747–750 (1991) (synthesis of 3' exonuclease-resistant oligonucleotides containing 3' terminal phosphoroamidate modifications); all of which are hereby incorporated herein by reference.

It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the EGS or RIGS molecule, as described, for example, by Orson et al., *Nucl. Acids Res.* 19: 3435–3441 (1991). Furthermore, cytosines that may be present in the sequence can be methylated, or an intercalating agent, such as an acridine derivative, can be covalently attached to a 5' terminal phosphate to reduce the susceptibility of a nucleic acid molecule to intracellular nucleases. Examples of this are described in Maher et al., *Science* 245: 725–730 (1989) and Grigoriev et al., *J. Biol. Chem.* 267: 3389–3395 (1992).

Another class of chemical modifications is modification of the 2' OH group of a nucleotide's ribose moiety, which has been shown to be critical for the activity of the various intracellular and extracellular nucleases. Typical 2' modifications are the synthesis of 2'—O—Methyl oligonucleotides, as described by Paolella et al., *EMBO J.* 11: 1913–1919 (1992), and 2'-fluoro and 2'-amino-oligonucleotides, as described by Pieken et al., *Science* 253: 314–317 (1991), and Heidenreich and Eckstain, *J. Biol. Chem* 267: 1904–1909 (1992). Portions of EGS and RIGS molecules can also contain deoxyribonucleotides. Such substitutions improve nuclease resistance by eliminating the critical 2' OH group.

Application Of EGS And RIGSs As Laboratory Or Clinical Reagents

External guide sequences and RIGSs have applications as in vitro reagents, in a similar fashion to restriction enzymes, and as therapeutic agents, for cleavage and inactivation of specific host cell RNA or RNA coded for by pathogenic organisms such as bacteria or viruses, as demonstrated by the following examples.

As used herein, an EGS or RIGS is an oligonucleotide molecule. It is to be understood, however, that for therapeutic purposes, a DNA molecule encoding an EGS molecule or encoding an RIGS molecule could be utilized. Accordingly, unless otherwise specified, administration of an EGS or RIGS encompasses both the RNA molecule that hydrogen bonds to a target nucleic acid sequence that is cleaved, as well as a DNA molecule encoding the RNA molecule, which is expressed under conditions wherein the RNA molecule functions as an EGS or RIGS.

An external guide sequence can be brought into contact with any RNA having sequences complementary to the EGS, in the presence of RNase P, and the RNA will be cleaved at the targeted site. In this manner, the activity of endogenous RNase P in any cell, such as the RNase P of human cells, can be directed to destroy specific messenger, viral or other RNAs by the use of an appropriate EGS RNA.

A. Reagents For In vitro Applications

DNA restriction endonucleases are invaluable reagents for the molecular biologist. Patterns of restriction fragment sizes are used to establish sequence relationships between DNA molecules, and large DNAs can be cleaved to give fragments of sizes useful for genetic engineering, sequencing, and studying protein binding. RNA processing enzymes can be utilized under conditions such that they also cleave RNA with considerable sequence specificity.

Specific ribozymes can be prepared by combining the specific guide sequence with RNase P or functional equivalents thereof. In the preferred embodiment, the external guide sequence and the RNase P catalytic RNA are separate; alternatively, the two sequences can be joined either directly or via a linker. The linker can be any molecule that can be covalently bound to oligonucleotides. Numerous linkers are known to those of skill in the art. A preferred linker is an oligonucleotide because it allows direct synthesis of the complete RIGS.

B. Therapeutics

1. Determination and Preparation of Complementary Sequences

Any cellular gene product expressed as RNA, including proteins encoded by mRNA and structural RNAs themselves, can be targeted for inactivation by RNase P, or directly by an RIGS using sequences engineered to include appropriate regions of sequence and/or structure for binding to the targeted RNA and the desired site of cleavage. The cellular gene product could be a product of an oncogene with an altered sequence, such as the ras gene product; where the product is not a normal cell component, a viral protein, such as one encoded by an essential gene for HIV replication; or a bacterial protein.

In many cases, the critical genes an infective or pathological agent have been isolated and sequenced. Appropriate complementary sequences can be synthesized using standard techniques, reagents, and equipment based on these known sequences.

2. Preparation of an appropriate pharmaceutical composition for delivery of the EGS or RIGS to the targeted RNA.

There are two primary mechanisms for delivering the EGS or RIGS to intracellular RNA that has been targeted for cleavage: diffusion and via a vector.

As discussed above, any RNA that is important in a disease process can be targeted and appropriate complementary sequences made synthetically or by copying cloned sequence. For example, cancer regulatory genes can be targeted. Since RNase P is predominantly found in the nucleus of eukaryotic cells, the infectious agents most likely to be inhibited by administration of appropriate EGS to the infected cells are those in which critical RNA sequences are transcribed in the nucleus. Important examples of the viral agents that replicate in the cell nucleus include herpes viruses, including herpes simplex virus, varicella-herpes zoster virus, cytomegalovirus, and Epstein-Barr virus; hepatitis B virus; adenoviruses; paramyxoviruses such as measles; and the retroviruses, such as human immunodeficiency virus, HIV I, HIV II, HIV III and HTLV-1. RIGSs should cleave target RNA in any area of the cell since the catalytic activity is self-contained.

3. Vector-mediated delivery of EGS and RIGSs.

Preferred vectors are viral vectors such as the retroviruses which introduce EGS and RIGS directly into the nucleus where it is transcribed and released into the nucleus. Under the appropriate conditions, the EGS or RIGS will hybridize to the targeted RNA and the endogenous RNase P or RIGS will cleave the hybridized RNA at the 5' side of the hybrid region.

Methods for using retroviral vectors for gene therapy are described in U.S. Pat. Nos. 4,868,116 and 4,980,286, and PCT application PCT/US89/03794 and PCT/US89/00422, the teachings of which are incorporated herein.

Defective retroviral vectors, which incorporate their own RNA sequence in the form of DNA into the host chromosome, can be engineered to incorporate EGS and RIGSs into the host, where copies will be made and released into the cytoplasm to interact with the target nucleotide sequences.

EGS and RIGSs are particularly useful as a means of targeted therapy into hematopoietic cells of patients suffering from virus-induced disease of those cells, such as AIDS. The most efficacious methodology presently available for the introduction of specific genetic sequences into human cells involves the use of RNA-containing retroviruses which serve as vehicles or vectors for high efficiency gene transfer into human cells.

RNase P-based therapy can also be used as a means of preventing the spread of HIV-1 and or providing a HIV-1 resistant population of T-cells that will be able to confer immune function to infected individuals. Patients who have been recently diagnosed as having antibodies to HIV-1, but who do not yet show AIDS symptomatology, are the preferred candidates for therapy. This procedure necessitates removal of some of the patient's bone marrow stem cells and subsequent partial cytoblation. The removed cells can be treated in the laboratory with appropriate EGS or RIGS compositions, using appropriate viral vectors, such as defective viral vectors, and then restored to the same individual. The treated cells will develop in the patient into mature hematopoietic cells, including T-cells. These T-cells will have normal immune function and, most importantly, will be intracellularly immunized to prevent their destruction by any HIV-1 still present in the patient.

Bone marrow stem cells and hematopoietic cells are relatively easily removed and replaced and provide a self-regenerating population of cells for the propagation of transferred genes. RNase P-based therapeutics allow the selective inactivation of other unwanted genes in cells, such as activated oncogenes, involved in the causation and maintenance of cancer cells.

In contrast to the approaches presently in use which are aimed at preventing or limiting infection with HIV, it should be possible to use RNase P-based technology to treat, and possibly to cure, HIV infection, and related diseases of white blood cells which are subject to transformation by retroviral vectors carrying EGS or RIGS. Particular examples of diseases that may be treated using EGS and RIGS include not only HTLV-1, but also various retroviral-induced leukemias resulting from chromosomal translocations that produce chimeric RNAs which produce proteins that are unique to those cells and that can act as growth stimulators or oncogenes. Other types of transformed tissues that might be treatable include all cancer cells carrying identified oncogenes of known sequence.

4. Topical and other EGS and RIGS compositions for local administration.

EGS and RIGS may also be administered topically, locally or systemically in a suitable pharmaceutical carrier. *Remington's Pharmaceutical Sciences,* 15th Edition by E. W. Martin (Mark Publishing Company, 1975), the teachings of which are incorporated herein by reference, discloses typical carriers and methods of preparation. EGS and RIGS may also be encapsulated in suitable biocompatible microcapsules, microparticles or microspheres formed of biodegradable or non-biodegradable polymers or proteins or liposomes for targeting to phagocytic cells. Such systems are well known to those skilled in the art and may be optimized for use with the appropriate EGS and RIGSs.

Therapeutically the oligoribonucleotides are administered as a pharmaceutical composition consisting of an effective amount of the EGS or RIGS to inhibit transcription of a targeted RNA and a pharmaceutically acceptable carrier. Examples of typical pharmaceutical carriers, used alone or in combination, include one or more solid, semi-solid, or liquid diluents, fillers and formulation adjuvants which are non-toxic, inert and pharmaceutically acceptable. Such pharmaceutical compositions are preferable in dosage unit form, that is, physically discreet units containing a predetermined amount of the drug corresponding to a fraction or multiple of the dose which is calculated to produce the desired therapeutic response. It is essential that the oligonucleotides be delivered in a form which prevents degradation of all of the oligonucleotide before it reaches the intended target site.

A preferred embodiment is an EGS or an RIGS administered as a viral vector, encoding the EGS or RIGS, or in a liposome, such that an effective amount of EGS or RIGS is delivered. Generally these will produce a concentration between 1 μM and 1 mM at the site of the cells to be treated. Such compounds and compositions can be formulated as a topical composition, for example, for application to a viral lesion such as that produced by herpes simplex virus. These will generally contain between 1 μM and 1 mM oligonucleotide per unit of carrier, or produce a concentration between 1 μM and 1 mM at the site of the cells to be treated. Oral compositions, although not preferred, are in the form of tablets or capsules and may contain conventional excipients. Another preferred composition is a polymeric material applied locally for release of EGS or RIGS. Still another preferred composition is a solution or suspension of the EGS or RIGS in an appropriate vector in combination with conventional pharmaceutical vehicles are employed for parenteral compositions, such as an aqueous solution for intravenous injection or an oily suspension for intramuscular injection.

For clinical applications, the dosage and the dosage regimen in each case should be carefully adjusted, utilizing sound professional judgment and consideration of the age, weight and condition of the recipient, the route of administration and the nature and gravity of the illness.

The present invention, EGS and RIGSs, will be further understood by reference to the following non-limiting examples.

EXAMPLE 1

Cleavage of tRNA precursor fragments by human RNase P in the presence of EGS.

Figure 3:
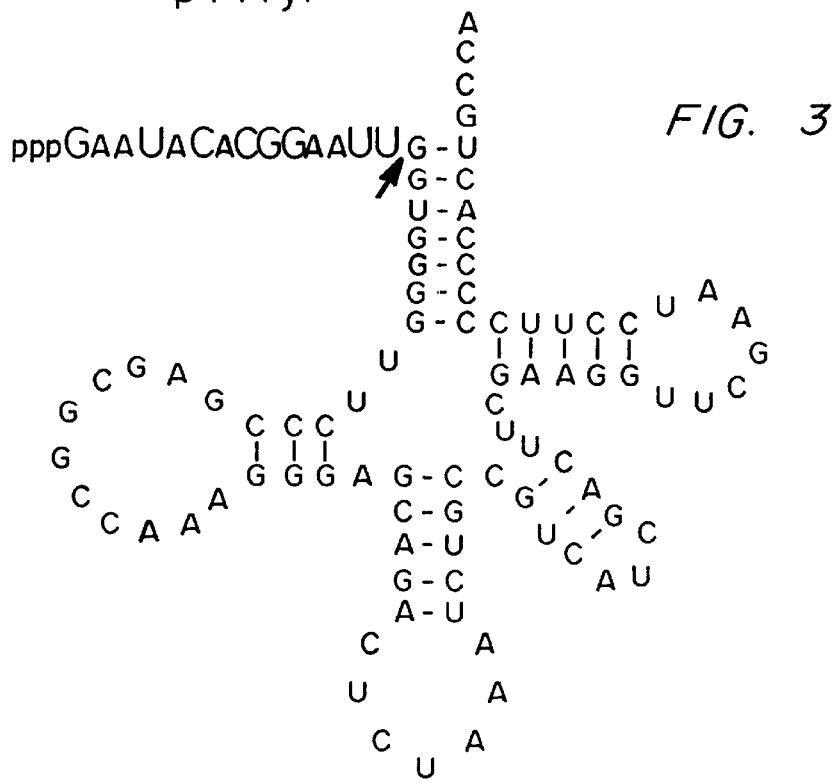
FIG. 3 is the sequence and secondary structures of the precursor to tRNA$^{Tyr}$ (Sequence ID No. 4) and a complex of a substrate and EGSΔ(1–18) (Sequence ID No. 5), which is derived from tRNA$^{Tyr}$ but lacks the first eighteen nucleotides from the 5' end of the mature tRNA$^{Tyr}$. pTyr: $E.\ coli$ tRNA$^{Tyr}$ precursor; pAva: substrate (target) RNA with 5' leader sequence and the first fourteen nucleotides of $E.\ coli$ tRNA$^{Tyr}$ (Sequence ID No. 6).
Figure 3:
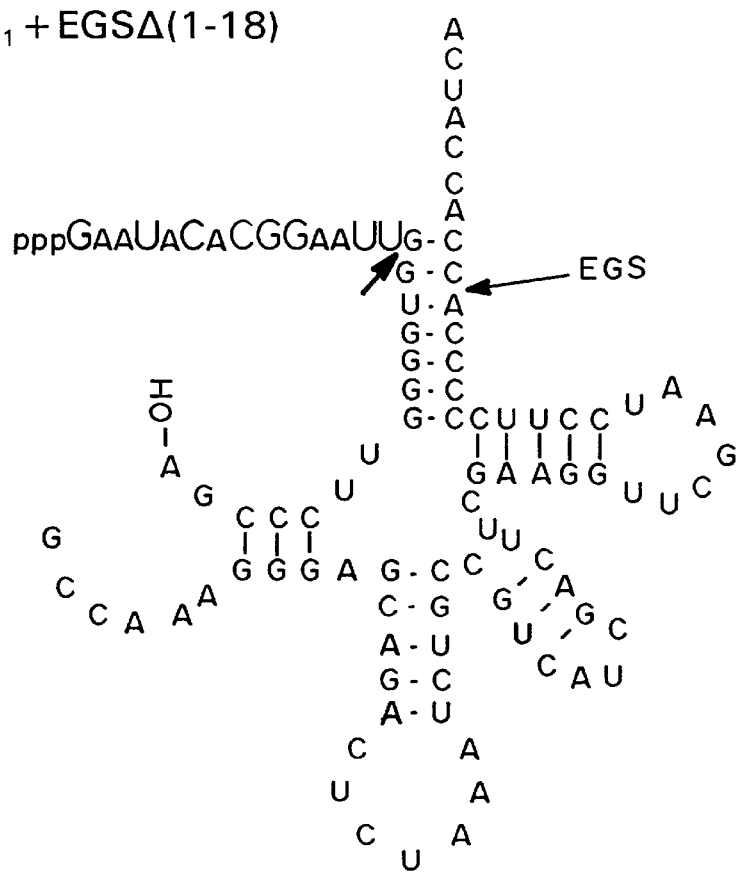

An EGS that can target RNA for cleavage by human RNase P was prepared using a small RNA fragment, pAva (Sequence ID No. 6, FIG. 3) which contains a 5' precursor sequence and the first fourteen nucleotides from the 5' terminus of a tRNA. The leader sequence of *E. coli* tRNA$^{Tyr}$ precursor can be cleaved correctly when another piece of RNA, for example, EGSΔ1–18 (Sequence ID No. 5), which lacks the first eighteen nucleotides of the 5' terminus of mature tRNA$^{Tyr}$ but retains the remaining 3' proximal sequence, is hybridized to the target RNA.

Human RNase P was partially purified from HeLa cells using the method of Bartkiewicz et al., *Genes and Development* 3: 488–499 (1989). The substrates were prepared by in vitro transcription in the presence of [α-$^{32}$P]GTP. [α-$^{32}$P] GTP labelled pAva (Sequence ID No. 6) I RNA (28 nt) was mixed with unlabelled EGS RNA and the mixture was incubated at 37° C. in 50 mM Tris-Cl (pH 7.5), 100 mM NH$_4$Cl, and 10 mM MgCl$_2$ with enzyme for 30 min. Labelled pAva (Sequence ID No. 6) I RNA alone was also incubated with or without enzyme. Analysis by gel electrophoresis shows that the EGS plus enzyme resulted in cleavage of the RNA.

The 3' proximal oligonucleotide is the external guide sequence. Because the lengths of the leaders and their sequences, as well as the sequences of the mature domain, are not conserved among different precursor-tRNAs, the main determinants for human RNase P cleavage must be in some of the conserved structural features of various tRNAs. This general idea is borne out by the fact that several other EGSs that did not mimic exactly the structure of parts of a tRNA did not target complementary RNAs. Examples of such changes include changes in the number of possible base pairs in the D or amino acyl stems, changes in positions 8 and 9 of the mature tRNA sequence, and a change from cytosine to uracil at position 57. However, an EGS that lacked the anticodon stem and loop, or the variable stem and loop, resulted in efficient cleavage, indicating that these parts of the EGS, separately, were not essential for recognition of the target complex by the enzyme.

Accordingly, if an mRNA, rather than part of a precursor tRNA sequence, is incorporated into the double-stranded stem region of a putative target complex, and the resulting hybrid contains the structural features required of a substrate for human RNase P activity, the mRNA will be cleaved by human RNase P.

EXAMPLE 2

Specific Cleavage of CAT mRNA in vitro by Human RNase P using an External Guide Sequence Examples provided below show the efficiency of cleavage of the mRNA for chloramphenicol acetyltransferase (CAT) by human RNase P. The sequence of the 5' oligoribonucleotide, as well as that of the EGS, depends on the choice of target site in the mRNA. The presence of the appropriately designed EGS efficiently reduces CAT enzymatic activity in vivo, as well as promotes cleavage of CAT mRNA in vitro, indicating that this method should be of general use for gene inactivation.

Figure 4A:
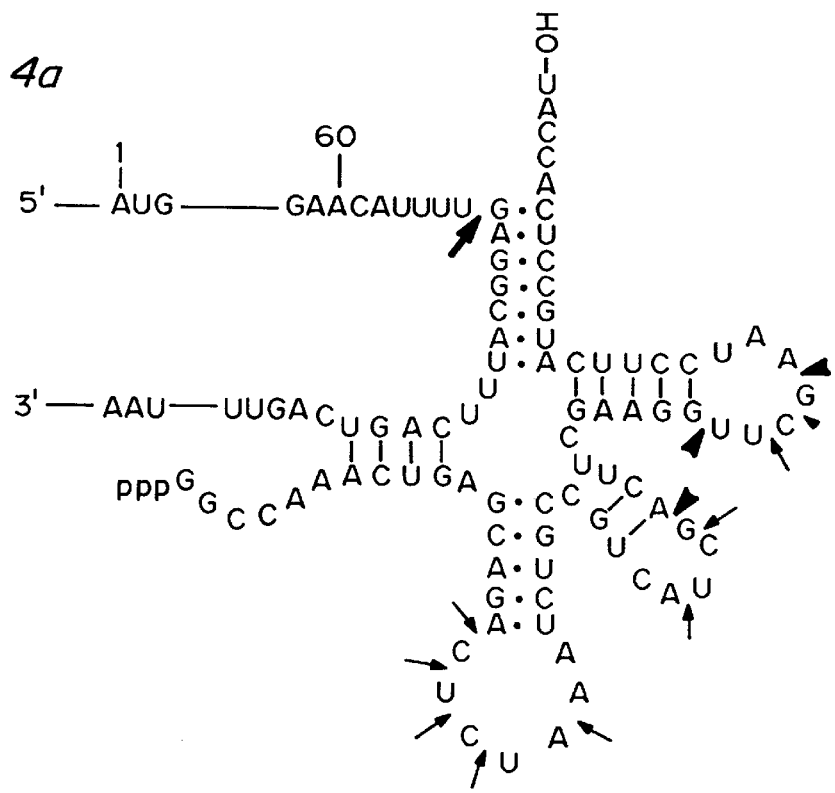
FIGS. 4A, 4B, 4C, 4D, 4E, and 4F are the proposed secondary structures of complexes of CAT mRNA and various EGS. 4A and 4D depict complexes between the complementary region CAT mRNA (Sequence ID No. 7) and EGS$^{CAT}$ (Sequence ID No. 8). 4B and 4E are complexes of CAT mRNA (Sequence ID No. 7) and EGS 9 (Sequence ID No. 9). 4C and 4F are complexes of CAT mRNA (Sequence ID No. 7) and EGS$^{CAT}$ΔAC (Sequence ID No. 10). Hollow arrows denote sites of cleavage by human RNase P.

An EGS custom-designed for the mRNA for chloramphenicol transacetylase (CAT), shown in FIG. 4A, EGS$^{CAT}$, Sequence ID No. 8), can direct the specific cleavage of CAT mRNA by human RNase P in vitro or in vivo cells in tissue culture. However, the cleavage reaction is inefficient compared to cleavage of natural tRNA precursor substrates.

The proposed secondary structure of a complex of CAT mRNA (Sequence ID No. 7) and EGS$^{CAT}$ (Sequence ID No. 8) resembles the tRNA cloverleaf structure, but it includes sequences not normally found in the tRNA from which it was originally derived, namely, tyrosyl tRNA (tRNA$^{Tyr}$) (Sequence ID No. 6) of *Escherichia coli*. To ensure that appropriate tertiary interactions that facilitate the process of enzyme-substrate recognition exist in the complex, parts of the EGS that participate in tertiary interactions in the analogous tRNA structures were changed in two ways. First, four nucleotides in the equivalent of the T loop and five in the equivalent of the variable loop were randomized by incorporation of equimolar quantities of the deoxyribonucleotides dA, dG, dC and T into a DNA template to yield an initial population of 2.6×10$^5$ sequence variants. Second, during each round of selective amplification, random mutations were introduced by performing polymerase chain reaction (PCR) at an error rate of approximately 0.1 percent per nucleotide incorporated, using the method of A. Beaudry and G. F. Joyce, *Science* 257: 635 (1992). The mRNA for the gene for chloramphenicol acetyltransferase (CAT) can be easily manipulated on plasmids and the enzymatic activity is readily expressed in tissue culture cells so it was used as a target substrate. As demonstrated below, an EGS can target CAT mRNA (Sequence ID No. 7) for specific cleavage by human RNase P. FIG. 4A shows a complex in which an EGS, EGS$^{CAT}$ (Sequence ID No. 8), could base-pair with nucleotides 67 to 79 of CAT mRNA (Sequence ID No. 7), where the first nucleotide of the translation initiation codon is numbered 1, and direct human RNase P to cleave that mRNA at nucleotide 67. The EGS$^{CAT}$ (Sequence ID No. 8) construct was derived from the *E. coli* tRNA$^{Tyr}$ (Sequence ID No. 6) gene where the first eighteen nucleotides from the 5' terminus have been deleted and the sequences on the D-loop and acceptor-loop have been changed to make base-pairs with CAT mRNA. The EGS$^{CAT}$ (Sequence ID No. 8) fused upstream with a T7 promoter was cloned into a pUC19 vector. The EGS$^{CAT}$ RNA (Sequence ID No. 8) was prepared through in vitro transcription with T7 RNA polymerase.

The HindIII-BamHI fragment of CAT gene (pCAT™, Promega) was cloned in pGem-2. The plasmid was truncated with EcoRI and a 260 nucleotide-long transcript was obtained by in vitro transcription with T7 RNA polymerase in the presence of [α-$^{32}$P]GTP. The EGS sequence was synthesized by polymerase chain reaction, using the *E. coli* tRNA$^{Tyr}$ gene as template, with oligonucleotide GCCAAACTGAGCAG ACTC (Sequence ID No. 12) and GCGCggtaccAAAAATGGTGAGG CATGAAGG (Sequence ID No. 13). The bold letters in the oligonucleotide sequences indicate the bases needed to make base pairs to CAT mRNA, the underlined letters indicate the sequence complementary to the transcription termination signal, and the lower case letters shows an extra linker sequence. The sequence GCGC at the 5' end of the second oligonucleotide are extra nucleotides. The PCR fragment was digested with HindIII and cloned into pUC19 with a T7 promoter upstream from the EGS sequence. The EGS$^{CAT}$ RNA (Sequence ID No. 8) was transcribed with T7 RNA polymerase after the plasmid was linearized with DraI. A mixture of unlabelled and [α-$^{32}$P]GTP labelled CAT mRNA fragment, 0.2 pmole in total, was mixed with the EGS$^{CAT}$ RNA (Sequence ID No. 8) in amounts of 4 pmole, 1 pmole, 1 pmole, 0.4 pmole and 0.2 pmole. Each mixture was incubated at 37° C. in 50 mM Tris-Cl (pH 7.5), 100 mM NH$_4$Cl, and 25 mM MgCl$_2$ with enzyme for one hour. The reaction was stopped by addition of an equal volume of dye solution with excess EDTA and then subjected to a 5 % polyacrylamide-7M urea gel. CAT mRNA alone was incubated without and with enzyme and loaded on the gel.

Primer extension analysis determining the precise site of EGS$^{CAT}$-directed cleavage by human RNase P was conducted as follows. A reverse transcription reaction was performed on the uncleaved and cleaved CAT mRNA using an oligodeoxyribonucleotide GGCCGTA ATATCCAGCT-GAACGG (Sequence ID No. 14), complementary to nucleotides 129 to 107 of CAT mRNA. The reaction was incubated in 100 mM Tris-Cl (pH 8.3), 10 mM KCl, 6 mM MgCl$_2$, 10 mM DTT and 2 units AMV reverse transcriptase at 46° C. for 2 hours. Labelled G, A, U, C were used as reference analyses of DNA sequences corresponding to the CAT mRNA template.

The precise site of cleavage of CAT mRNA was determined by primer extension analysis using an oligodeoxyribonucleotide primer complementary to nucleotides 129 to 107 of the RNA, showing that the cleavage occurs between nucleotides 66 and 67, as expected.

The results of the EGS$^{CAT}$ RNA-directed cleavage of CAT mRNA were analyzed by gel electrophoresis. In the presence of EGS$^{CAT}$ (Sequence ID No. 8) molecules, CAT mRNAs were cleaved to give rise to two products with the expected size. Analysis of the products of the reaction showed that the end groups contained 5' phosphoryl and 3' hydroxyl termini, the same as those normally generated by RNase P. The results show conclusively that the specific cleavage of CAT mRNA is due to an EGS-directed RNase P hydrolytic reaction.

For up to five-fold molar excess of EGS$^{CAT}$ RNA to mRNA, the cleavage efficiency is proportional to the amount of EGS$^{CAT}$ added. However, more than ten-fold excess of EGS$^{CAT}$ molecules caused a decrease in the cleavage efficiency. One explanation for this is that EGS$^{CAT}$ alone inhibits the enzymatic activity by competing with the mRNA-EGS complex for the enzyme. The reaction proceeds in a linear fashion for more than 3 hours at 37° C. Denaturation and reannealing of the oligonucleotides in the target complex did not improve the efficiency of cleavage. The reaction has an absolute requirement for Mg$^{2+}$ with an optimal concentration of 25 mM, in contrast to that with tRNA$^{Tyr}$ precursor as substrate, which has an optimal Mg$^{2+}$ concentration of between 2 and 10 mM.

EXAMPLE 3

Inhibition of Expression of CAT Activity in Green Monkey CV-1 Cells by EGS$^{CAT}$ In order to test whether the EGS can function in vivo, the EGS$^{CAT}$ sequence (Sequence ID No. 8) was inserted downstream of a mouse U6 snRNA gene promoter in a BLUE-SCRIPT™ (Stratagene, La Jolla, Calif.) vector forming pEGS$^{CAT}$. The EGS$^{CAT}$ sequence (Sequence ID No. 8) can be transcribed by RNA polymerase III and the transcription can terminate at a T$_5$ cluster following the EGS sequence in either S100 extract or living cells. Green monkey fibroblast cells CV-1 were cotransfected with pCAT and pEGS$^{CAT}$ plasmids. After transfection with pCAT, which encodes the CAT gene, and PEGS$^{CAT}$, cells were harvested and CAT activity was assayed.

CV-1 cells were maintained in Dulbecco's modified Eagle medium that contained 10% fetal calf serum. One day prior to transfection cells were split 1:10 and plated in 60 mm Petri plates. Two hours prior to transfection cells were fed with 4.5 ml of fresh medium with 10% fetal calf serum. Transfection was performed by the calcium phosphate precipitation procedure using 2.5 µg of pCAT DNA and various amounts of PEGS$^{CAT}$ DNA, ranging from one to 6.25 µg. Twenty-four hours after transfection, cells were harvested and cell extracts were assayed for CAT activity.

The extract from cells cotransfected with EGS$^{CAT}$ construct apparently decreased the conversion of chloramphenicol to its acetylated forms. The degree of inhibition was measured quantitatively by counting of the spots excised from a TLC plate. EGS$^{CAT}$ cotransfection produced greater than 50% inhibition compared to the control with no EGS$^{CAT}$ cotransfection. There was substantial loss of ability to inhibit CAT expression when a higher ratio of pEGS$^{CAT}$ to pCAT was introduced. Similar experiments yielding approximately 70% of CAT activity have also been performed with human cells in tissue culture.

EXAMPLE 4

Preparation of EGS with Altered Sequence that Enhance Degradation of Target RNA by RNase P As explained in detail below, two classes of EGS were designed, as shown in FIGS. 4A, 4B, 4C, 4D, 4E, and 4F. The first class involves deletions of large segments of the EGS as suggested in Example 1 and described in Examples 2 and 3. For example, it has been found that the anticodon loop and stem can be deleted, as shown in EGS$^{CAT}$ΔAC (Sequence ID No. 10) of FIG. 4C and 4F, and the EGS can still promote cleavage by RNase P of a target RNA (CAT mRNA containing Sequence ID No. 7 in FIGS. 4C and 4F). The anticodon loop and part of the variable loop can alternatively be deleted from the EGS, and the EGS will promote cleavage with greater efficiency than the parent EGS molecule. The most efficient EGS of this deletion class was the one in which the anticodon stem and loop was deleted. This EGS$^{CAT}$ΔAC (Sequence ID No. 10) promoted cleavage by human RNase P of a target mRNA (CAT mRNA) at a rate 10-fold higher than the parent EGS. The deletion of both variable and anticodon stems and loops, however, does not yield a more efficient EGS, although the variable loop can consist of only one or two nucleotides and still be highly efficient.

The second class of EGSs have changes in both the equivalent of the T loop, the variable loop, and the anticodon stem of the tRNA-like segment of the EGS. Three such EGSs, described below, are EGS 6, EGS 8 and EGS 9 (Sequence ID No. 9, FIGS. 4B and 4E). As shown below, EGS 9 is the most efficient of the EGSs in these examples and directs cleavage by human RNase P of a target RNA (CAT mRNA) at a rate approximately fifty to one hundred fold greater than the parent EGS.

These results apply to relative rates of cleavage at a particular site in a target mRNA. The absolute rates of cleavage at any particular site still depend on access of the EGS to that particular site.

EXAMPLE 5

Preparation of RNAs with Randomized Nucleotides
A. Preparation of Chimeric Covalently Linked mRNA-EGS Substrate The procedure to select for EGSs that are more efficient in guiding RNase P to the target CAT mRNA involves the synthesis of a population of chimeric, covalently linked mRNA-EGS substrates which are then run through cycles of in vitro mutation and selection for molecules which can serve as substrates for RNase P. Double-stranded DNA templates were made by annealing of and enzymatically extending two overlapping synthetic oligonucleotides: TAATACGACTCACTATA GAACATTTTGAG-GCATTTCAGTCAGTTGGCCAAACTGAGCAGAC (SEC-1A, Sequence ID No. 2) and TGGTGAGGCAT-GAAGGNN NNGAACCTTCNNNNNGCAGATTTA-GAGTCTGCTCAGTTTGGCC (SEC-1B, Sequence ID No. 3), where the complementary sequences are underlined and the randomized nucleotides (N) were introduced during their machine synthesis by incorporating equimolar quantities of four nucleotides. These sequences create a chimeric tRNA gene which contains sequences from CAT mRNA and tRNA$^{Tyr}$ from E. coli as well as nine nucleotides (N) that are randomized. A promoter for T7 bacteriophage RNA polymerase is included in SEC-1A (Sequence ID No. 2). The extension was carried out with AMV reverse transcriptase at 46° C. for two hours. Variant RNA pools were prepared by transcription with T7 polymerase in 40 mM Tris Cl, pH 7.9, 6 mM MgCl$_2$ 10 mM dithiothreitol 2 mM spermidine 1 mM NTPs containing 20 μci [α-$^{32}$P]GTP at 37° C.

B. The Selection Procedure

The general selection scheme is described above. One of the template-creating oligonucleotides (SEC-1A, Sequence ID No. 2) was also used as the 5' primer for the polymerase chain reaction (PCR) in order to allow restoration of the T7 promoter sequence and the leader sequence of the chimeric RNA for the next cycle of selection. The stringency of selection was increased at each cycle by reducing the amount of enzyme and the time allowed for the cleavage reaction, such that only those substrates that were cleaved rapidly by the enzyme were selected.

In the first three rounds of selection, RNA substrates were digested with 3.6 units of human RNase P, purified through the glycerol gradient step described by Yuan and Altman, Proc. Natl. Acad. Sci. USA 89: 8006–8010 (1992) and Bartkiewicz et al., Genes and Dev. 3:488 (1989)) in 50 mM Tris-Cl (pH 7.5), 10 mM MgCl$_2$, and 100 mM NH$_4$Cl at 37° C. for 2 hours. One unit of human RNase P is defined as that amount of enzyme that cleaves 1 pmol of precursor to tRNA$^{Tyr}$ from E. coli in 30 min at 37° C. For assays in subsequent rounds of selection, the amount of enzyme was reduced, and the incubation time was shortened so that less than 20 percent of the substrate was cleaved.

Cleavage products were separated from uncleaved substrates by electrophoresis on an eight percent polyacrylamide-7M urea gel. RNA was extracted from the gels by the crush and soak method.

The purified cleavage product RNAs were reverse transcribed and amplified by PCR with SEC-1A (Sequence ID No. 2) and SEC-1C (TGGTGAGGCATGAAGG, Sequence ID No. 15) as primers with a Perkin Elmer RNA PCR kit. The double-stranded DNA generated by PCR regained the T7 promoter sequence and the leader sequence from the sequence in the primer SEC-1A, and it was then used as a template for transcription of RNA for the next round of selection.

C. Characterization of the Selected RNAs and EGS RNA Derived from Them

After eight cycles of selection the resulting pool of double-stranded DNAs were cloned into the BLUE-SCRIPT™ vector (Stratagene, La Jolla, Calif.) vector. Eighteen plasmid DNAs were sequenced using Sequenase 2.0 (U.S. Biochemicals, Cleveland, Ohio).

In order to test the abilities of EGSs derived from the individual variants selected above for CAT mRNA targeting, sequences corresponding to the EGS segment of each chimeric tRNA were amplified by PCR using primers SEC-1A (Sequence ID No. 2) and SEC-1T (TAATACGACTCACTATAGGCCAACTGAGCAGAC, Sequence ID No. 16), which contains a promoter sequence for T7 polymerase, and RNAs were transcribed with T7 RNA polymerase. EGS-directed CAT mRNA cleavage was assayed in 10 μl of 50 mM Tris-Cl, pH 7.5, 10 mM MgCl$_2$ 100 nM NH$_4$Cl containing 0.25 pmol (1000 cpm) of substrate RNA and 1 or 5 pmol of EGS RNAs. Reaction mixtures were incubated at 37° C. for 30 min with 10 units of RNase P from HeLa cells, followed by electrophoresis in 5 % polyacrylamide/7M urea gels.

The gels showed a species of RNA migrating in the position expected for cleavage of substrate RNA in those lanes where the newly selected EGSs have been included in the reaction mixtures.

D. Sequence Analysis of Randomized EGSs.

Sixteen individual clones were sequenced. The sequence of the anticodon stem/loop, the variable (V) loop, and the T stem/loop are shown in FIG. 6. From the sequence that had been randomized in the T-loop, two particular sequences were most frequently selected: UUCGUGC, found in seven clones, and UUCGCCC, also found in seven clones. The T loop sequences of the two remaining clones contained single transition mutations of the two major sequences, UUCG UCC and UUCACCC. By contrast, no significant sequence-related bias was seen in the sequence of five nucleotides in the variable loop.

In addition to the sequences in the T and variable loops that were selected from the totally randomized sequence, a considerable number of mutations were introduced into the EGS in the chimeric substrates as a consequence of the conditions for PCR. Some of these mutations were beneficial and, therefore, the sequences that included them were selected and accumulated. In almost all of the individual selected clones, the integrity of base-pairing in the anticodon stem was disrupted.

Table 1 shows the partial sequences of the anticodon loop/stem region, the variable (V) loop, and the T stem/loop region of the parent chimeric mRNA-EGS$^{CAT}$ substrate (P), nucleotides 28 through 88 of Sequence ID No. 1. Table 1 also shows partial sequences of EGS segments of some individual chimeric mRNA-EGS substrates, nucleotides 1 through 60 of Sequence ID No. 9 and Sequence ID Nos. 17 through 31, which were obtained as a result of the in vitro selection procedure. Nucleotides that differ from the parent chimeric mRNA-EGS$^{CAT}$ substrate sequence are given in bold letters and are underlined. Hyphens indicate deletions. The remaining part of the sequence of the mRNA-EGS chimeric substrates is shown in FIG. 4A. Numbering of the partial sequences is not uniformly consecutive, since some clones did not have appropriate inserts and only sixteen selected sequences are listed.

TABLE 1

| Substrate # (ID No.) 19 | D stem/ loop 30 | Anticodon stem/loop 47 | V loop 52 | T stem/ loop 69 | AA stem |
|---|---|---|---|---|---|
| SCE-1 (28–88 of 1) | GGCCAAACUGA | GCAGACUCUAAAUCUGC | NNNNN | GAAGGUUCNNNNCCUUC | AUGCCUCACCA |
| #1 (17) | GGCCAAACUGA | GCAGACUCUAAAUCGGC | CCUUC | GAAGGUUCGCCCCCUUC | AUGCCUCACCA |
| #2 (18) | GGCCAAACUGA | GCAGACUCUAAAUCUGC | ACGAGA | GAAGGUUCGUGCCCUUC | AUGCCUCACCA |
| #4 (19) | GGCCAAACUGA | GCAGACUCUAAACUGGC | CUAAC | GAAGGUUCGCCCCCUUC | AUGCCUCACCA |
| #5 (20) | GGCCAAACUGA | GCAGACUCUAAAU-UGC | CCAAC | GAAGGUUCACCCCCUUC | AUGCCUCACCA |
| #6 (21) | GGCCAAACUGA | GCAGACUCCAAAUC--C | ACCAA | GAAGGUUCGUGCCCUUC | AUGCCUCACCA |
| #8 (22) | GGCCAAACUGA | GCAGACUCUAAA-CUCC | UCCCA | GAAGGUUCGUGCCCUUC | AUGCCUCACCA |
| #9 (1–60 of 9) | GGCCAAACUGA | GCAGACUCUAAAUC-GC | AAACG | GAAGGUUCGUGCCCUUC | AUGCCUCACCA |
| #10 (23) | GGCCAAACUGA | GCAGACUCUAAAUCGGC | CUACG | GAAGGUUCGCCCCCUUC | AUGCCUCACCA |
| #11 (24) | GGCCAAACUGA | GCAGACGCUAAAUCUAC | CCCGU | GAAGGUUCGUCCCCUUC | AUGCCUCACCA |
| #12 (25) | GGCCAAACUGA | GCAGACUCUAAAUUUGC | CACCA | GAAGGUUCGCCCCCUUC | AUGCCUCACCA |
| #13 (26) | GGCCAAACUGA | GCAGACUC-AAAUCUGGC | CAUUC | GAAGGUUCGCCCCCUUC | AUGCCUCACCA |
| #14 (27) | GGCCAAACUGA | GCAGACUCUAAAUC-GC | AGUGU | GAAGGUUCGUGCCCUUC | AUGCCUCACCA |
| #15 (28) | GGCCAAACUGA | GCAGACUCUAAAUCAGC | GCGUG | GAAGGUUCGUGCCCUUC | AUGCCUCACCA |
| #16 (29) | GGCCAAACUGA | GCAGACUCUAAAUCGGC | CGCAC | GAAGGUUCGCCCCCUUC | AUGCCUCACCA |
| #17 (30) | GGCCAAACUGA | GCAGACACUAAAUUUGC | ACGAG | GAAGGUUCGCCCCCUUC | AUGCCUCACCA |
| #18 (31) | GGCCAAACUGA | GCAGACCCUAAAUCUGC | CCCCG | GAAGGUUCGUGCCCUUC | AUGCCUCACCA |

E. Synthesis and Analysis of Individual EGS RNAs Based on Selected Chimeric Substrates The best chimeric substrate selected was clone 9 whose corresponding RNA sequence is partially shown in sequence 9 (nucleotides 1 through 60 of Sequence ID No. 9) in Table 1. The clone 9 chimeric substrate was cleaved about 5.5 times more efficiently than the parent, non-randomized, chimeric substrate, mRNA-EGS$^{CAT}$ chimera. Using the sequences of the selected chimeric substrates, nine individual corresponding EGS RNAs were synthesized: EGS-1 (Sequence ID No. 17), EGS-4 (Sequence ID No. 19), EGS-5 (Sequence ID No. 20), EGS-6 (Sequence ID No. 21), EGS-8 (Sequence ID No. 22), EGS-9 (nucleotides 1 through 60 of Sequence ID No. 9), EGS-12 (Sequence ID No. 25), EGS-14 (Sequence ID No. 27) and EGS-18 (Sequence ID No. 31), in order to probe the function of these selected EGSs in directing RNase P to the target CAT mRNA.

Each of the individual EGS RNAs was mixed with $^{32}$P-labeled CAT mRNA and the mixtures were then exposed to RNase P. Every selected EGS RNA increased the initial rate of the cleavage reaction, as measured during the linear phase of the reaction, over that with EGS$^{CAT}$, and cleavage occurred at the expected site in the target mRNA, as demonstrated by FIG. 5.

The most dramatic improvement in rates occurred with the EGS sequence based on clone 9, EGS 9 (nucleotides 1 through 60 of Sequence ID No. 9), which directed cleavage of the CAT mRNA at an overall rate more than 30 times faster than that observed with EGS$^{CAT}$ in the complex. The three most efficient EGSs tested, derived from clone 6, clone 8 and clone 9; all had a common sequence, UUCGUGC, in the T loop.

F. Secondary Structural Analysis of mRNA-EGS Complexes

The proposed secondary structure of the complex of CAT mRNA and EGS 9 (Sequence ID No. 9) (FIG. 4B) can be compared with the parent CAT mRNA-EGS$^{CAT}$ complex (FIG. 4A). The structures of CAT mRNA-EGS complexes were confirmed in part by partial digestion with RNases T1 and T2 under conditions that allowed formation of the mRNA-EGS complex and identification of single-stranded regions in RNA. Partial digestion of CAT mRNA-EGS complexes with RNases T1 and T2 (Pharmacia) were performed in RNase P assay buffer (50 mM Tris-HCl (pH 7.5), 10 MM MgCl$_2$, and 100 mM NH$_4$Cl). The reaction mixture contained substrate RNA labeled with [$^{32}$p] at its 5' terminus (2000 cpm), 0.2 mg/ml of rat 5S RNA as carrier, and three different concentrations, $2\times10^{-4}$, $1\times10^{-3}$ and $5\times10^{-3}$ units/ml, of RNase T1 or RNase T2. Reactions were incubated at room temperature for 5 min. The samples were analyzed by PAGE in 12.5% sequencing gels. Double-stranded regions were identified by digestion with cobra venom nuclease (Pharmacia, Alameda, Calif.). Conditions for digestion with cobra venom nuclease were as described above for RNase T1 and T2 except that incubation was at 37° C.

Figure 4B:
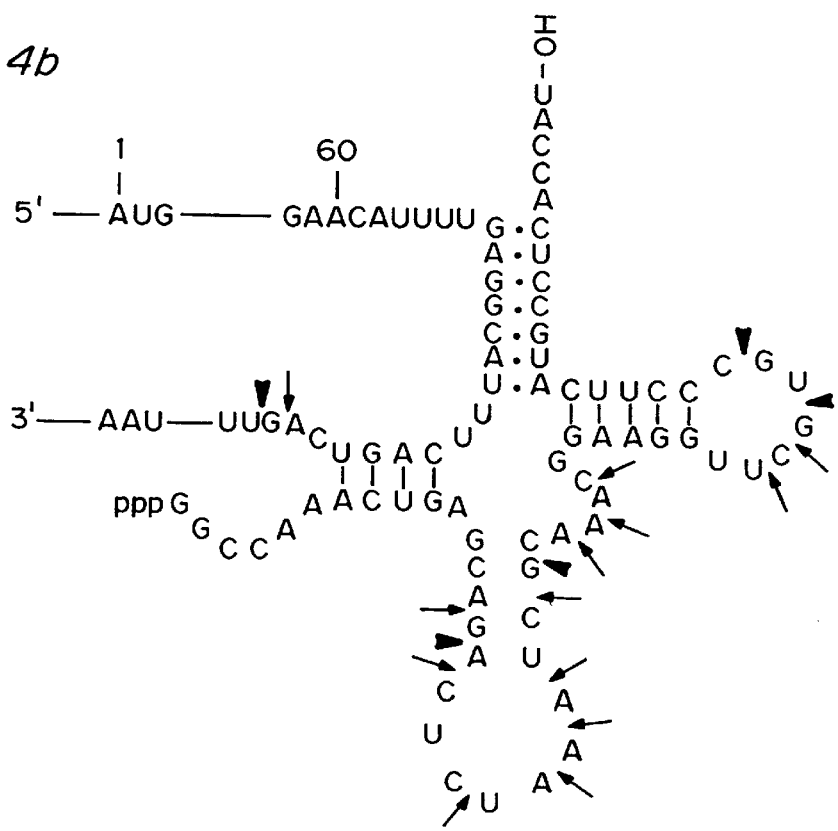
Figure 4C:
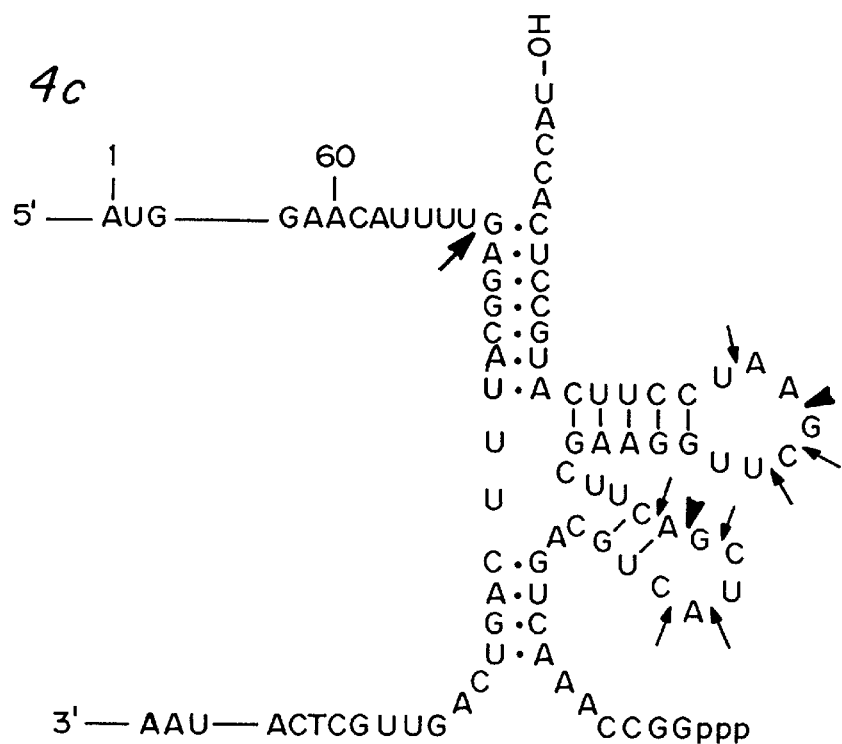
Figure 4D:
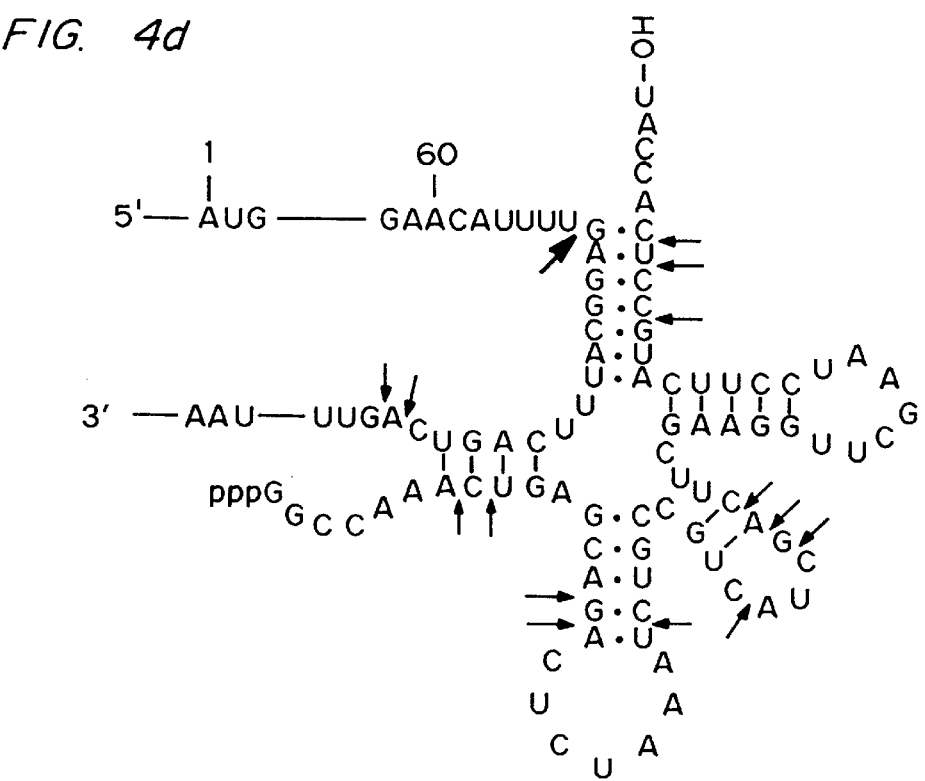
Figure 4E:
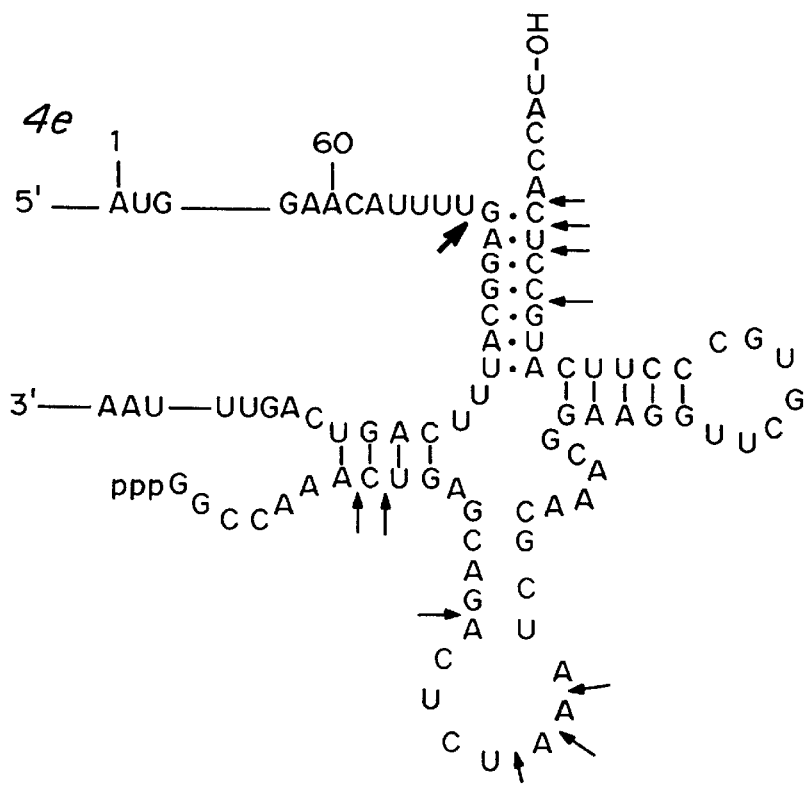
Figure 4F:
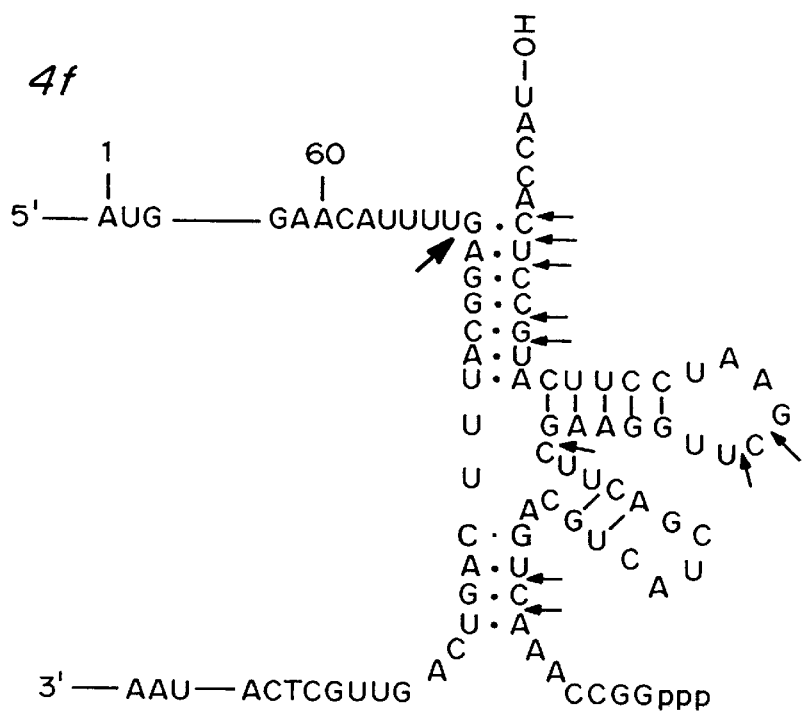

The sites of cleavage by the various nucleases in CAT mRNA-EGS$^{CAT}$ complex are indicated by solid arrows in FIGS. 4A and 4D. The tRNA domain in this structure is very similar to that found in a natural tRNA. The results obtained with cobra venom nuclease indicate that the first few nucleotides in the analog of the D loop are involved in a tertiary interaction, presumably with nucleotides in the variable loop (FIG. 4D). This interaction is either absent or much less extensive in the complex with EGS 9 (Sequence ID No. 9) (FIG. 4E) and, indeed, the same region in the analog of the D loop is susceptible to attack by RNases T1 and T2, an indication that it is in a single-stranded conformation (FIG. 4B). This result, together with the appearance of new sites of susceptibility to attack by cobra venom in the anticodon loop of EGS 9 confirm that this EGS endows the complex of the EGS and CAT mRNA with new tertiary interactions that enhance the rate of cleavage by RNase P. The results of cleavages by nucleases also confirmed that the anticodon stem in EGS 9 was disrupted as a result of a single nucleotide deletion. EGSs 9 and 14 are not similar to each other in terms of their efficiency in directing RNase P to a target substrate. The only difference in their nucleotide sequences is in the variable loop, as shown by Table 1. This difference alone must account for the relative inefficiency of EGS 14 in terms of targeting ability. Furthermore, digestion with RNase T1 of the complex that contained EGS 9 revealed strong protection of the last nucleotide, G, in the variable loop from attack by RNase T1, as shown by FIG. 4B. The role of this G may be similar to that played by nucleotide 57 in tertiary interactions in tRNA molecules; namely, the G may form hydrogen bonds with a nucleotide in the CAT mRNA sequence to ensure folding of the "tRNA" domain of the mRNA sequence.

G. Anticodon Stem and Loop of an EGS Decrease Cleavage Rate of RNase P and are Dispensable An independent study of recognition of precursor tRNA substrates by human RNase P showed that the anticodon stem and loop form a dispensable structural feature in the recognition of substrates by human RNase P. To determine whether the anticodon stem and loop may act in a negative fashion on the overall rate of cleavage of target. RNA by RNase P, two more EGS RNAs were constructed, one being a deletion mutant that lacked the equivalent of the anticodon stem and loop, EGS$^{CAT}$ΔAC (Sequence ID No. 10), as compared to the parent EGS$^{CAT}$ (FIG. 4A), and the other, EGS 19, being a derivative of EGS 9 in which the structure of the anticodon stem was restored.

DNA coding for EGS$^{CAT}$ΔAC was synthesized by PCR with pEGS$^{CAT}$ DNA, described by Yuan et al., *Proc. Nat. Acad. Sci. USA* 89: 8006 (1992), as template. Oligonucleotide EC-1ΔAC (GCCAAACTG ACGTCATCGACTTCG, Sequence ID No. 32) and M13 reverse primer (AACAGCTATGACCATG, Sequence ID No. 33) were used as primers. The DNA generated by PCR was digested with HindIII and then inserted into pUC19 downstream from a T7 RNA polymerase promoter sequence. EGS$^{CAT}$ΔAC RNA (Sequence ID No. 10) was prepared by transcription in vitro after the new plasmid DNA had been linearized with DraI. DNA that coded for EGS 19 was synthesized by PCR procedure in a manner similar to that used for the synthesis of DNA for EGS 9, with oligonucleotides SEC-1C (Sequence ID No. 15) and SEC-1I (GTAATACGACTCACTATAGGCCAAACTGAGCAGA-CTCTAAATC<u>T</u>GCAAACGGAAGGTTC, Sequence ID No. 34): the newly inserted T residue in SEC-1I is underlined. The DNA was transcribed in vitro with T7 RNA polymerase to give EGS 19 RNA. EGS 19 (Sequence ID No. 39) RNA differs from EGS 9 RNA only in the additional U that restores the structure of the anticodon stem.

Figure 5:
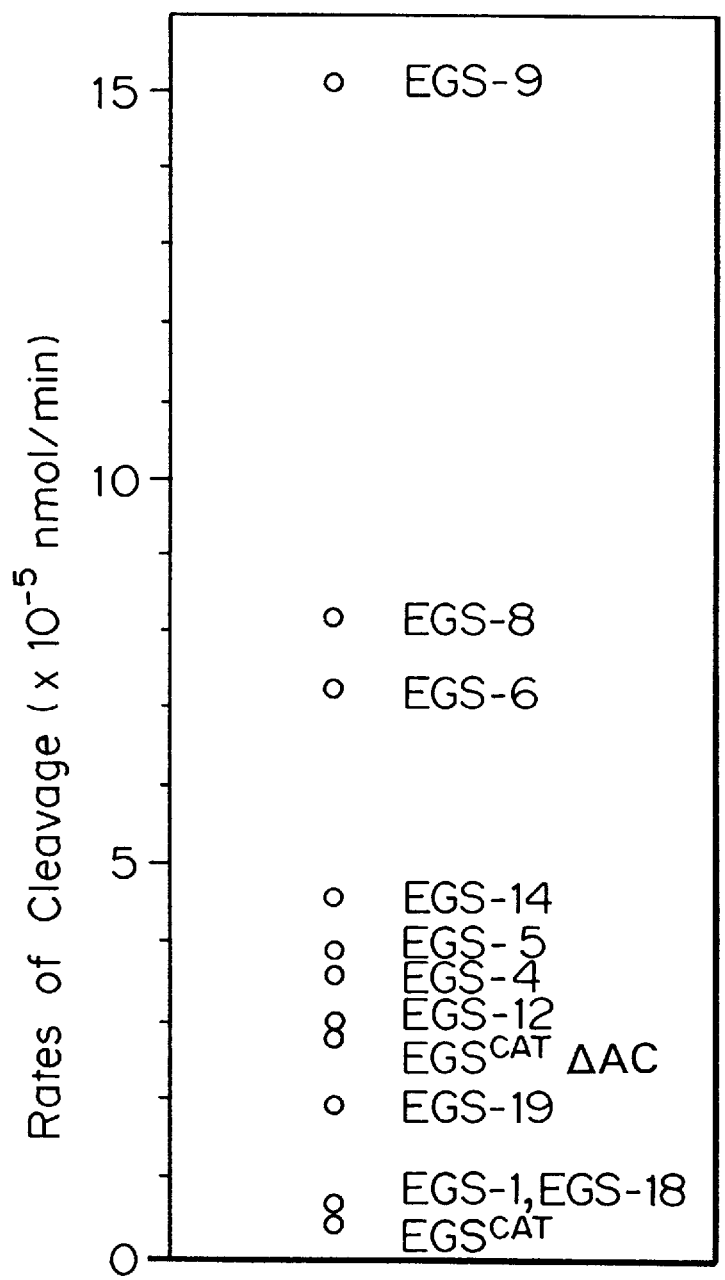
FIG. 5 shows rates (nmol/min) of human RNase P cleavage of CAT mRNA directed by twelve individual EGS RNAs. Nine individual EGS RNAs: EGS 1 (Sequence ID No. 17), EGS 4 (Sequence ID No. 19), EGS 5 (Sequence ID No. 20), EGS 6 (Sequence ID No. 21), EGS 8 (Sequence ID No. 22), EGS 9 (Sequence ID No. 9), EGS 12 (Sequence ID No. 26), EGS 14 (Sequence ID No. 27), EGS 18 (Sequence ID No. 31), were prepared by in vitro selection. EGS 19 and EGS$^{CAT}$ΔAC (Sequence ID No. 10) were prepared by in vitro mutagenesis. Results are presented as initial rates (nmol/mol) of cleavage of substrate by RNase P during the linear phase of each reaction.

In EGS$^{CAT}$ΔAC (Sequence ID No. 10), the length of EGS$^{CAT}$ was reduced by 25%: the shorter deletion mutant directed cleavage of target RNA about six times more efficiently than the parent EGS, as shown by FIG. 5. Restoration of the anticodon-stem structure, as in EGS 19, reduced the rate of cleavage of the target RNA with EGS 19 to four times lower than that with EGS 9. These results, together with the measurement of the rates of reaction with EGSs selected in vitro, indicate a significant inverse correlation between the efficiency of an EGS in the cleavage reaction and the existence of an anticodon stem in EGS RNA.

H. Stability of EGS-mRNA Complexes

The stability of EGS-mRNA complexes was measured based on both the binding constants between the mRNA and each EGS and the dependence on Mg$^{2+}$ ions of the cleavage reaction, presuming that relatively high concentrations of Mg$^{2+}$ ions were needed to stabilize relatively unstable complexes. The dissociation constants (K$_d$) of mRNA-EGS complexes were measured directly by a gel mobility shift assay in polyacrylamide gels that contained 10 mM Mg$^{2+}$ ions according to the method of Pyle et al., *Proc. Natl. Acad. Sci. USA* 87: 8187–8191 (1990). A fragment of CAT mRNA, 160 nucleotides in length, was prepared by transcription with T7 RNA polymerase in the presence of [α-$^{32}$P]GTP. 10 μl EGS RNA in 2X binding buffer was heated at 80° C. for 4 min before it was mixed with an equal volume of 2 nM CAT mRNA fragment in water. 1X binding buffer contains 50 mM Tris-Cl (pH 7.5), 10 mM MgCl$_2$, 100 mM NH$_4$Cl, 3% glycerol, 0.05% xylene cyanol. The mixtures were incubated at 37° C. for 20 min and immediately separated on 5 % polyacrylamide gels at 9 watts. The electrophoresis buffer consisted of 36 mM Tris base, 64 mM HEPES, 0.1 mM EDTA, 10 mM MgCl$_2$ (pH 7.5 without any adjustment). Quantitation of free target RNA and of the complex was performed with a Betascope (Betagen, Waltham, Mass.). The free energies of binding were determined from the equation αG°=—RT ln (1/K$_d$), where R=0.00198 kcal/mol and T=310.15° K.

The dissociation constants for selected EGSs are shown in Table 2.

TABLE 2

Dissociation constants of EGSs.

| Substrates | $K_d$ (nM) | $K_m$ (nM) | $V_{max}$ (nmol/min) × $10^{-5}$ | $V_{max}/K_m$ × $10^{-6}$ |
|---|---|---|---|---|
| pTyr | | 10 | 2.9 | 2.90 |
| CAT mRNA + EGS$^{CAT}$ | 880 | 120 | 2.9 | 0.24 |
| (Sequence ID No. 8) + EGS$^{CAT}$ ΔAC | 20 | 150 | 11.4 | 0.76 |
| (Sequence ID No. 10) + EGS-5 | 210 | 125 | 16.3 | 1.30 |
| (Sequence ID No. 20) + EGS-8 | 25 | 125 | 21.3 | 1.70 |
| (Sequence ID No. 22) + EGS-9 | 78 | 125 | 30.0 | 2.40 |
| (nucleotides 1–60 of Sequence ID No. 9) + EGS-19 | 710 | 130 | 12.5 | 0.96 |

Table 2 shows the kinetic parameters of EGS-directed cleavage of CAT mRNA in vitro by RNase P from HeLa cells. $K_d$ refers to measurements of the dissociation constant for binding of EGS to CAT mRNA. The other parameters were determined in standard assays of enzyme kinetics. $V_{max}$ is the value obtained with 0.5 ml (0.6 units) of human RNase P. pTyr refers to the precursor to tRNA$^{Tyr}$ from E. coli.

The results shown in Table 2 indicate that the $K_d$ values of in vitro selected EGSs are 4 to 40 times lower than that of the parent EGS. Thus, the selected EGSs had higher affinity for the target RNA than did EGS$^{CAT}$. The chimeric substrate derived from clone 9 was cleaved by RNase P at a rate only about 1.5 times faster than was the target in the mRNA-EGS 9 complex, an indication that the ability of the EGS to bind tightly to the target RNA in solution must be a critical determinant in the efficiency of the substrate complexes.

The differences in $K_d$ values between complexes with EGS$^{CAT}$ (Sequence ID No. 8) and the selected EGSs correspond to the contribution of –1 to –2.4 kcal/mol to the free energy of binding ($\alpha G°$) with selected EGSs ($\alpha G°$) is –8.5 kcal/mol for the complex with EGS$^{CAT}$, –10.1 for the complex with EGS 9 (Sequence ID No. 9) and –10.9 for the complex with EGS$^{CAT}$ΔAC (Sequence ID No. 10), thus revealing new interactions in the selected EGS-mRNA complexes.

Deletion of the anticodon stem from EGS$^{CAT}$ resulted in the $K_d$ for EGS$^{CAT}$αAC being 44 times lower, and restoration of the stem of EGS 9 (EGS 19) resulted in a $K_d$ that was ten times higher than that for EGS 9 and was close to that of EGS$^{CAT}$ (Table 2). Thus, the intact anticodon stem stabilized a conformation of the EGS that could bind as strongly to the target RNA as does an EGS with no organized anticodon stem. Accordingly, the enhancement of the ability of the selected EGSs for targeting RNA can be assigned, in part, to the increase in the strength of their binding to target RNA.

Cleavage of mRNA directed by the original EGS$^{CAT}$ requires Mg$^{2+}$ ions with an optimum concentration of 25 mM. By contrast, the reaction with certain selected EGSs, namely, EGS 6 (Sequence ID No. 21) and EGS 9 (nucleotides 1 through 60 of Sequence ID No. 9), proceeds optimally in 2 to 10 mM Mg$^{2+}$ ions. This latter concentration is close to the optimal concentration of Mg$^{2+}$ ions for processing of tRNA precursors by human RNase P, reported by Doersen et al., J. Biol. Chem. 260: 5942 (1985). Since high concentrations of Mg$^{2+}$ ions are especially effective in the neutralization of repulsion between adjacent regions of the phosphate backbone and the stabilization of RNA folding, the results indicate that the selected EGSs can achieve the appropriate folded structures in the complex with target RNAs without the aid of high concentrations of Mg$^{2+}$ ions.

A kinetic analysis was performed to determine the Michaelis constant ($K_m$) and the maximum velocity ($V_{max}$) of the enzymatic reactions. The cleavage of the precursor to tRNA$^{Tyr}$ from E. coli and of CAT mRNA in mRNA-EGS complexes was assayed at various substrate concentrations both above and below the $K_m$ for these substrates. Aliquots were withdrawn from reaction mixtures at regular intervals and analyzed on polyacrylamide-urea gels. Values of $K_m$ and $V_{max}$ were obtained from Lineweaver-Burk double-reciprocal plots. The effective concentrations of substrate used were calculated as the concentration of the complex of target mRNA with EGS as determined from the $K_d$ values shown in Table 2. The $K_m$ for the precursor to tRNA$^{Tyr}$ (pTyr) is 10 nM with human RNase P, whereas the $K_m$ value of the complex of mRNA-EGS$^{CAT}$ is twelve-fold higher (Table 2). The $K_m$ for all the selected EGSs tested was the same as that of EGS$^{CAT}$. However, the maximum velocities of the reactions with selected EGSs were up to ten times higher than that with the original EGS. Thus, the value of $V_{max}/K_m$ for selected EGSs was increased. The value of $V_{max}/K_m$ of EGS 9, was for example, ten-fold higher than that of EGS$^{CAT}$ and was very close to that of the tRNA$^{Tyr}$ precursor. When the anticodon stem of EGS 9 was restored, however, as it was in EGS 19, $V_{max}$ fell about 2.5-fold, suggesting that the rate of release of the product was specifically reduced by physical interactions of the enzyme with an intact anticodon stem. These data show that the enhanced abilities for targeting of the selected EGSs, as measured in the overall rate of the cleavage reaction, were due to both enhanced affinity of binding to substrate RNAs and to increases in the velocity of the enzymatic reaction.

EXAMPLE 6

Inhibition of Viral mRNA with Human Ribonuclease P

Herpes simplex virus was used to demonstrate that EGS can be used to target a viral gene in vivo to inhibit viral replication. Herpes simplex viruses are DNA-containing viruses that infect cells, induce synthesis of messenger RNAs, which are transcribed to produce enzymes related to DNA synthesis and breakdown: including thymidine kinase, DNA polymerase and a DNA exonuclease, and viral DNA and viral structural proteins are made and assembled into infectious viral particles. The structure and organization of the herpes simplex virus genome is known, for example, as reported by Roizman, Cell 16: 481–494 (1979). The nucleotide sequence of the thymidine kinase gene of herpes simplex type 1 was described by Wagner et al., Proc. Natl. Acad. Sci. USA 78: 1441–1445 (1981).

Figure 6A:
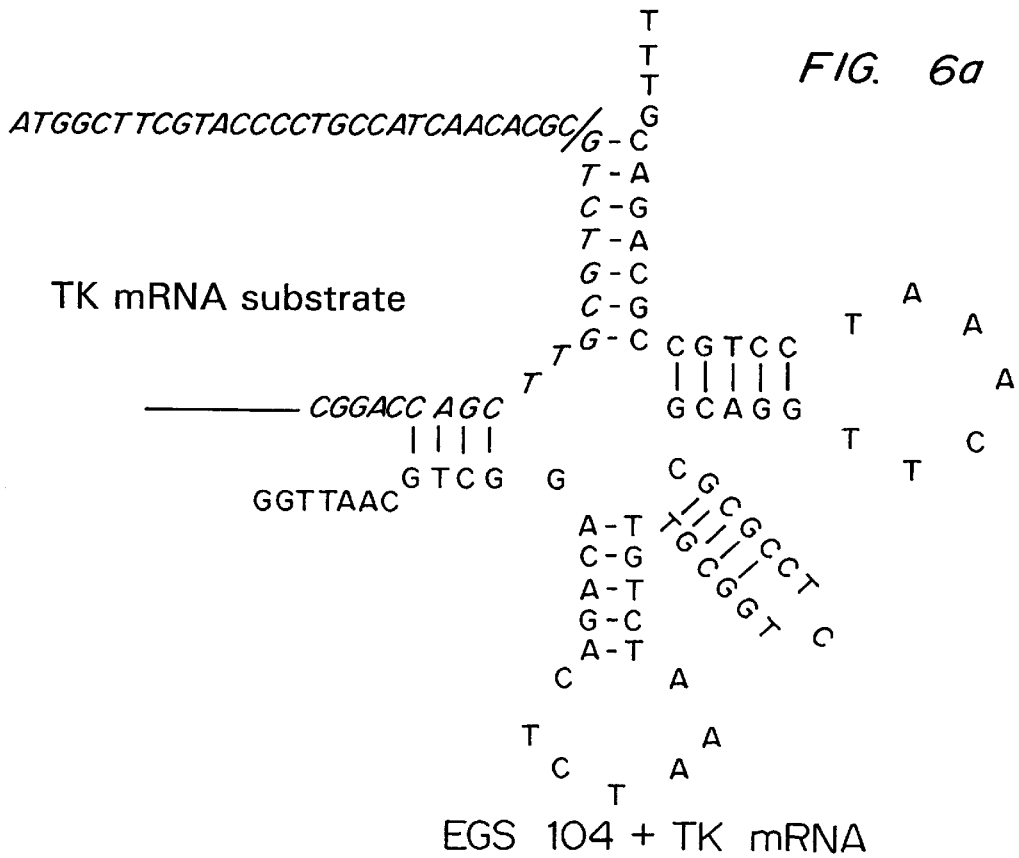
FIGS. 6A, 6B, and 6C are sequence and proposed secondary structures of EGS for herpes simplex virus thymidine kinase mRNA (Sequence ID No. 35).
Figure 6B:
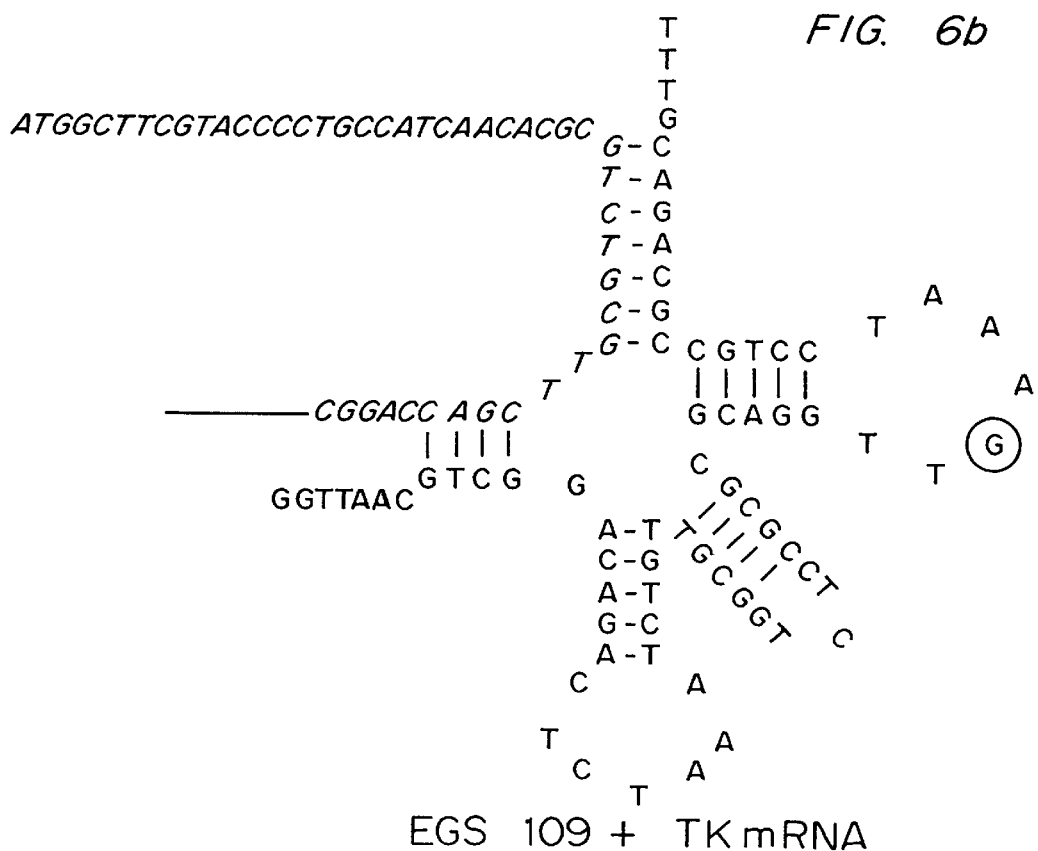
Figure 6C:
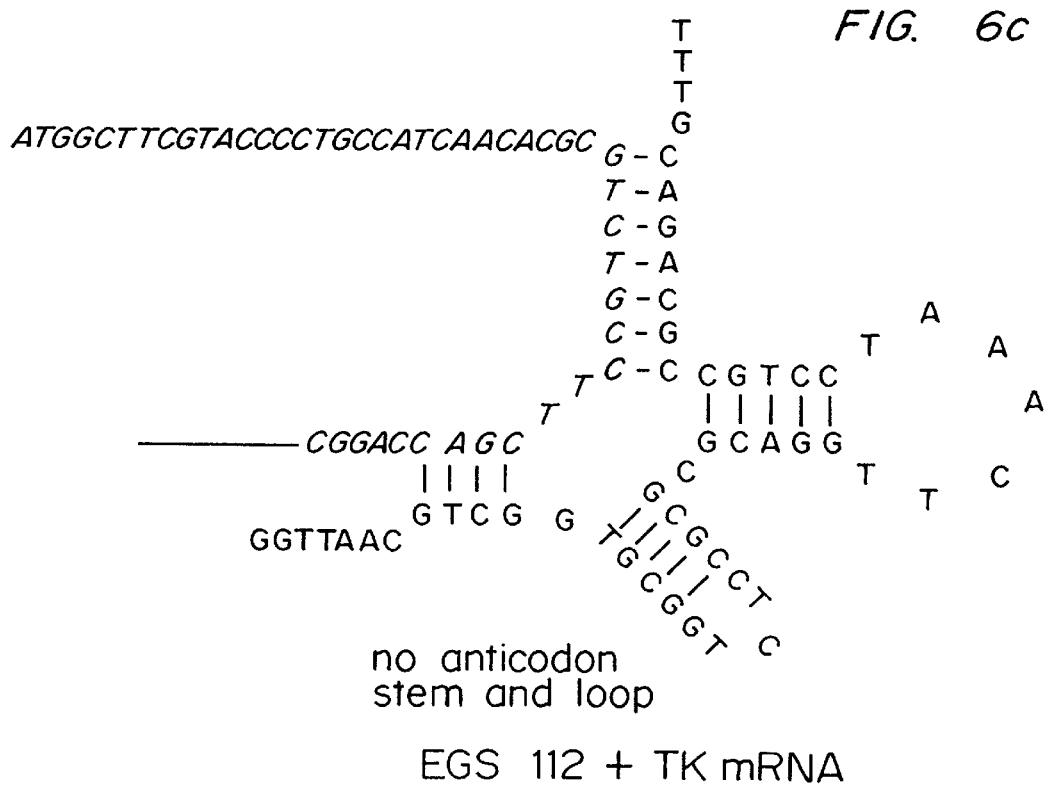

An EGS, shown in FIG. 6A, was designed to target the mRNA encoding thymidine kinase (TK). The target site for RNase P cleavage is about 25 nucleotides downstream from the TK translation initiation site. An EGS forming an approximately three-fourths-like tRNA was designed and shown in vitro to cleave the TK sequence at the proposed cleavage site. Two other EGSs, which contain a single point mutation in the T-loop (C to G) or deletion of the anti-codon region, shown in FIGS. 6B and 6C, respectively, were constructed based on the results observed in Example 5.

Cell lines and EGS expression vectors were then constructed. Five cell lines were constructed by transfecting plasmid DNAs into human 143TK-cells, which can be obtained from the American Type Culture Collection, Rockville, Md.

Plasmid pFL116 was constructed using pGEM-7Z (Promega, Wis.) and incorporating a gene for neomycin resistance (Neo), which is commercially available from Clontech or Stratagene, Calif. EGS DNA (FIGS. 6A, 6B, and 6C) was digested with KpnI and inserted into the plasmid pmU6(-315/1), described by Yuan et al., *Proc. Natl. Acad. Sci. USA* 89: 8006–8010 (1992) and Das et al., *EMBO* 7: 503–512 (1988), at the PstI (blunted)/KpnI site. This plasmid contains the promoter for the gene for U6 small nuclear RNA, a very strong promoter, and a signal for termination of transcription (T cluster) by RNA polymerase II. EGS plasmids were designated pFL104, pFL109, and pFL112, respectively. The plasmid based on sequence 9 in Table 1 was used as a control.

The cells were stably transfected using a calcium phosphate precipitation method described by Wigler et al., *Proc. Natl. Acad. Sci. USA* 76: 1373–1376 (1979), with the pFL116 to yield CL116, plasmids EGS 9 and pFL116 to yield CLCAT, plasmids pFL104 and pFL116 to yield CL104, plasmids pFL109 and pFL116 to yield CL109, and plasmids pFL112 and pFL116 to yield CL112, followed by neomycin selection. Cells were cloned, expanded and RNA isolated. Both total and cytoplasmic RNA was isolated and the RNase protection method described in "Molecular Cloning: A Laboratory Manual, Second Edition" Sambrook et al., (Cold Spring Harbor Laboratory Press, 1989) at pages 7.71–7.78. This is an extremely sensitive assay where digestion of RNA:RNA hybrids formed using radiolabelled probe is used to assess which cell clones express the EGS.

The results indicated that the EGSs are expressed in both nuclei and cytoplasm.

Cells were then infected with herpes simplex virus using a multiplicity of infection (MOI) of 1 to 1.5, specifically, 1 to 1.5 million viral particles/i million cells, in order to resemble a natural infection with virus. RNA was harvested at 4, 8 and 12 hours post-infection. The internal control probe was used to detect the mRNA levels of HSV α47 and late genes $U_5 10$ and $U_5 11$. The probe is selected to assure the detection of a high level of viral mRNA expression over the entire cycle of viral infection.

Figure 7:
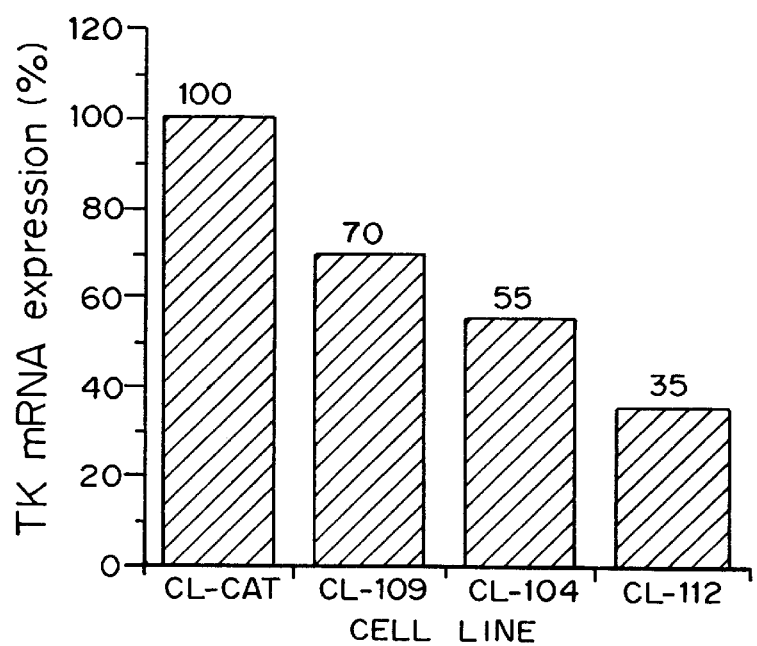
FIG. 7 is a graph of percent TK mRNA expression for cell lines: CL-CAT, CL-109, CL-104, and CL-112.

The results are shown in FIG. 7. TK mRNA expressed was decreased 0% in the control CL-CAT, 30% in CL-109, 45% in CL-104, and 65% in CL-112.

EXAMPLE 7

RNase P Internal Guide Sequences
A. Construction of plasmids, catalytic RNAs and RNA substrates for studies in vitro DNA templates for transcription in vitro of RNA substrates tk7, tk46, and cat7 were constructed by annealing the T7 promoter containing oligonucleotide, OliT7 (5'-TAATACGACTCACTATAG-3') (Sequence ID No. 41) with oligo-nucleotides Olitk7 (5'-CGCAGAC GGTCCTATAGTGAGTCGTATTA-3') (Sequence ID No. 42), OliTK46 (5'-ACCGCCGC- AGCCTGGTCGAACG-CAGACGCGTGTTGATGGCAG GGGTCTATAGTGAGTCGTATTA-3') (Sequence ID No. 43), and Olicat7 (5-ATGCCTCGGTCCTATAGTGAGTCGTATTA-3') (Sequence ID No. 44), respectively. Plasmids pTK117 and pTK146 are derivatives of pUC19 and were described by Guerrier-Takada and Altman, *Proc. Natl. Acad. Sci. USA* 89: 1266–1270 (1992). The DNA sequences coding for M1 RNA (pTK117) and mutant M1 RNA with a deletion from nucleotides 167 to 377 (pTK146), are under the control of the T7 RNA polymerase promoter. The DNA templates for M1TK19, M1TK16, M1TK13, M1TK10, M1TK5, and M1CAT13 were constructed by the polymerase chain reaction (PCR) with the gene for M1 RNA as found in plasmid pTK117 with OliT7 as the 5'primer oligonucleotide and 3' primers that contained the appropriate guide sequences. The 3' primers were OliTK19 (5'-GTGGTGTCTGCGTTCGACCAGGCTATGAC CATG-3') (Sequence ID No. 45), OliTK16 (5' GTGGTGTCTGCGTTC GACCAGTATGACCATG-3') (Sequence ID No. 46), OliTK13 (5'-GTGGTGTCTGCGTTCTATGACCATG-3') (Sequence ID No. 47), OliTK10 (5'-GTGGTGTCTGCGTTCTATGACCATG-3') (Sequence ID No. 48), OliTK5 (5'-GTGGTGTCTGTATGACCATG-3') (Sequence ID No. 49), and OliCAT13 (5'-GTGGTGAGGCATTTCAGTTATGAC CATG-3') (Sequence ID No. 50). The 3' proximal sequences of 10 no serve as the primers for the PCR with the pUC19 sequence. The underlined sequences and the bold sequences correspond to the 3° CCAC sequence and the guide sequences, respectively. The DNA template for ΔM1(167–377)TK13 RNA was constructed by PCR with the sequence for M1 RNA in pTK146 and primers OliT7 and OliTK13. The DNA template for EGS TK16 was constructed by PCR with the 5' primer OliT7 and the 3' primer OliTK16 for DNA template pUCT7, which was derived from pUC19 by insertion of a T7 promoter sequence into the BamHI site. The CAT mRNA fragment of 550 nt was synthesized with T7 RNA polymerase and EcoRI-digested pCAT-1 plasmid DNA (Promega Inc.) while the TK mRNA fragment of 450 nt was synthesized from plasmid pTK101 DNA in which the sequence for TK mRNA is under control of the T7 promoter.

B. Assays for cleavage by M1GS RNA.

RNA enzyme (20 nM) and substrate (50 nM), either uniformly labeled with [α-$^{32}$P]GTP or 5' end-labeled with [γ-$^{32}$P]ATP, were incubated for 30 mins at 37° C. or 50° C. in buffer A (50 mM Tris, pH 7.5, 100 mM NH$_4$Cl, 100 MM MgCl$_2$) or buffer B (50 mM Tris, pH 7.5, 100 mM NH$_4$Cl) that contained MgCl$_2$ at various concentrations. Reactions were stopped by the addition of 8M urea and the cleavage products were then separated on either 15% or 20% polyacrylamide gels that contained 8M urea. C5 protein and human RNase P protein were purified from *E. coli* and HeLa cells, respectively, as described previously by Vioque et al., *J. Mol. Biol.* 202: 835–848 (1988), and Bartkiewicz et al., *Genes & Dev.* 3: 488499 (1989). The RNase P holoenzyme from *E. coli* was assembled by mixing M1 RNA and C5 protein at a molar ratio of 1:20.

Assays to determine kinetic parameters under single- and multiple-turnover conditions were performed as described previously by Guerrier-Takada et al., *Cell* 35: 849–857 (1983), and Liu and Altman, *Cell* 77: 1083–1100 (1994). Cleavage was assayed at various concentrations of substrate, in 2- to 20-fold excess over enzyme concentration, both above and below the $K_m$ for the substrate. Aliquots were withdrawn from the reaction mixtures at regular intervals and the cleavage products were separated in polyacrylamide-urea gels. quantitation was carried out with a phosphorinager (Molecular Dynamics). The values of $K_m$ and $k_{cat}$ were obtained from Lineweaver-Burk double reciprocal plots. In single turnover experiments, trace amounts of substrates were used and the concentrations, 1 nM, were much lower than the $K_m$ (>80 nM). The concentration of enzyme ranged from 5 nM to 200 nM. The observed rate of cleavage ($k_{obs}$) was determined, and the value of $k_{cat}/K_m$ was obtained from the equation $k_{cat}/K_m=k_{obs}/[E]$, where [E] is the concentration of the enzyme.

C. Viruses, cells and antibodies.

The properties of HSV-1(F), a prototype of human herpes simplex virus 1 have been described by Ejercito et al., *J. Gen. Virol.* 2: 357–364 (1968). The retroviral vector LXSN, retroviral packaging cell lines, PA317 (amphotropic) and ψACRE (ectopic), and their maintenance and propagation were described by Miller and Rosman, *BioTechniques* 7: 980–990 (1989), and Danos and Mulligan, *Proc. Natl. Acad. Sci. USA* 85: 6460–6464 (1988). The rabbit polyclonal antibody against thymidine kinase of HSV-1 (F) was described by Liu and Summers, *Virology* 163: 638–642 (1988), and the mouse monoclonal antibody MCA406 against HSV-1 ICP35 protein was described by Liu and Roizman, *J. Virol.* 65: 206–212 (1991), and purchased from Harlan Bioproducts for Sciences Inc. (Indianapolis, Ind.). The secondary antibodies used in the Western blots, anti-rabbit or anti-mouse IgGs conjugated with horseradish peroxidase, were purchased from Vector Laboratories Inc. and Bio-Rad Inc., respectively.

D. Construction of plasmids for studies in vivo

The promoter sequence for U6 small nuclear RNA and a signal for the termination of transcription (T cluster) by RNA polymerase III, described by Yuan et al. (1992), were inserted into the EcoRI site for the retroviral vector LXSN, described by Miller and Rosman (1989), to create pRVO. Retroviral constructs PB2, M1TK and ΔM1TK were constructed by placing the DNA sequence that coded for the EGS with the ability to target the mRNA for influenza viral protein PB2, m1TK13 RNA and ΔM1(167–377)TK13 RNA under the control of the U6 promoter in plasmid pRVO, respectively. Plasmid pTK129 and pTK141 were constructed, respectively, by placing the BglII-MluI fragment (87 nt) of the HSV-1(F) BamHI Q fragment and BamHI-AccI fragment (181 nt) of the HSV-1 (F) BamHI Z fragment under the control of a phage T3 RNA polymerase promoter. These two fragments correspond to the sequences that encode the 5' sequence of TK mRNA and of the overlapping transcripts for the HSV-1 α47, Us10, and Us11 genes, respectively, as described by McMeoch et al., *J. Gen. Virol.* 69: 1531–1574 (1988).

E. Construction of cell lines

The protocols were modified from Miller and Rosman (1989). In brief, cells were transfected with retroviral vector DNAs with the aid of a mammalian transfection kit purchased from Stratagene Inc. (La Jolla, Calif.). Forty-eight hours post transfection, neomycin (Gibco-BRL) was added to the culture medium at a final concentration of 600 μg/ml. Cells were subsequently selected in the presence of neomycin for two weeks and neomycin resistant cells were cloned and allowed to proliferate in neomycin-containing medium, as described by Sambrook et al. (1989). The newly constructed cell lines, NB2, ≠M1TK, and M1LTK, and a control cell line in which cells were transfected with LXSN vector DNA, were indistinguishable in terms of cell growth and viability for up to two months. Finally, aliquots of these cells were either frozen for long-term storage in liquid nitrogen or used immediately for further studies in vivo.

F. Viral infection and preparation of RNA and protein extracts

Approximately $10^6$ cells in a T25 flask were either mock-infected or infected with HSV-1 in 1.5 ml of Medium 199 (M199; GIBCO) supplemented with 1% fetal calf serum. After 2 hours of exposure of cells to virus at 37° C., the medium was replaced with Dulbecco's modified Eagle's medium supplemented with 5% fetal bovine serum. The cells were incubated for 11 hours before harvesting for isolation of viral mRNA and/or protein. RNA and protein extracts were prepared from cells that had either been mock-infected with HSV-1, as described previously by Jenkins and Howett, *J. Virol.* 52: 99–107 (1984), and Liu and Roizman (1991).

G. RNase protection assay for viral mRNA expression

The RNA probes used to detect TK mRNA and the transcripts of the α47, Us10, and Us11 genes were synthesized in vitro with T3 RNA polymerase (Promega, Madison, Wis.) from the DNA templates pTK129 and pTK141, respectively, that had been linearized with EagI. RNase protection assays were performed as described previously by Yuan et al. (1992). The protected RNA products were separated in 8M urea 8% polyacrylamide gels and quantitated with a phosphorimager. quantitation was performed in the linear range of RNA detection.

H. Electrophoretic separation and staining with antibodies of polypeptides from infected cells Denatured, solubilized polypeptides from cell lysates were separated on SDS-9% [v/v] polyacrylamide gels. The separated polypeptides were transferred electrically to nitrocellulose membranes and allowed to react in an enzyme-linked immunoassay with antibodies against either mouse or rabbit IgG that had been conjugated with horseradish peroxidase after reaction with antibodies against HSV-1 TK or ICP35. The membranes were subsequently stained with the color-development substrate from peroxidase substrate kit purchased from Vector Laboratories Inc. or reacted with the chemiluminescent substrate in a LumiGLO™ chemiluminescence kit (Kirkegaard and Perry Laboratories Inc.) and subsequently subjected to exposure to X-ray film. Finally, the amounts of TK and ICP35 protein on the membrane were quantitated by scanning the films with a densitometer (Bio-Rad, Inc.). Quantitation was performed in the linear range of protein detection.

I. Cleavage of model substrates by M1GS RNA in vitro

Figure 9:
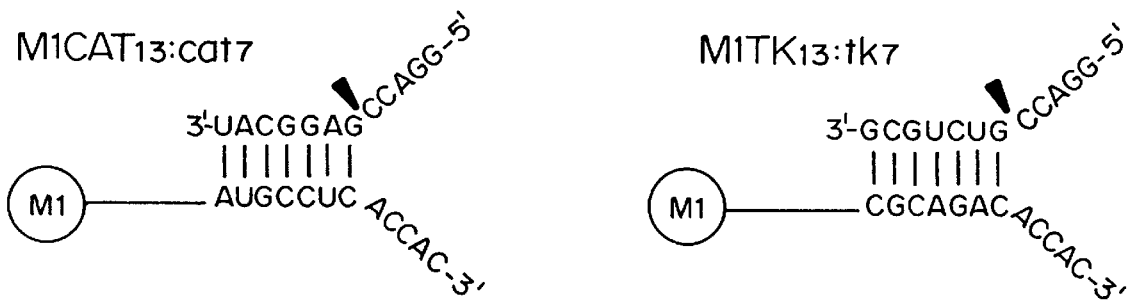
FIG. 9 is a schematic representation of complexes that are formed by M1 GS RNA (Sequence ID No. 51 and Sequence ID No. 52) and two substrates (Sequence ID No. 53 and Sequence ID No. 54).

The HSV-1 TK gene has been well characterized and is reviewed by Roizman and Sears, "Virology", 2nd edition, edited by Fields et al., pages 1795–1841 (Raven Press, New York, 1990). Although the TK gene product is not essential for viral replication in tissue culture cells, because it is so well studied we have used it as a model target for gene inactivation by M1GS RNA. DNA encoding a guide sequence (TK 13) that contains a sequence of 13 nt complementary to the 5' terminal sequence of mRNA for HSV-1 TK protein was covalently linked to the 3' end of DNA that encoded M1 RNA (FIG. 9). The RNA transcript of this construct, M1TK13, cleaved target RNA, tk7, that contains 7 nt of the 5' sequence of TK mRNA and an unrelated sequence of 5 nt that serves as a leader sequence (Sequence ID No. 52). Cleavage in the target occurs at position 5, yielding two cleavage products of 5 nt and 7 nt in length, respectively. M1TK13 remains unchanged during the reaction, as expected of a true enzyme, since only labeled, full-length M1TK13 RNA is detected after incubation of the reaction mixture. Attachment of guide sequences to the 3' end, rather than to the 5' end, of M1 RNA in the construction of M1GS RNA is preferred because the presence of a 3' terminal CCA sequence in the guide sequence is important for maximum efficiency of cleavage. Furthermore, additional sequences downstream from the CCA sequence lower the rate of cleavage of substrates.

Figure 10:
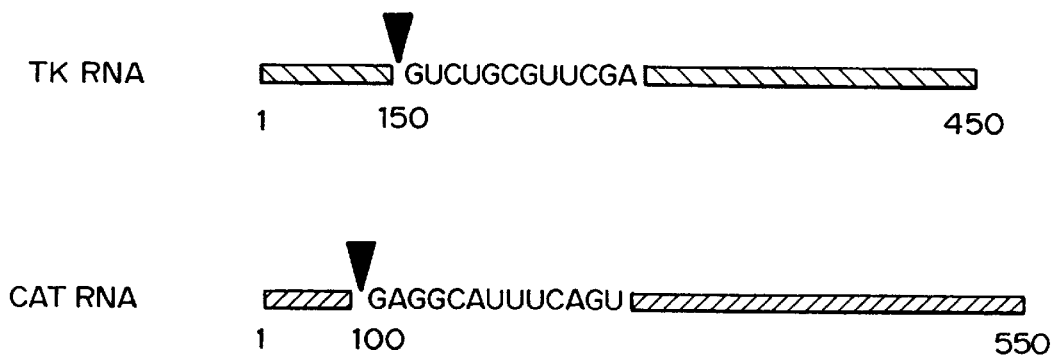
FIG. 10 is a diagram of TK and CaT RNA substrate RNAs. The two 13-nt segments highlighted in the TK RNA and CAT RNA sequences (Sequence ID No. 55 and Sequence ID No. 56) are complementary to the guide sequences in M1TK13 and M1CAT13 RNAs, respectively. The cleavage sites are indicated by arrows.

M1GS RNA only cleaves substrates that are complementary to the guide sequence. M1TK13 RNA can cleave substrate tk7 but not substrate cat7, which contains a sequence of 7 nt from the mRNA for chloramphenicol acetyltransferase (CAT). However, M1CAT13 RNA, in which the guide sequence contains a sequence of 13 nt complementary to CAT mRNA, can efficiently cleave cat7 but not tk7. Therefore, M1GS RNA appears to act as a sequence-specific endonuclease, recognizing its substrates through specific base-pairing between the GS and the target sequence, as has also been shown by Frank et al., *Biochemistry* 33: 10800–10808 (1994), with different constructs. To determine whether longer RNAs can be specifically cleaved by these new RNA enzymes, uniformly [$^{32}$P]-labeled fragments of the TK (450 nts) and CAT (550 nts) mRNA sequences (FIG. 10) were incubated with either M1TK13 RNA or M1CAT13 RNA. Sequence-specific and efficient cleavage of these RNA substrates by the appropriate RNA enzymes resulted.

Figure 11:
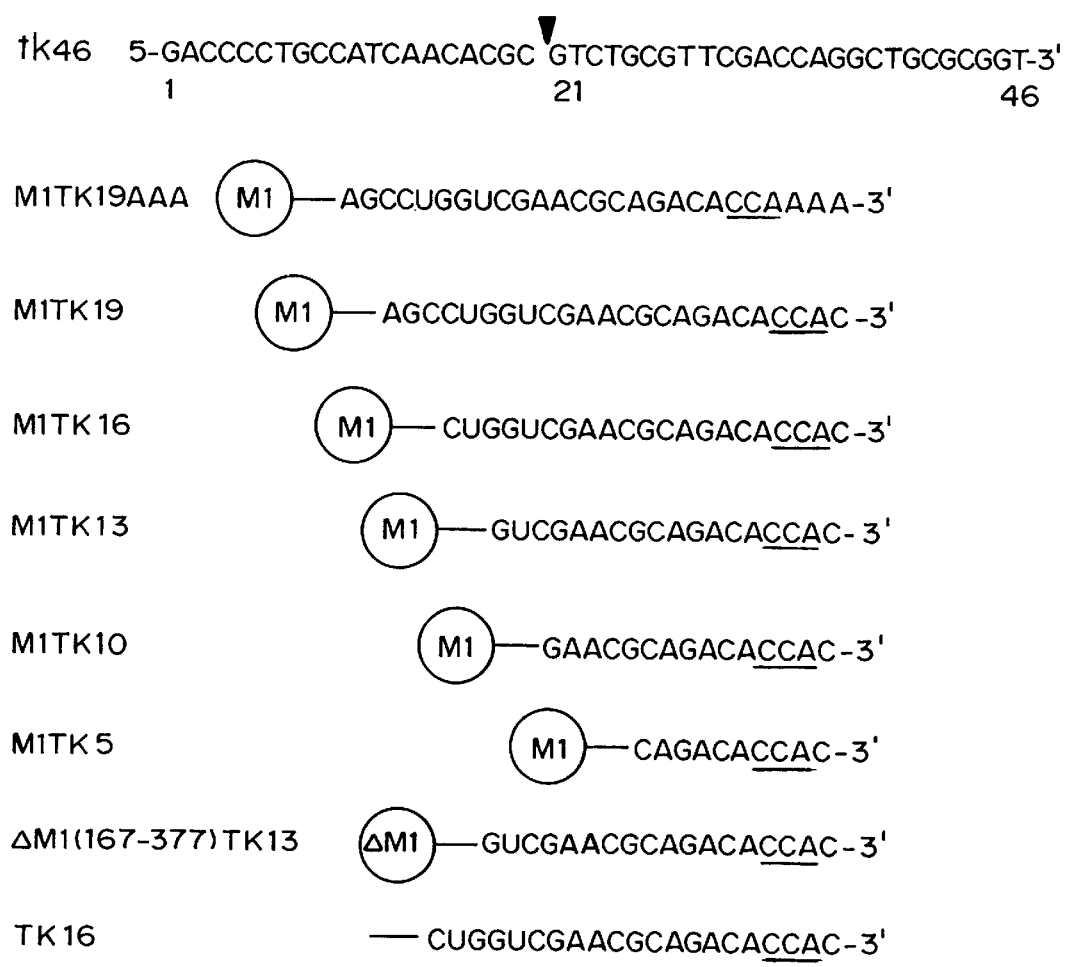
FIG. 11 is a schematic representation of the tk46 substrate sequence (Sequence ID No. 57) and the structure of RNA enzymes used (Sequence ID No. 58, Sequence ID No. 59, Sequence ID No. 60, Sequence ID No. 61, Sequence ID No. 62, Sequence ID No. 63, Sequence ID No. 64, and Sequence ID No. 65). The arrow marks the expected site of cleavage. The sequences shown in [the M1GS RNAs] bold type are the guide sequences that contain the 3' CCA sequence and the sequence complementary to the TK sequence.

A set of RNA enzymes, designated M1TK19, M1TK16, M1TK13, M1TK10 and M1TK5, were constructed in which the GSs contained sequences of 19, 16, 13, 10, 5 nucleotides complementary to the TK mRNA sequence, respectively (FIG. 11), in order to relate the length of the target helix to efficiency of cleavage. The substrate tk46, which contains a TK mRNA sequence of 46 nt, was cleaved by all the constructs and the cleavage site was determined to be at position G21, as expected (FIG. 11). Further kinetic analysis of cleavage of substrate tk46 by M1TK16, M1TK13, M1TK10, and M1TK5 RNAs was also performed and the results are shown in Table 3.

TABLE 3

Kinetic parameters of reactions catalyzed by various M1GS RNA constructs

| Enzyme | $K_2$ ($\mu$M) | $k_{cat}$ (min$^{-1}$) | $k_{cat}/K_m$ | $k_{cat}/K_m$* |
|---|---|---|---|---|
| M1TK16 | 0.08 | 0.14 | 1.6 | 2.4 |
| M1TK13 | 0.09 | 0.21 | 2.3 | 2.4 |
| M1TK10 | 0.15 | 0.10 | 0.7 | 0.7 |
| M1TK5 | 0.22 | 0.03 | 0.1 | 0.1 |

Values of $k_{cat}$ increased in the rank order from M1TK5 to M1TK16 RNA. Values of $K_m$ decreased progressively with increasing length of the duplex. The overall $K_m$ of the reaction undoubtedly involves both the substrate binding to the guide sequence (helix formation) and docking of the double helical segment in the active site of M1 RNA, a complex process. There was one exception to the rule of increasing $k_{cat}$ with length of guide sequence: $k_{cat}$ decreased from M1TK13 to M1TK16. This last result can be explained if release of product becomes the rate-limiting step in the reaction governed by M1TK16 RNA under single- and multiple-turnover conditions as described by Fersht, "Enzyme structure and mechanism", 2nd edition (W. H. Freeman and Co., New York, 1985). Further analysis of the reaction with M1TK13 showed that about 5 pmol of tk46 were cleaved by 1 pmol of M1TK13 in 30 minutes, indicating that the RNA enzyme turns over 5 times during the incubation period. This result is consistent with the value of $k_{cat}$ measured by classical Michaelis-Menten kinetic analysis (see Table 3).

M1GS RNAs act more efficiently than does M1 RNA in the classic cleavage reaction in trans. M1TK16 cleaves tk46 at least 10 times faster than does M1 RNA when using a separate guide sequence, TK16, under equivalent experimental conditions. Moreover, M1GS RNA cleaves its substrates more efficiently in buffers that more closely mimic physiological conditions in terms of magnesium ion concentration (10 mM MgCl$_2$) than does M1 RNA with a separated guide sequence in buffers that contain 100 MM MgCl$_2$, an indication that the high concentrations of Mg$^{2+}$ ions are needed to mediate binding of the substrate to M1 RNA alone, as indicated by Kazakov and Altman, *Proc. Natl. Acad. Sci. USA* 88: 9193–9197 (1991), and Smith and Pace, *Biochemistry* 32: 5273–5281 (1993). Further analysis of the cleavage reaction of M1GS RNA indicated that the cleavage proceeds optimally at a temperature of 62° C., at concentrations of monovalent cations of 100 mM, and at concentrations of Mg$^{2+}$ ions of 60–100 mM.

To prove that the catalytic activity of M1GS RNA resides in the sequence that encodes M1 RNA, a set of M1TK RNAs was constructed in which each RNA had a deletion in a different region of the M1 RNA sequence but in which each had the same guide sequence, TK13. The various M1 RNA deletion mutants, for example, Δ167–377, Δ1–163, and Δ65, lack the catalytic activity needed to process pre-tRNAs, as shown by Guerrier-Takada et al., *Science* 286: 1578–1584 (1989) and Guerrier-Takada and Altman (1992). M1GS RNA constructs with these deletion mutants and the linked TK13 sequence were unable to cleave tk46.

Stimulation of the activity of M1GS RNA by proteins

C5 protein, the protein subunit of RNase P from *E. coli*, increases the rate of cleavage of natural substrates by M1 RNA as described by Guerrier-Takada et al. (1983) and Reich et al., *Science* 239: 178–181 (1988). C5 protein also stimulates the cleavage by M1GS RNA by a factor of 30 or more. Furthermore, cleavage by M1GS RNA can be stimulated at least five-fold by a partially purified preparation of human RNase P. This enhancement in rate was anticipated as it had been previously shown that protein from a crude preparation of human (HeLa cells) RNase P can enhance the cleavage of ptRNA by M1 RNA as described by Gold and Altman, *Cell* 44: 243–249 (1986). The rate stimulation cannot be ascribed to residual human RNase P activity as it, alone, cannot cleave substrate tk46 in complexes with catalytically inactive ΔM1(167–377)TK13 RNA. The last result is consistent with observations that a simple stem-loop structure can serve as a substrate for M1 RNA but not for eukaryotic RNase P. This was shown specifically with human and X. laevis RNase P by Yuan and Altman, *Science* 263: 1269–1273 (1994), and Carrara et al., *Proc. Natl. Acad. Sci. USA*. No stimulation of cleavage of substrate tk46 by M1TK13 RNA was observed when fractions devoid of human RNase P activity were used. Accordingly, it is expected that when M1GS RNA constructs are present in mammalian cells, their activity should be enhanced by endogenous proteins.

J. Expression in vivo of M1GS RNA.

Figure 12:
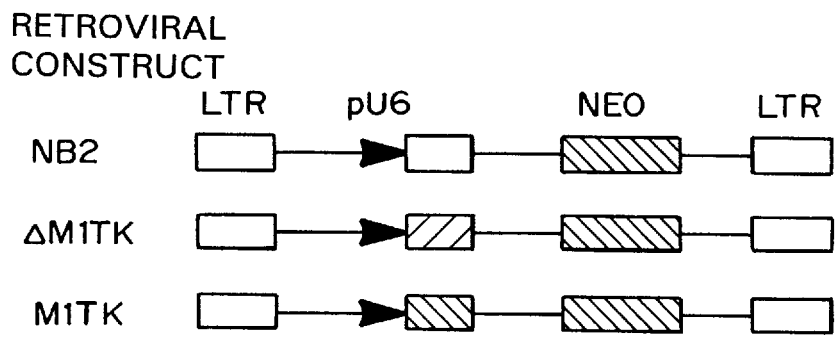
FIG. 12 is a schematic representation of retroviral vectors (ΔM1TK, M1TK, and NB2) containing M1GS RNAs or an EGS sequence complementary to the influenza viral protein PB2.

To express M1GS RNA in mammalian cells, retroviral constructs, M1TK and ΔM1TK, were generated by cloning genes for M1TK13 and ΔM1(163–377)TK13 into the retroviral vector LXSN under the control of a mouse U6 snRNA promoter, described by Das et al., *EMBO J.* 7: 503–512 (1988), and Yuan et al. (1992) (FIG. 12). An additional retroviral DNA construct, NB2, containing the U6 promoter and an external guide sequence (NB2) that targets the mRNA that encodes the PB2 protein of human influenza virus, was used as a control.

The targeted cleavage site of TK mRNA expressed in cells infected with HSV-1 appears to be modifiable by dimethyl sulfate (DMS) in vivo, based on Peattie and Gilbert, *Proc. Natl. Acad. Sci. USA* 77: 4679–4682 (1980), Inoue and Cech, *Proc. Natl. Acad. Sci. USA* 82: 648–652 (1985), Climie and Friesen, *J. Biol. Chem.* 263: 15166–15175 (1988), and Ares and Igel, *Genes & Dev.* 4: 2132–2145

(1990). This is an indication that this site might be accessible for binding to M1GS in vivo. Amphotropic packaging cells (PA317) were transfected with retroviral vector DNAs to produce retroviruses that encoded the genes for M1GS RNA. Subsequently, esotropic packaging cells (ψCRE) were infected with these retroviruses, and cells expressing the retroviruses and ribozymes were cloned. Stable expression of M1GS RNAs was demonstrated by an RNA protection assay with a probe that was complementary to the sequence of M1 RNA and RNA isolated from these cell lines. Furthermore, RNA extracted from M1TK-expressing cells can cleave substrate tk46 in vitro while RNA extracted from the parental ψCRE cells, cells that expressed NB2 RNA and ψM1TK RNA do not show cleavage activity. These results demonstrate that the M1TK RNA that is expressed in cultured cells was intact and catalytically active.

K. Inhibition of expression of TK of HSV-1 in cells that express M1GS RNA

Figure 13:
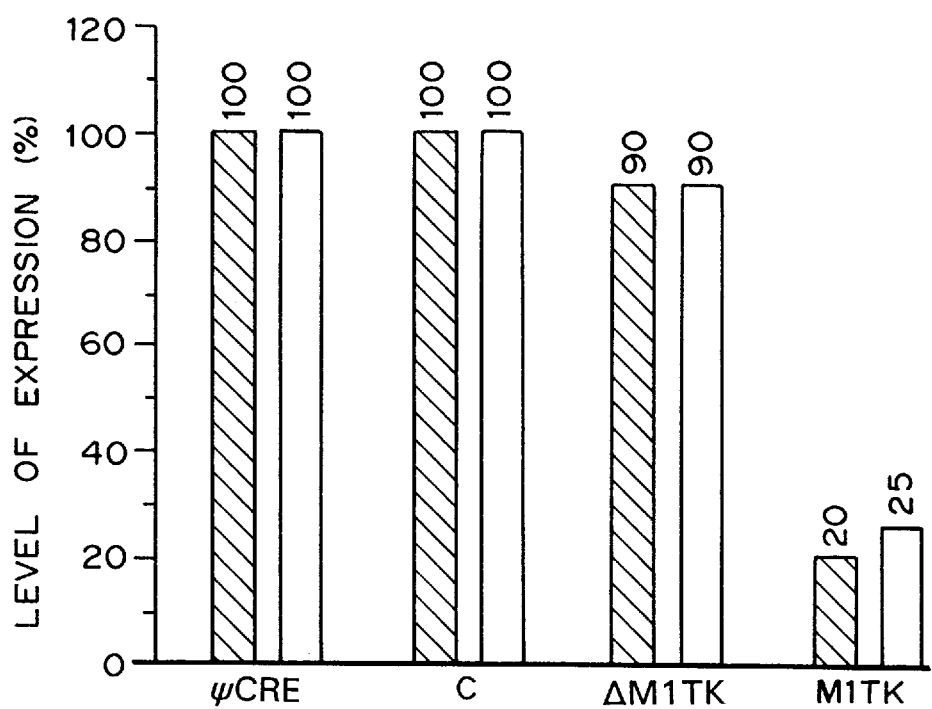
FIG. 13 is a graph of levels of expression (percent of control expression) of TK mRNA and protein in ψCRE cells and in other cell lines. Values are averages of results from four independent experiments. Results from the four experiments varied within 5% in absolute terms.

Cells were infected with herpes simplex virus 1 (HSV-1) at a multiplicity of infection (MOI) of 0.05 to 0.1. Levels of TK mRNA in the infected cells were determined by an RNase protection assay with an RNA probe (TK probe) that contained a sequence of 87 nt complementary to the 5' proximal sequence of TK mRNA. An RNA probe (α47), containing a sequence of 181 nt complementary to the overlapping regions of α47, Us10, and Us11 mRNAs encoded by HSV-1, was used to determine the levels of these latter mRNAs. The levels of the latter RNAs were used as internal controls for quantitation of expression of TK mRNA. FIG. 13 graphically summarizes the results of the RNase protection experiments with both the TK and α47 probes. A reduction of about 80±5%, averaged over four experiments, in the level of TK mRNA expression was observed in cells that expressed M1TK RNA while cells that expressed αM1TK RNA only exhibited a reduction of 9±3%, averaged over four experiments. Thus, it appears that cleavage of TK mRNA by M1TK RNA did indeed occur inside cells, with a subsequent reduction in the level of TK mRNA that could be translated. No products of the cleavage of TK mRNA were detected in our RNase protection assays presumably because these RNAs, which lack either a cap structure or a polyA sequence, are rapidly degraded by intracellular RNases.

Protein extracts of the infected cells were analyzed for the presence of the TK polypeptide. Polypeptides were transferred to two identical membranes and one was stained with a TK-specific antibody (anti-TK), described by Liu and Summers (1988), while the other was stained with a monoclonal antibody against the capsid protein ICP35 of HSV-1 (anti-ICP35), described by Liu and Roizman (1991). The expression of ICP35 serves as an internal control for the quantitation of expression of TK. The results of four independent experiments are summarized in FIG. 13: a reduction of at least 76±5%, averaged over four experiments, in the level of TK protein was observed in cells that expressed M1LTK RNA while a reduction of only 10±4%, averaged over four experiments, was seen in cells that expressed ΔM1TK RNA. The low level of inhibition found in cells that expressed ≠M1TK RNA was presumably due to an antisense effect.

These examples show that when M1 RNA is converted to an RIGS (M1GS RNA), it cleaves one particular substrate in a reaction governed by sequence specificity. A customdesigned RIGS specific for thymidine kinase sequence (M1TK RNA), cleaves the TK mRNA in vitro and can be stably expressed in mammalian cells and can reduce the level of expression of TK by ≧75% when these cells are infected with HSV-1. The reduction in the level of expression of TK that can be ascribed to the antisense effect of the (internal) guide sequence is no more than 15% of the total inhibitory effect. Moreover, the high degree of sequence specificity, which is governed by a guide sequence that hybridizes to a complementary sequence in the substrate, makes our construct suitable for use as a tool for targeting RNAs in vivo. The optimal length of an antisense sequence for in vivo targeting is about 13 nucleotides, as discussed by Stein and Cheng, *Science* 261: 1004–1012 (1993). The extent of inactivation that we observed was very similar to that achieved when endogenous RNase P is used as the catalytic agent to cleave complexes of target TK mRNA and separate EGSs expressed from synthetic genes that have been stably incorporated into human cells in tissue culture.

The activity of M1GS RNA was stimulated in vitro by C5 protein and mammalian proteins. Gold and Altman (1986) suggested that C5 protein and protein subunits of human RNase P might bind to homologous sequences and similar structures that are found in both M1 RNA and H1 RNA, the RNA component of RNase P from HeLa cells. The cleavage reactions by M1LGS RNA in cells that contain proteins that bind RNase P catalytic RNA are expected to proceed at rates higher than those observed in vitro. In particular, higher rates are expected in the presence of additional, non-specific, RNA-binding proteins, RNA chaperons, which are known to stimulate the activity of other RNA enzymes as indicated by Tsuchihashi et al., *Science* 262: 99–102 (1993), Coetzee et al., *Genes & Dev.* 8: 1575–1588 (1994), Bertrand and Rossi, *EMBO J.* 13: 2904–2912 (1994), and Herschlag et al., *EMBO J.* 13: 2913–2924 (1994).

We claim:

1. An isolated oligonucleotide molecule comprising an external guide sequence wherein the external guide sequence comprises a recognition sequence complementary to a targeted sequence in a target RNA molecule, and an RNase P binding sequence, wherein the RNase P binding sequence comprises a nucleotide sequence base pairing with itself to form a structure similar to the T stem and loop of a precursor tRNA, wherein the RNase P binding sequence does not form structure similar to all or portions of the variable stem, the variable loop, the anticodon stem and the anticodon loop of a precursor tRNA, and wherein the external guide sequence promotes eukaryotic RNase P catalytic RNA-mediated cleavage of the target RNA molecule.

2. An isolated oligonucleotide molecule comprising an external guide sequence wherein the external guide sequence comprises a recognition sequence complementary to a targeted sequence in a target RNA molecule, and an RNase P binding sequence, wherein the RNase P binding sequence comprises a nucleotide sequence base pairing with itself to form a structure similar to the T stem and loop of a precursor tRNA, wherein the RNase P binding sequence does not form structure similar to all or portions of the variable stem, the variable loop, the anticodon stem and the anticodon loop of a precursor tRNA, and an RNase P catalytic sequence, wherein the oligonucleotide molecule cleaves the target RNA.

3. The oligonucleotide molecule of claim 2 wherein the RNase P catalytic sequence is an H1 sequence or an M1 sequence.

4. The oligonucleotide molecule of claim 2 wherein the recognition sequence comprises an A recognition arm and a D recognition arm, wherein the A recognition arm is located at the 3' end of the RNase P binding sequence and the D recognition arm is located at the 5' end of the RNase P binding sequence.

5. The oligonucleotide molecule of claim 4 wherein the RNase P catalytic sequence is linked to the 3' end of the A recognition arm.

6. The oligonucleotide molecule of claim 4 wherein the RNase P catalytic sequence is linked to the 5' end of the D recognition arm.

7. The oligonucleotide molecule of claim 4 wherein the RNase P binding sequence consists of a nucleotide sequence base pairing with itself to form a structure similar to the T stem and loop of a precursor tRNA.

8. The oligonucleotide molecule of claim 2 wherein the RNase P catalytic sequence comprises the sequence of a naturally occurring RNase P catalytic RNA.

9. The oligonucleotide molecule of claim 2 wherein the oligonucleotide molecule is selected by randomizing a section of the sequence of the starting oligonucleotide molecule;

selecting for a subpopulation of the randomized sequences for their ability to efficiently cleave the target RNA;

amplifying those sequences cleaving more efficiently than the starting oligonucleotide molecule; and repeating the selection and amplification steps.

10. A composition for promoting cleavage of a target RNA wherein the composition comprises the oligonucleotide molecule of claim 2 in a pharmaceutically acceptable delivery system.

11. The composition of claim 10 wherein the pharmaceutically acceptable delivery system is selected from the group consisting of liposomes, virosomes, microspheres and microcapsules.

12. The composition of claim 10 wherein the pharmaceutically acceptable delivery system is selected from the group consisting of carriers suitable for topical, subcutaneous, parenteral, and enteral administration.

13. A composition for promoting cleavage of a target RNA wherein the composition comprises an engineered expression vector encoding the oligonucleotide molecule of claim 2.

14. The composition of claim 13 wherein the engineered expression vector is a viral vector selected from the group consisting of retroviral vectors, adeno-associated viral vectors and Epstein-Barr viral vectors.

15. A method for cleaving a target RNA comprising bringing into contact, under conditions that promote RNase P cleavage, the target RNA and an oligonucleotide molecule comprising an external guide sequence wherein the external guide sequence comprises a recognition sequence complementary to a targeted sequence in a target RNA molecule, and an RNase P binding sequence, wherein the RNase P binding sequence comprises a nucleotide sequence base pairing with itself to form a structure similar to the T stem and loop of a precursor tRNA, wherein the RNase P binding sequence does not form structure similar to all or portions of the variable stem, the variable loop, the anticodon stem and the anticodon loop of a precursor tRNA, and wherein the external guide sequence promotes RNase P catalytic RNA-mediated cleavage of the target RNA molecule.

16. The method claim 15 wherein the oligonucleotide molecule further comprises an RNase P catalytic sequence, wherein the oligonucleotide molecule cleaves the target RNA.

17. The method of claim 16 wherein the step of bringing into contact is accomplished by administering to a patient or cells from a patient the oligonucleotide molecule, and wherein the oligonucleotide molecule is in a pharmaceutically acceptable delivery system.

18. A method for selecting a population of RNase P internal guide sequences that cleave a target RNA with increased efficiency over a starting RNase P internal guide sequence comprising randomizing a section of the starting RNase P internal guide sequence;

selecting for a subpopulation of the randomized sequences for their ability to efficiently cleave the target RNA;

amplifying those sequences cleaving more efficiently than the starting RNase P internal guide sequence; and repeating the selection and amplification steps.

19. An isolated oligonucleotide molecule comprising an external guide sequence wherein the external guide sequence comprises a recognition sequence complementary to a targeted sequence in a target RNA molecule, and an RNase P binding sequence;

wherein the external guide sequence promotes RNase P catalytic RNA-mediated cleavage of the target RNA molecule, and wherein at least one nucleotide in the oligonucleotide molecule is selected from the group consisting of chemically modified nucleotides and chemically unmodified deoxyribonucleotides.

20. The oligonucleotide molecule of claim 19 wherein the recognition sequence comprises an A recognition arm and a D recognition arm, wherein the A recognition arm is located at the 3' end of the external guide sequence and the D recognition arm is located at the 5' end of the external guide sequence.

21. The oligonucleotide molecule of claim 20 wherein the A recognition arm comprises a nucleotide sequence including at least seven nucleotides complementary to and base pairing with the substrate immediately 3' to a site in the substrate to be cleaved to form a structure similar to an aminoacyl acceptor stem, the RNase P binding sequence comprises a nucleotide sequence base pairing with itself to form a structure similar to the T stem and loop of a precursor tRNA, and the D recognition arm comprises a nucleotide sequence including at least three nucleotides complementary to and base pairing with the substrate.

22. The oligonucleotide molecule of claim 21 wherein the RNase P binding sequence comprises a nucleotide sequence base pairing with itself to form a structure similar to the T stem and loop of a precursor tRNA, and a nucleotide sequence forming structure similar to all or portions of the variable stem, the variable loop, the anticodon stem and the anticodon loop of a precursor tRNA.

23. A composition for promoting cleavage of a target RNA molecule wherein the composition comprises the oligonucleotide molecule of claim 19 in a pharmaceutically acceptable delivery system.

24. The composition of claim 23 wherein the pharmaceutically acceptable delivery system is selected from the group consisting of liposomes, virosomes, microspheres and microcapsules.

25. The oligonucleotide molecule of claim 19 wherein one or more of the 2' hydroxyl groups of the ribonucleotides are replaced with a chemical group selected from the group consisting of hydrogen, an O-alkyl group, an amino group, and fluorine, wherein one or more of the phosphate linking groups are replaced with a linking group selected from the group consisting of methyl phosphonate and phosphorothioate, and wherein replacement of one or more of the 2' hydroxyl groups increases resistance of the external guide sequence to nucleases.

26. The oligonucleotide molecule of claim 19 wherein one or more of the 2' hydroxyl groups of the ribonucleotides are replaced with hydrogen or a methoxy group; and wherein one or more of the phosphate linking groups are replaced with phosphorothioate.

27. The oligonucleotide molecule of claim 19 further comprising an RNase P binding sequence, wherein the oligonucleotide molecule cleaves the target RNA.

28. An DNA molecule that encodes an RNA molecule comprising an external guide sequence wherein the external guide sequence comprises a recognition sequence complementary to a targeted sequence in a target RNA molecule, and an RNase P binding sequence, wherein the RNase P binding sequence comprises a nucleotide sequence base pairing with itself to form a structure similar to the T stem and loop of a precursor tRNA, wherein the RNase P binding sequence does not form structure similar to all or portions of the variable stem, the variable loop, the anticodon stem and the anticodon loop of a precursor tRNA, and wherein the external guide sequence promotes eukaryotic RNase P catalytic RNA-mediated cleavage of the target RNA molecule.

29. The DNA molecule of claim 28 wherein the RNA molecule further comprises an RNase P catalytic sequence, wherein the RNA molecule cleaves the target RNA.

30. An isolated oligonucleotide molecule comprising an external guide sequence wherein the external guide sequence comprises an RNase P binding sequence, wherein the RNase P binding sequence comprises a nucleotide sequence base pairing with itself to form a structure similar to the T stem and loop of a precursor tRNA, wherein the RNase P binding sequence does not form structure similar to all or portions of the variable stem, the variable loop, the anticodon stem and the anticodon loop of a precursor tRNA, and a recognition sequence complementary to a targeted sequence in a target RNA molecule, wherein the recognition sequence comprises an A recognition arm and a D recognition arm, wherein the A recognition arm is located at the 3' end of the RNase P binding sequence and the D recognition arm is located at the 5' end of the RNase P binding sequence, and wherein the external guide sequence promotes eukaryotic RNase P catalytic RNA-mediated cleavage of the target RNA molecule.

* * * * *